(12) United States Patent
Biggadike et al.

(10) Patent No.: US 7,442,836 B2
(45) Date of Patent: *Oct. 28, 2008

(54) PHENETHANOLAMINE DERIVATIVES FOR TREATMENT OF RESPIRATORY DISEASES

(75) Inventors: Keith Biggadike, Stevenage (GB);
Diane Mary Coe, Stevenage (GB);
Dean David Edney, Dartford (GB);
Stephen Barry Guntrip, Stevenage (GB); Abigail Halton, Dartford (GB);
Brian Edgar Looker, Stevenage (GB);
Michael John Monteith, Dartford (GB);
Rebecca Jane Moore, Dartford (GB);
Rajnikant Patel, Dartford (GB);
Panayiotis Alexandrou Procopiou, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/426,657

(22) Filed: Jun. 27, 2006

(65) Prior Publication Data

US 2006/0287389 A1 Dec. 21, 2006

Related U.S. Application Data

(63) Continuation of application No. 10/467,733, filed as application No. PCT/EP02/01387 on Feb. 11, 2002, now Pat. No. 7,135,600.

(30) Foreign Application Priority Data

Feb. 14, 2001 (GB) ................................ 0103630.0
Nov. 9, 2001 (GB) ................................ 0126998.4

(51) Int. Cl.
*C07C 303/00* (2006.01)

(52) U.S. Cl. .................... 564/86; 560/61; 514/171; 514/548; 514/602

(58) Field of Classification Search ................ 568/583, 568/589, 592, 626, 659, 731; 514/715, 716, 514/717, 727, 728, 736
See application file for complete search history.

(56) References Cited

U.S. PATENT DOCUMENTS

| 2,140,800 | A | 12/1938 | Leemans |
|---|---|---|---|
| 3,994,974 | A | 11/1976 | Murakami et al. |
| 4,730,008 | A | 3/1988 | Skidmore et al. |
| 4,853,381 | A | 8/1989 | Finch et al. |
| 4,853,382 | A | 8/1989 | Skidmore et al. |
| 4,908,386 | A | 3/1990 | Finch et al. |
| 4,937,268 | A | 6/1990 | Skidmore et al. |
| 4,963,564 | A | 10/1990 | Skidmore et al. |
| 4,990,505 | A | 2/1991 | Skidmore et al. |
| 4,992,474 | A | 2/1991 | Skidmore et al. |
| 4,997,986 | A | 3/1991 | Mitchell et al. |
| 5,066,678 | A | 11/1991 | Skidmore et al. |
| 5,091,422 | A | 2/1992 | Skidmore et al. |
| 5,099,068 | A | 3/1992 | Mitchell et al. |
| 5,109,023 | A | 4/1992 | Mitchell et al. |
| 5,126,375 | A | 6/1992 | Skidmore et al. |
| 5,225,445 | A | 7/1993 | Skidmore et al. |
| 5,243,076 | A | 9/1993 | Skidmore et al. |
| 5,283,262 | A | 2/1994 | Mitchell et al. |
| 5,552,438 | A | 9/1996 | Christensen, IV |
| 5,998,428 | A | 12/1999 | Barnette et al. |

FOREIGN PATENT DOCUMENTS

| EP | 0069715 | 1/1983 |
|---|---|---|
| EP | 162576 | 11/1985 |
| EP | 220054 | 4/1987 |
| EP | 220878 | 5/1987 |
| EP | 223410 | 5/1987 |
| EP | 286242 | 10/1988 |
| EP | 303465 | 2/1989 |
| EP | 317206 | 5/1989 |
| EP | 0416951 | 3/1991 |
| EP | 223671 | 11/1991 |
| EP | 0401966 | 1/1994 |
| EP | 0947498 | 10/1999 |
| GB | 2140800 | 12/1984 |
| GB | 2159151 | 11/1985 |
| GB | 2162842 | 2/1986 |
| GB | 2169265 | 7/1986 |
| GB | 2176476 | 12/1986 |
| GB | 2178965 | 2/1987 |
| WO | WO 95/01170 | 1/1995 |
| WO | WO 99/16766 | 4/1999 |
| WO | WO 99/47505 | 9/1999 |
| WO | 0051599 | 9/2000 |
| WO | WO 01/13953 | 3/2001 |
| WO | 02066422 | 8/2002 |
| WO | 02070490 | 9/2002 |

OTHER PUBLICATIONS

Fuji et al., "Novel phosphodiesterase 4 inhibitor T-440 reverses and prevents human bronchial contraction induced by allergen," *J Pharmacol Exp Ther* 284(1):162 (1998).

Landells et al., "Oral administration of the phosphodiesterase (PDE)4 inhibitor, V11294A inhibits ex-vivo agonist-induced-cell activation,"*Eur Resp J (Iannu Cong Eur Resp Soc, Geneva)* 12(Suppl. 28) Abst P2393 (Sep. 1998).

(Continued)

*Primary Examiner*—Deborah D Carr
(74) *Attorney, Agent, or Firm*—Robert J. Smith

(57) ABSTRACT

The present invention relates to novel compounds of Formula (I), to a process for their manufacture, to pharmaceutical compositions containing them, and to their use in therapy, in particular their use in the prophylaxis and treatment of respiratory diseases.

15 Claims, 3 Drawing Sheets

OTHER PUBLICATIONS

McHale et al., "Expression of human recombinant cAMP phosphodiesterase isozyme IV reverses growth arrest phenotypes in phosphodiesterase-deficient yeast," *Mol Pharmacol* 39:109-113 (1991).

Nicholson et al., "Differential modulation of tissue function and therapeutic potential of selective inhibitors of cyclic nucleotide phosphodiesterase isoenzymes," *Trends Pharmacol Sci* 12:19-27 (1991).

Thornber, "Isosterism and molecular modification in drug design," *Chemical Society Reviews*:8(4)563-580 (1979).

Torphy et al., "Role of cyclic nucleotide phosphodiesterase isozymes in intact canine trachealis," *Mol. Pharmacol* 39:376-384 (1991).

U.S. Appl. No. 10/472,343, filed Mar. 5, 2004, Keith Biggadike et al.

Dr. Meyer Magarici; "Riesgossobre broncodilatadors"; SVMS; Nov. 29, 2005.

Drug Bank Chemical Compound Query Result re Salmeterol.

D. Iakovidis, et al.; "Synthesis and beta-andrenoceptor agonist properties of (+/−)-1-(3',4'-dihydroxyphenoxy)-3-(3",4"-dimethooxyphenyl)ethylamino-2-propanol hydrochloride, (+/−)-(RO363.HCI, and the (2S)-(−)-isomer": European Journal of Medicinal Chemistry; Jun. 6, 1999; vol. 34, No. 6, pp. 539-548.

Robert Hett, et al.; "Enantioselective synthesis of salmeterol via asymmetric borane reduction"; Tetrahedron Letters; 1994; vol. 35, No. 50.

PHENETHANOLAMINE DERIVATIVES FOR TREATMENT OF RESPIRATORY DISEASES

CROSS-REFERENCE TO RELATED APPLICATIONS

This application is a continuation application of Ser. No. 10/467,733, now U.S. Pat. No. 7,135,600, filed Feb. 9, 2004 under 35 U.S.C. § 371 as the United States National Phase Application of International Application No. PCT/EPO02/01387 filed Feb. 11, 2002 claiming priority from Great Britain Application Nos. 0103630.0 and 0126998.4, filed Feb. 14, 2001 and Nov. 9, 2001 respectively, the disclosures of which are incorporated herein by reference in their entirety.

The present invention is concerned with phenethanolamine derivatives, processes for their preparation, compositions containing them and their use in medicine, particularly in the prophylaxis and treatment of respiratory diseases.

Certain phenethanolamine compounds are known in the art as having selective stimulant action at $\beta_2$-adrenoreceptors and therefore having utility in the treatment of bronchial asthma and related disorders. Thus GB 2 140 800 describes phenethanolamine compounds including 4-hydroxy-$\alpha^1$-[[[6-(4-phenylbutoxy)hexyl]amino]methyl]-1,3-benzene-dimethanol 1-hydroxy-2-naphthalenecarboxylate (salmeterol xinafoate) which is now used clinically in the treatment of such medical conditions.

Although salmeterol and the other commercially available $\beta_2$-adrenoreceptor agonists are effective bronchodilators, the maximum duration of action is 12 hours, hence twice daily dosing is often required. There is therefore a clinical need for compounds having potent and selective stimulant action at $\beta_2$-adrenoreceptors and having an advantageous profile of action.

According to the present invention, there is provided a compound of formula (I)

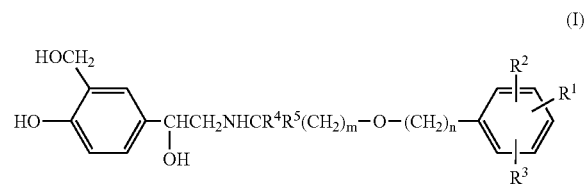

(I)

or a salt, solvate, or physiologically functional derivative thereof, wherein:

m is an integer of from 2 to 8;
n is an integer of from 3 to 11, preferably from 3 to 7;
with the proviso that m+n is 5 to 19, preferably 5 to 12;

$R^1$ is —$XSO_2NR^6R^7$ wherein X is —$(CH_2)_p$— or $C_2$-6 alkenylene;
$R^6$ and $R^7$ are independently selected from hydrogen, $C_{1-6}$alkyl,
$C_{3-7}$cycloalkyl, $C(O)NR^8R^9$, phenyl, and phenyl ($C_{1-4}$alkyl)-,
or $R^6$ and $R^7$, together with the nitrogen to which they are bonded, form a 5-, 6-, or 7-membered nitrogen containing ring,
and $R^6$ and $R^7$ are each optionally substituted by one or two groups selected from halo, $C_{1-6}$alkyl, $C_{1-6}$haloalkyl, $C_{1-6}$alkoxy, hydroxy-substituted $C_{1-6}$alkoxy, —$CO_2R^8$, —$SO_2NR^8R^9$, —$CONR^8R^9$, —$NR^8C(O)R^9$, or a 5-, 6- or 7-membered heterocylic ring;

$R^8$ and $R^9$ are independently selected from hydrogen, $C_{1-6}$alkyl,
$C_{3-6}$cycloalkyl, phenyl, and phenyl ($C_{1-4}$alkyl)-; and
p is an integer of from 0 to 6, preferably from 0 to 4;
$R^2$ and $R^3$ are independently selected from hydrogen, $C_{1-6}$alkyl, $C_{1-6}$alkoxy, halo, phenyl, and $C_{1-6}$haloalkyl; and
$R^4$ and $R^5$ are independently selected from hydrogen and $C_{1-4}$alkyl with the proviso that the total number of carbon atoms in $R^4$ and $R^5$ is not more than 4.

In the compounds of formula (I) the group $R^1$ is preferably attached to the meta-position relative to the —O—$(CH_2)_n$— link.

$R^1$ preferably represents —$SO_2NR^6R^7$ wherein $R^6$ and $R^7$ are independently selected from hydrogen and $C_{1-6}$alkyl, more preferably $R^1$ is —$SO_2NH_2$.

$R^4$ and $R^5$ are preferably independently selected from hydrogen and methyl, more preferably $R^4$ and $R^5$ are both hydrogen.

m is suitably 4, 5, or 6, and n is suitably 3, 4, 5 or 6. Preferably m is 5 or 6 and n is 3 or 4, such that m+n is 8, 9 or 10, preferably 9.

According to a preferred aspect of the invention, there is provided a compound of formula (Ia)

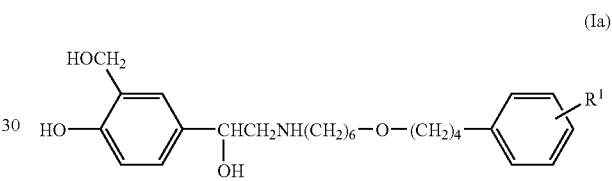

(Ia)

or a salt, solvate, or physiologically functional derivative thereof, wherein
$R^1$ is as defined above for formula (I).

According to a further preferred aspect of the invention, there is provided a compound of formula (Ib)

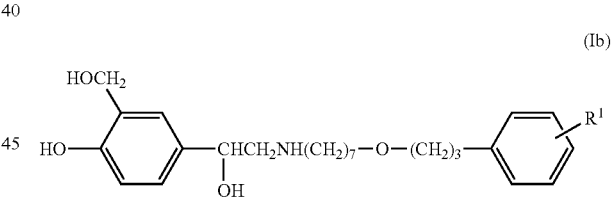

(Ib)

or a salt, solvate, or physiologically functional derivative thereof, wherein
$R^1$ is as defined above for formula (I).

In the compounds of formulae (Ia) and (Ib), the group $R^1$ is preferably attached to the meta-position relative to the —O—$(CH_2)_n$—, —O—$(CH_2)_4$— or —O—$(CH_2)_3$— link respectively.

In the compounds of formulae (Ia) and (Ib), $R^1$ is preferably —$SO_2NR^6R^7$ wherein $R^6$ and $R^7$ are independently selected from hydrogen and $C_{1-6}$alkyl, more preferably $R^1$ is —$SO_2NH_2$.

It is to be understood that the present invention covers all combinations of particular and preferred groups described hereinabove.

Figure 1:
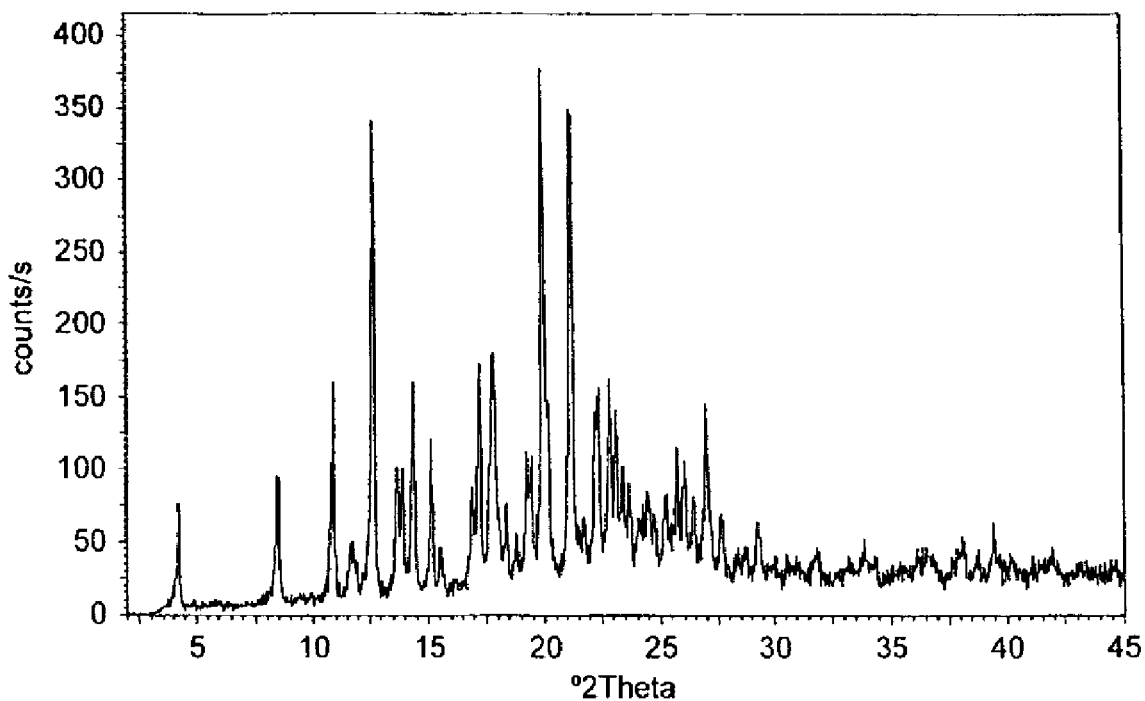
FIG. 1 illustrates the X-Ray Powder Diffraction (XRPD) pattern of the product referred to in Example 48(ii).

Preferred compounds of the invention include:

3-(4-{[6-({(2R)-2-Hydroxy-2-[4-hydroxy-3-(hydroxymethyl)phenyl]ethyl}-amino)hexyl]oxy}butyl)benzenesulfonamide;

4-(4-{[6-({(2R)-2-Hydroxy-2-[4-hydroxy-3-(hydroxymethyl)phenyl]ethyl}-amino)hexyl]oxy}butyl)benzenesulfonamide;

2-(4-{[6-({(2R)-2-Hydroxy-2-[4-hydroxy-3-(hydroxymethyl)phenyl]ethyl}-amino)hexyl]oxy}butyl)benzenesulfonamide;

3-(4-{[6-({(2R)-2-Hydroxy-2-[4-hydroxy-3-(hydroxymethyl)phenyl]ethyl}-amino)hexyl]oxy}butyl)-N-methylbenzenesulfonamide;

2-(Hydroxymethyl)-4-{(1R)-1-hydroxy-2-[(6-{4-[3-(morpholin-4-ylsulfonyl)-phenyl]butoxy}hexyl)amino]ethyl}phenol;

3-(4-{[6-({(2R)-2-Hydroxy-2-[4-hydroxy-3-(hydroxymethyl)phenyl]ethyl}-amino)hexyl]oxy}butyl)-N,N-dimethylbenzenesulfonamide;

3-(4-{[6-({(2R)-2-Hydroxy-2-[4-hydroxy-3-(hydroxymethyl)phenyl]ethyl}-amino)hexyl]oxy}butyl)-N-isopropylbenzenesulfonamide;

N-(tert-Butyl)-3-(4-{[6-({(2R)-2-hydroxy-2-[4-hydroxy-3-(hydroxymethyl)phenyl]-ethyl}amino)hexyl]oxy}butyl)benzenesulfonamide;

2-(Hydroxymethyl)-4-{(1R)-1-hydroxy-2-[(6-{4-[3-(piperidin-1-ylsulfonyl)phenyl]-butoxy}hexyl)amino]ethyl}phenol;

1-[3-(4-{[6-({(2R)-2-Hydroxy-2-[4-hydroxy-3-(hydroxymethyl)phenyl]ethyl}amino)-hexyl]oxy}butyl)phenyl]methanesulfonamide;

3-(5-{[5-({(2R)-2-hydroxy-2-[4-hydroxy-3-(hydroxymethyl)phenyl]ethyl}-amino)pentyl]oxy}pentyl)benzenesulfonamide;

3-(3-{[7-({(2R)-2-hydroxy-2-[4-hydroxy-3-(hydroxymethyl)phenyl]ethyl}-amino)heptyl]oxy}propyl)benzenesulfonamide;

3-{6-[4-({(2R)-2-hydroxy-2-[4-hydroxy-3-(hydroxymethyl)phenyl]ethyl}-amino)butoxy]hexyl}benzenesulfonamide;

4-[3-(4-{[6-({(2R)-2-Hydroxy-2-[4-hydroxy-3-(hydroxymethyl)phenyl]ethyl}-amino)hexyl]oxy}butyl)phenyl]butane-1-sulfonamide;

3-(5-{[6-({(2R)-2-Hydroxy-2-[4-hydroxy-3-(hydroxymethyl)phenyl]ethyl}-amino)hexyl]oxy}pentyl)benzenesulfonamide;

3-(6-{[6-({(2R)-2-Hydroxy-2-[4-hydroxy-3-(hydroxymethyl)phenyl]ethyl}-amino)hexyl]oxy}hexyl)benzenesulfonamide;

3-(3-{[6-({(2R)-2-Hydroxy-2-[4-hydroxy-3-(hydroxymethyl)phenyl]ethyl}-amino)hexyl]oxy}propyl)benzenesulfonamide;

3-(4-{[5-({(2R)-2-Hydroxy-2-[4-hydroxy-3-(hydroxymethyl)phenyl]ethyl}amino)pentyl]oxy}butyl)benzenesulfonamide;

1-[2-(4-{[6-({(2R)-2-Hydroxy-2-[4-hydroxy-3-(hydroxymethyl)phenyl]ethyl}amino)hexyl]oxy}butyl)phenyl]methanesulfonamide;

1-[4-(4-{[6-({(2R)-2-Hydroxy-2-[4-hydroxy-3-(hydroxymethyl)phenyl]ethyl}amino)hexyl]oxy}butyl)phenyl]methanesulfonamide;

N-[3-(Aminosulfonyl)phenyl]-3-(4-{[6-({(2R)-2-hydroxy-2-[4-hydroxy-3-(hydroxymethyl)phenyl]ethyl}amino)hexyl]oxy}butyl)benzenesulfonamide;

N-Benzyl-3-(4-{[6-({(2R)-2-hydroxy-2-[4-hydroxy-3-(hydroxymethyl)phenyl]ethyl}amino)hexyl]oxy}butyl)benzenesulfonamide;

4-{(1R)-2-[(6-{4-[3-({[(Ethylamino)carbonyl]amino}sulfonyl)phenyl]butoxy}-hexyl)amino]-1-hydroxyethyl}-1-hydroxy-2-(hydroxymethyl)benzene;

3-(4-{[6-(f{2-Hydroxy-2-[4-hydroxy-3-(hydroxymethyl)phenyl]ethyl}amino)hexyl]oxy}butyl)benzenesulfonamide;

3-(4-{[6-({(2S)-2-Hydroxy-2-[4-hydroxy-3-(hydroxymethyl)phenyl]ethyl}amino)hexyl]oxy}butyl)benzenesulfonamide;

N-[4-({[3-(4-{[6-({(2R)-2-Hydroxy-2-[4-hydroxy-3-(hydroxymethyl)phenyl]ethyl}-amino)hexyl]oxy}butyl)phenyl]sulfonyl}amino)phenyl]acetamide N-Cyclobutyl-3-(4-{[6-({(2R)-2-hydroxy-2-[4-hydroxy-3-(hydroxymethyl)phenyl]ethyl}amino)hexyl]oxy}butyl)benzenesulfonamide;

N-Cyclohexyl-3-(4-{[6-({(2R)-2-hydroxy-2-[4-hydroxy-3-(hydroxymethyl)phenyl]ethyl}amino)hexyl]oxy}butyl)benzenesulfonamide;

3-(4-{[6-({(2R)-2-Hydroxy-2-[4-hydroxy-3-(hydroxymethyl)phenyl]ethyl}-amino)hexyl]oxy}butyl)-N-(2-morpholin-4-ylethyl)benzenesulfonamide;

N-[2-(2-Hydroxyethoxy)ethyl]-3-(4-{[6-({(2R)-2-hydroxy-2-[4-hydroxy-3-(hydroxymethyl)phenyl]ethyl}amino)hexyl]oxy}butyl)benzenesulfonamide;

N-(4-Fluorophenyl)-3-(4-{[6-({(2R)-2-hydroxy-2-[4-hydroxy-3-(hydroxymethyl)phenyl]ethyl}amino)hexyl]oxy}butyl)benzenesulfonamide;

N-[4-(Aminosulfonyl)phenyl]-3-(4-{[6-({(2R)-2-hydroxy-2-[4-hydroxy-3-(hydroxymethyl)phenyl]ethyl}amino)hexyl]oxy}butyl)benzenesulfonamide;

2-(Hydroxymethyl)-4-{(1R)-1-hydroxy-2-[(6-{4-[3-(piperazin-1-ylsulfonyl)phenyl]butoxy}hexyl)amino]ethyl}phenol;

3-(4-{[6-({(2R)-2-Hydroxy-2-[4-hydroxy-3-(hydroxymethyl)phenyl]ethyl}-amino)hexyl]oxy}butyl)-N-(1-methyl-1-phenylethyl)benzenesulfonamide;

5-(4-{[6-({(2R)-2-Hydroxy-2-[4-hydroxy-3-(hydroxymethyl)phenyl]-ethyl}amino)hexyl]oxy}butyl)-2-methoxybenzenesulfonamide;

3-(4-{[6-({(2R)-2-Hydroxy-2-[4-hydroxy-3-(hydroxymethyl)phenyl]ethyl}-amino)hexyl]oxy}butyl)-5-pentylbenzenesulfonamide;

(E)-2-[3-(4-{[6-({(2R)-2-Hydroxy-2-[4-hydroxy-3-(hydroxymethyl)phenyl]ethyl}-amino)hexyl]oxy}butyl)phenyl]-N-methylethenesulfonamide;

2-[3-(4-{[6-({(2R)-2-Hydroxy-2-[4-hydroxy-3-(hydroxymethyl)phenyl]ethyl}amino)hexyl]oxy}butyl)phenyl]ethanesulfonamide;

5-(4-{[6-({(2R)-2-Hydroxy-2-[4-hydroxy-3-(hydroxymethyl)phenyl]ethyl}amino)hexyl]oxy}butyl)[1,1'-biphenyl]-3-sulfonamide;

3-Fluoro-5-(4-{[6-({(2R)-2-hydroxy-2-[4-hydroxy-3-(hydroxymethyl)phenyl]ethyl}amino)hexyl]oxy}butyl)benzenesulfonamide;

5-(4-{[6-({(2R)-2-Hydroxy-2-[4-hydroxy-3-(hydroxymethyl)phenyl]ethyl}amino)hexyl]oxy}butyl)-3-trifluoromethylbenzenesulfonamide;

3-(4-{[6-({(2R)-2-Hydroxy-2-[4-hydroxy-3-(hydroxymethyl)phenyl]ethyl}amino)hexyl]oxy}butyl)-5-methylbenzenesulfonamide acetate N-{[3-(4-{[6-({(2R)-2-Hydroxy-2-[4-hydroxy-3-(hydroxymethyl)phenyl]ethyl}amino)hexyl]oxy}butyl)phenyl]sulfonyl}glycine;

N²-{[3-(4-{[6-({(2R)-2-Hydroxy-2-[4-hydroxy-3-(hydroxymethyl)phenyl]ethyl}amino)hexyl]oxy}butyl)phenyl]sulfonyl}glycinamide;

and salts, solvates, and physiologically functional derivatives thereof.

Particularly preferred compounds of the invention include:

3-(4-{[6-({(2R)-2-Hydroxy-2-[4-hydroxy-3-(hydroxymethyl)phenyl]ethyl}-amino)hexyl]oxy}butyl)benzenesulfonamide;

3-(4-{[6-({(2S)-2-Hydroxy-2-[4-hydroxy-3-(hydroxymethyl)phenyl]ethyl}-amino)hexyl]oxy}butyl)benzenesulfonamide;

3-(4-{[6-({(2R/S)-2-Hydroxy-2-[4-hydroxy-3-(hydroxymethyl)phenyl]ethyl}-amino)hexyl]oxy}butyl)benzenesulfonamide;

3-(3-{[7-({(2R)-2-hydroxy-2-[4-hydroxy-3-(hydroxymethyl)phenyl]ethyl}-amino)heptyl]oxy}propyl)benzenesulfonamide;

3-(3-{[7-({(2S)-2-hydroxy-2-[4-hydroxy-3-(hydroxymethyl)phenyl]ethyl}-amino)heptyl]oxy}propyl)benzenesulfonamide;

3-(3-{[7-({(2R/S)-2-hydroxy-2-[4-hydroxy-3-(hydroxymethyl)phenyl]ethyl}-amino)heptyl]oxy}propyl)benzenesulfonamide;

and salts, solvates, and physiologically functional derivatives thereof.

Of these compounds, 3-(4-{[6-({(2R)-2-hydroxy-2-[4-hydroxy-3-(hydroxymethyl)-phenyl]ethyl}amino)hexyl]oxy}butyl)benzenesulfonamide and 3-(3-{[7-({(2R)-2-hydroxy-2-[4-hydroxy-3-hydroxymethyl)phenyl]ethyl}-amino)heptyl]oxy}propyl)benzenesulfonamide are especially preferred.

In the definition of $R^1$ where '$R^6$ and $R^7$ together with the nitrogen atom to which they are bonded, form a 5-, 6-, or 7-membered nitrogen containing ring', the term "5-, 6-, or 7-membered nitrogen containing ring" means a 5-, 6-, or 7-membered saturated or unsaturated ring which includes the sulfonamide nitrogen atom and optionally 1 or 2 other heteroatoms independently selected from nitrogen, sulphur, and oxygen. Suitable examples of such a ring include piperidinyl, morpholinyl, and piperazinyl.

In the definition of $R^1$, specifically the optional substituents on $R^6$ and $R^7$, the term "5-, 6-, or 7-membered heterocyclic ring" means a 5-, 6-, or 7-membered fully or partially saturated or unsaturated ring which includes 1, 2, 3 or 4 heteroatoms independently selected from nitrogen, sulphur, and oxygen. Suitable examples of such a ring include pyrrolyl, furyl, thienyl, pyridinyl, pyrazinyl, pyridazinyl, imidazolyl, tetrazolyl, tetrahydrofuranyl, oxazolyl, thiazolyl, thiadiazolyl, piperidinyl, morpholinyl, and piperazinyl.

In the definition of X, the term "alkenylene" includes both cis and trans structures. Suitable examples of alkenylene groups include —CH=CH—.

The compounds of formulae (I), (Ia) and (Ib) include an asymmetric centre, namely the carbon atom of the

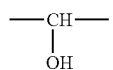

group. The present invention includes both (S) and (R) enantiomers either in substantially pure form or admixed in any proportions.

Similarly, where $R^4$ and $R^5$ are different groups, the carbon atom to which they are attached is an asymmetric centre and the present invention includes both (S) and (R) enantiomers at this centre either in substantially pure form or admixed in any proportions.

Thus the compounds of formulae (I), (Ia) and (Ib) include all enantiomers and diastereoisomers as well as mixtures thereof in any proportions.

Salts and solvates of compounds of formulae (I), (Ia) and (Ib) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formulae (I), (Ia) and (Ib) and their pharmaceutically acceptable salts, solvates, and physiologically functional derivatives.

By the term "physiologically functional derivative" is meant a chemical derivative of a compound of formula (I), (Ia) or (Ib) having the same physiological function as the parent compound of formula (I), (Ia) or (Ib), for example, by being convertible in the body thereto.

According to the present invention, examples of physiologically functional derivatives include esters.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, sulphamic, sulphanilic, succinic, oxalic, fumaric, maleic, malic, glutamic, aspartic, oxaloacetic, methanesulphonic, ethanesulphonic, arylsulphonic (for example p-toluenesulphonic, benzenesulphonic, naphthalenesulphonic or naphthalenedisulphonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Advantageously, preferred compounds of the invention such as 3-(4-{[6-({(2R)-2-hydroxy-2-[4-hydroxy-3-(hydroxymethyl)-phenyl]ethyl}amino)hexyl]oxy}butyl)benzenesulfonamide and 3-(3-{[7-({(2R)-2-hydroxy-2-[4-hydroxy-3-hydroxymethyl)phenyl]ethyl}-amino)heptyl]oxy}propyl)benzenesulfonamide are provided in the form of a crystalline salt, for example selected from those exemplified in the experimental section below. Said crystalline salts have favourable physical properties such as low hygroscopicity and/or improved stability. Particularly preferred salts include the cinnamate, 4-methoxycinnamate, 4-methylcinnamate, naphthalenepropenoate and 4-phenylcinnamate salts.

Pharmaceutically acceptable esters of the compounds of formulae (I), (Ia) and (Ib) may have a hydroxyl group converted to a $C_{1-6}$alkyl, aryl, aryl $C_{1-6}$ alkyl, or amino acid ester.

As mentioned above, the compounds of formulae (I), (Ia) and (Ib) are selective $\beta_2$-adrenoreceptor agonists as demonstrated using functional or reporter gene readout from cell lines transfected with human beta-adrenoreceptors as described below. Compounds according to the present invention also have the potential to combine long duration of effect with rapid onset of action. Furthermore, certain compounds have shown an improved therapeutic index in animal models relative to existing long-acting $\beta_2$-agonist bronchodilators. As such, compounds of the invention may be suitable for once-daily administration.

Compounds of formulae (I), (Ia) and (Ib) and their pharmaceutically acceptable salts, solvates, and physiologically functional derivatives have use in the prophylaxis and treatment of clinical conditions for which a selective $\beta_2$-adrenoreceptor agonist is indicated. Such conditions include diseases associated with reversible airways obstruction such as asthma, chronic obstructive pulmonary diseases (COPD) (e.g. chronic and wheezy bronchitis, emphysema), respiratory tract infection and upper respiratory tract disease (e.g. rhinitis, including seasonal and allergic rhinitis).

Other conditions which may be treated include premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

Accordingly, the present invention provides a method for the prophylaxis or treatment of a clinical condition in a mammal, such as a human, for which a selective $\beta_2$-adrenoreceptor agonist is indicated, which comprises administration of a therapeutically effective amount of a compound of formula (I), (Ia) or (Ib), or a pharmaceutically acceptable salt, solvate, or physiologically functional derivative thereof. In particular, the present invention provides such a method for the prophylaxis or treatment of a disease associated with reversible airways obstruction such as asthma, chronic obstructive pulmonary disease (COPD), respiratory tract infection or upper respiratory tract disease. In a further aspect the present invention provides such a method for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

In the alternative, there is also provided a compound of formula (I), (Ia) or (Ib) or a pharmaceutically acceptable salt, solvate, or physiologically functional derivative thereof for use in medical therapy, particularly, for use in the prophylaxis or treatment of a clinical condition in a mammal, such as a human, for which a selective $\beta_2$-adrenoreceptor agonist is indicated. In particular, there is provided a compound of formula (I), (Ia) or (Ib) or a pharmaceutically acceptable salt, solvate, or physiologically functional derivative thereof for the prophylaxis or treatment of a disease associated with reversible airways obstruction such as asthma, chronic obstructive pulmonary disease (COPD), respiratory tract infection or upper respiratory tract disease. In a further aspect, there is provided a compound of formula (I), (Ia) or (Ib) or a pharmaceutically acceptable salt, solvate, or physiologically functional derivative thereof for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

The present invention also provides the use of a compound of formula (I), (Ia) or (Ib), or a pharmaceutically acceptable salt, solvate, or physiologically functional derivative thereof in the manufacture of a medicament for the prophylaxis or treatment of a clinical condition for which a selective $\beta_2$-adrenoreceptor agonist is indicated, for example a disease associated with reversible airways obstruction such as asthma, chronic obstructive pulmonary disease (COPD), respiratory tract infection or upper respiratory tract disease. In a further aspect, there is provided a compound of formula (I), (Ia) or (Ib), or a pharmaceutically acceptable salt, solvate, or physiologically functional derivative thereof in the manufacture of a medicament for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

The amount of a compound of formula (I), (Ia) or (Ib), or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The compounds of the invention may be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1 mg per day.

While it is possible for the compound of formula (I), (Ia) or (Ib), or a pharmaceutically acceptable salt, solvate, or physiologically functional derivative thereof to be administered alone, it is preferable to present it as a pharmaceutical formulation.

Accordingly, the present invention further provides a pharmaceutical formulation comprising a compound of formula (I), (Ia) or (Ib) or a pharmaceutically acceptable salt, solvate, or physiologically functional derivative thereof, and a pharmaceutically acceptable carrier or excipient, and optionally one or more other therapeutic ingredients.

Hereinafter, the term "active ingredient" means a compound of formula (I), (Ia) or (Ib), or a pharmaceutically acceptable salt, solvate, or physiologically functional derivative thereof.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Dry powder compositions for topical delivery to the lung by inhalation may, for example, be presented in capsules and cartridges of for example gelatine, or blisters of for example laminated aluminium foil, for use in an inhaler or insulator. Formulations generally contain a powder mix for inhalation of the compound of the invention and a suitable powder base (carrier substance) such as lactose or starch. Use of lactose is preferred. Each capsule or cartridge may generally contain between 20 μg-10 mg of the compound of formula (I) optionally in combination with another therapeutically active ingredient. Alternatively, the compound of the invention may be presented without excipients. Packaging of the formulation may be suitable for unit dose or multi-dose delivery. In the case of multi-dose delivery, the formulation can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose an acacia.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds and pharmaceutical formulations according to the invention may be used in combination with or include one or more other therapeutic agents, for example selected from anti-inflammatory agents, anticholinergic agents (particularly an $M_1$, $M_2$, $M_1/M_2$ or $M_3$ receptor antagonist), other $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example a corticosteroid or an NSAID), an anticholinergic agent, another $\beta_2$-adrenoreceptor agonist, an antiinfective agent (e.g. an antibiotic or an antiviral), or an antihistamine. Preferred are combinations comprising a compound of formula (I) or a pharmaceutically acceptable salt, solvate or physiologically functional derivative thereof together with a corticosteroid, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Of particular interest is use of the compound of formula (I) in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

Initial experiments may be conducted to establish and validate a [$^3$H]-rolipram binding assay. Details of this work are given in the Binding Assays described in detail below.

Phosphodiesterase and Rolipram Binding Assays

Assay method 1A

Isolated human monocyte PDE4 and hrPDE (human recombinant PDE4) was determined to exist primarily in the low affinity form. Hence, the activity of test compounds against the low affinity form of PDE4 can be assessed using standard assays for PDE4 catalytic activity employing 1 μM [$^3$H]cAMP as a substrate (Torphy et al., J. of Biol. Chem., Vol. 267, No. 3 pp 1798-1804, 1992). Rat brain high speed supernatants were used as a source of protein and both enantiomers of [$^3$H]-rolipram were prepared to a specific activity of 25.6 Ci/mmol. Standard assay conditions were modified from the published procedure to be identical to the PDE assay conditions, except for the last of the cAMP: 50 mM Tris HCl (pH 7.5), 5 mM $MgCl_2$, 50 μM 5'-AMP and 1 nM of [$^3$H]-rolipram (Torphy et al., J. of Biol. Chem., Vol. 267, No. 3 pp 1798-1804, 1992). The assay was run for 1 hour at 30° C. The reaction was terminated and bound ligand was separated from free ligand using a Brandel cell harvester. Competition for the high affinity binding site was assessed under conditions that were identical to those used for measuring low affinity PDE activity, expect that [$^3$H]-cAMP was not present.

Assay Method 1B

Measurement of Phosphodiesterase Activity

PDE activity was assayed using a [$^3$H]cAMP SPA or [$^3$H]cGMP SPA enzyme assay as described by the supplier (Amersham Life Sciences). The reactions were conducted in 96-well plates at room temperature, in 0.1 ml of reaction buffer containing (final concentrations): 50 mM Tris-HCl, pH 7.5, 8.3 mM $MgCl_2$, 1.7 mM EGTA, [$^3$H]cAMP or [$^3$H]cGMP (approximately 2000 dpm/pmol), enzyme and various concentrations of the inhibitors. The assay was allowed to proceed for 1 hr and was terminated by adding 50 μl of SPA yttrium silicate beads in the presence of zinc sulfate. The plates were shaken and allowed to stand at room temperature for 20 min. Radiolabeled product formation was assessed by scintillation spectrometry.

[$^3$H]R-rolipram Binding Assay

The [$^3$H]R-rolipram binding assay was performed by modification of the method of Schneider and co-workers, see Nicholson, et al., Trends Pharmacol. Sci., Vol. 12, pp. 19-27 (1991) and McHale et al., Mol. Pharmacol., Vol. 39, 109-113 (1991). R-Rolipram binds to the catalytic site of PDE4 see Torphy et al., Mol. Pharmacol., Vol. 39, pp. 376-384 (1991). Consequently, competition for [$^3$H]R-rolipram binding provides an independent confirmation of the PDE4 inhibitor potencies of unlabeled competitors. The assay was performed at 30° C. for 1 hr in 0.5 μl buffer containing (final concentrations): 50 mM Tris-HCl, pH 7.5, 5 mM $MgCl_2$, 0.05% bovine serum albumin, 2 nM [$^3$H]R-rolipram (5.7×104 dpm/pmol) and various concentrations of non-radiolabeled inhibitors.

The reaction was stopped by the addition of 2.5 ml of ice-cold reaction buffer (without [$^3$H]—R-rolipram) and rapid vacuum filtration (Brandel Cell Harvester) through Whatman GF/B filters that had been soaked in 0.3% polyethylenimine. The filters were washed with an additional 7.5 ml of cold buffer, dried, and counted via liquid scintillation spectrometry. The preferred PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM [$^3$H]-cAMP as the substrate.

Examples of useful PDE4 inhibitors are:

(R)-(+)-1-(4-bromobenzyl)-4-[(3-cyclopentyloxy)-4-methoxyphenyl]-2-pyrrolidone;

(R)-(+)-1-(4-bromobenzyl)-4-[(3-cyclopentyloxy)-4-methoxyphenyl]-2-pyrrolidone;

3-(cyclopentyloxy-4-methoxyphenyl)-1-(4-N'-[N2-cyano-5-methyl-isothioureido]benzyl)-2-pyrrolidone;

cis 4-cyano-4-(3-cyclopentyloxy-4-methoxyphenyl)cyclohexan-1-carboxylic acid];

cis-[4-cyano-4-(3-cyclopropylmethoxy-4-difluoromethoxyphenyl)cyclohexan-1-ol];

(R)-(+)-ethyl[4-(3-cyclopentyloxy-4-methoxyphenyl)pyrrolidine-2-ylidene]acetate; and (S)-(−)-ethyl[4-(3-cyclopentyloxy-4-methoxyphenyl)pyrrolidine-2-ylidene]acetate.

Most preferred are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl) cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an $IC_{50}$ ratio of 0.1 or greater.

Other compounds of interest include:

Compounds set out in U.S. Pat. No. 5,552,438 issued 03 Sep., 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms;

AWD-12-281 from Asta Medica (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*, 10bS*)-9-ethoxy-1,2,3,4,4a, 10b-hexahydro-8-methoxy-2-methylbenzo[c][1,6] naphthyridin-6-yl]-N,N-di isopropylbenzamide which is a mixed PDE3/PDE4 inhibitor which has been prepared and published on by Byk-Gulden, now Altana; arofylline under development by Almirall-Prodesfarma; VM554/UM565 from Vemalis; or T-440 (Tanabe Seiyaku; Fuji, K. et al. J Pharmacol Exp Ther, 1998, 284(1): 162), and T2585.

Other possible PDE-4 and mixed PDE3/PDE4 inhibitors include those listed in WO01/13953, the disclosure of which is hereby incorporated by reference.

Suitable anticholinergic agents are those compounds that act as antagonists at the muscarinic receptor, in particular those compounds which are antagonists of the $M_1$ and $M_2$ receptors.

Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6;

atropine oxide—CAS-4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, l)-CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt-CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-116), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, have a core structure, which can be represented by the following formula:

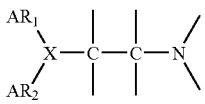

This generalized structure represents three types of antihistamines generally available: ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlropheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

Examples of preferred anti-histamines include methapyrilene and loratadine.

The invention thus provides, in a further aspect, a combination comprising a compound of formula (I) a pharmaceutically acceptable salt, solvate or physiologically functional derivative thereof together with a PDE4 inhibitor.

The invention thus provides, in a further aspect, a combination comprising a compound of formula (I) a pharmaceutically acceptable salt, solvate or physiologically functional derivative thereof together with a corticosteroid.

The invention thus provides, in a further aspect, a combination comprising a compound of formula (I) a pharmaceutically acceptable salt, solvate or physiologically functional derivative thereof together with an anticholinergic.

The invention thus provides, in a further aspect, a combination comprising a compound of formula (I) a pharmaceutically acceptable salt, solvate or physiologically functional derivative thereof together with an antihistamine.

The invention thus provides, in a further aspect, a combination comprising a compound of formula (I) a pharmaceutically acceptable salt, solvate or physiologically functional derivative thereof together with a PDE4 inhibitor and a corticosteroid.

The invention thus provides, in a further aspect, a combination comprising a compound of formula (I) a pharmaceutically acceptable salt, solvate or physiologically functional derivative thereof together with an anticholinergic and a PDE-4 inhibitor.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

According to a further aspect of the invention, there is provided a process for preparing a compound of formula (I), (Ia) or (Ib) or a salt, solvate, or physiologically functional derivative thereof which comprises a process (a) (b) (c) or (d) as defined below followed by the following steps in any order:

(i) optional removal of any protecting groups;
(ii) optional separation of an enantiomer from a mixture of enantiomers;
(iii) optional conversion of the product to a corresponding salt, solvate, or physiologically functional derivative thereof.

In one general process (a), a compound of formula (I), (Ia) or (Ib) may be obtained by deprotection of a protected intermediate, for example of formula (II):

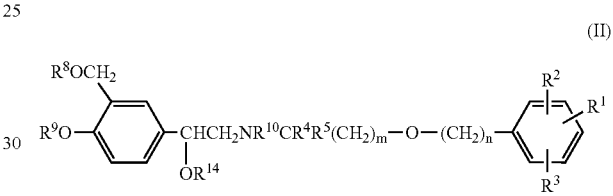

or a salt or solvate thereof, wherein $R^1$, $R^2$, $R^3$, $R^4$, $R^5$, m, and n are as defined for the compound of formula (I), (Ia) or (Ib), $R^8$, $R^9$, and $R^{10}$ are each independently either hydrogen or a protecting group provided that at least one of $R^8$, $R^9$, and $R^{10}$ is a protecting group, and $R^{14}$ is either hydrogen or a protecting group.

Suitable protecting groups may be any conventional protecting group such as those described in "Protective Groups in Organic Synthesis" by Theodora W Greene and Peter G M Wuts, 3rd edition (John Wiley & Sons, 1999). Examples of suitable hydroxyl protecting groups represented by $R^8$ and $R^9$ are esters such as acetate ester, aralkyl groups such as benzyl, diphenylmethyl, or triphenylmethyl, and tetrahydropyranyl. Examples of suitable amino protecting groups represented by $R^{10}$ include benzyl, α-methylbenzyl, diphenylmethyl, triphenylmethyl, benzyloxycarbonyl, tert-butoxycarbonyl, and acyl groups such as trichloroacetyl or trifluoroacetyl.

As will be appreciated by the person skilled in the art, use of such protecting groups may include orthogonal protection of groups in the compounds of formula (II) to facilitate the selective removal of one group in the presence of another, thus enabling selective functionalisation of a single amino or hydroxyl function. For example, the —CH(OH) group may be orthogonally protected as —CHOR$^{14}$ using, for example, a trialkylsilyl group such as triethylsilyl. A person skilled in the art will also appreciate other orthogonal protection strategies, available by conventional means as described in Theodora W Greene (see above).

The deprotection to yield a compound of formula (I), (Ia) or (Ib) may be effected using conventional techniques. Thus, for example, when $R^8$, $R^9$, and/or $R^{10}$ is an aralkyl group, this may be cleaved by hydrogenolysis in the presence of a metal catalyst (e.g. palladium on charcoal).

When $R^8$ and/or $R^9$ is tetrahydropyranyl this may be cleaved by hydrolysis under acidic conditions. Acyl groups represented by $R^{10}$ may be removed by hydrolysis, for example with a base such as sodium hydroxide, or a group such as trichloroethoxycarbonyl may be removed by reduction with, for example, zinc and acetic acid. Other deprotection methods may be found in Theodora W Greene (see above). In a particular embodiment of process (a), $R^8$ and $R^9$ may together represent a protecting group as in the compound of formula (III).

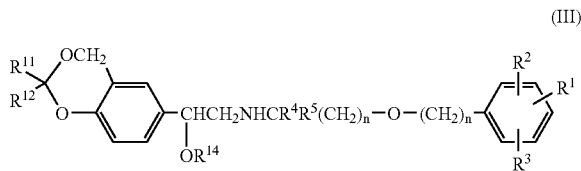

(III)

or a salt or solvate thereof, wherein $R^1$, $R^2$, $R^3$, $R^4$, $R^5$, $R^{14}$, m, and n are as defined for the compound of formula (I), (Ia) or (Ib), $R^{11}$ and $R^{12}$ are independently selected from hydrogen, $C_{1-6}$alkyl, or aryl. In a preferred aspect, both $R^{11}$ and $R^{12}$ are methyl.

A compound of formula (III) may be converted to a compound of formula (I), (Ia) or (Ib) by hydrolysis with dilute aqueous acid, for example acetic acid or hydrochloric acid in a suitable solvent or by transketalisation in an alcohol, for example ethanol, in the presence of a catalyst such as an acid (for example, toluenesulphonic acid) or a salt (such as pyridinium tosylate) at normal or elevated temperature.

It will be appreciated that the protecting groups $R^8$, $R^9$, $R^{10}$ and $R^{14}$ (including the cyclised protecting group formed by $R^8$ and $R^9$ as depicted in formula (III) may be removed in a single step or sequentially. The precise order in which protecting groups are removed will in part depend upon the nature of said groups and will be readily apparent to the skilled worker. Preferably, when $R^8$ and $R^9$ together form a protecting group as in formula (III) this protecting group is removed together with any protecting group on the CH(OH) moiety, followed by removal of $R^{10}$.

Compounds of formulae (II) and (III) wherein $R^{10}$ is hydrogen may be prepared from the corresponding compound of formula (IV):

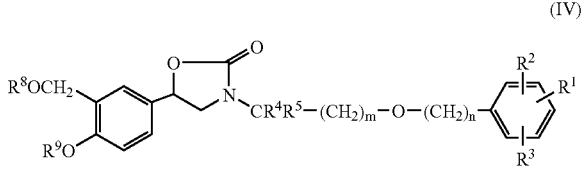

(IV)

or a salt or solvate thereof, wherein $R^1$, $R^2$, $R^3$, $R^4$, $R^5$, $R^8$, $R^9$ m, and n are as defined for the compound of formula (II) or (III).

The conversion of a compound of formula (IV) to a compound of formula (II) or (III) may be effected by treatment with a base, for example a non-aqueous base, such as potassium trimethylsilanoate, or an aqueous base such as aqueous sodium hydroxide, in a suitable solvent such as tetrahydrofuran.

Compounds of formula (IV) may be prepared from the corresponding compound of formula (V):

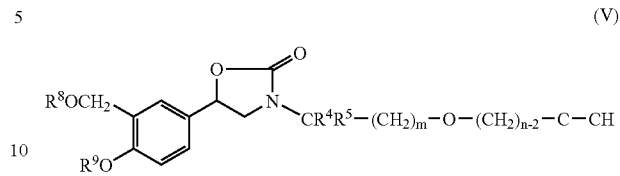

(V)

or a salt or solvate thereof, wherein $R^4$, $R^5$, $R^8$, $R^9$, m and n are as defined for the compound of formula (IV);

by coupling with a compound of formula (VI):

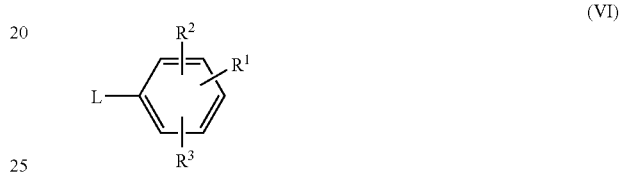

(VI)

wherein $R^1$, $R^2$, and $R^3$ are as defined for the compound of formula (IV) and L is a leaving group, such as a halo group (typically, bromo or iodo) or a sulphonate ester such as a haloalkyl sulphonate (typically, trifluoromethanesulphonate), followed by reduction.

The coupling of compound of formula (V) with a compound of formula (VI) is conveniently effected in the presence of a catalyst system such as bis(triphenylphosphine) palladium dichloride with an organic base such as a trialkylamine, for example, triethylamine, in a suitable solvent, for example acetonitrile or dimethylformamide. The resulting alkyne may then be reduced, either with or without being isolated to form the compound of formula (IV). The reduction may be effected by any suitable method such as hydrogenation in the presence of a catalyst, for example, palladium/charcoal or platinum oxide.

Alternatively, in the compounds of formula (VI) $R^1$, $R^2$, and $R^3$ may represent groups convertible into $R^1$, $R^2$, and $R^3$, for example halo groups. This is particularly useful where one of the groups $R^1$, $R^2$, and $R^3$ may be affected by any of the subsequent transformations. Thus, for example, where $R^1$ contains an alkenylene moiety, this is preferably introduced after the reduction of the alkyne formed by reaction of compounds (V) and (VI).

Compounds of formula (VI) are commercially available or may be prepared by methods well known to the person skilled in the art.

Compounds of formula (V) may be prepared by coupling a compound of formula (VII):

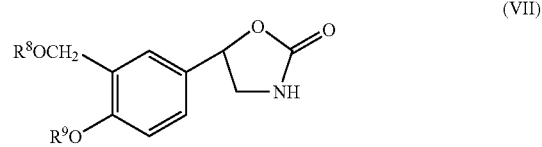

(VII)

or a salt or solvate thereof, wherein $R^8$ and $R^9$ are as defined for the compound of formula (V) with a compound of formula (VIII):

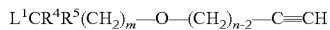

wherein $R^4$, $R^5$, m and n are as defined for the compound of formula (V) and $L^1$ is a leaving group, for example a halo group (typically bromo or iodo) or a sulphonate such as an alkyl sulphonate (typically, methanesulphonate), an arylsulphonate (typically, toluenesulphonate), or a haloalkyl sulphonate (typically, trifluoromethanesulphonate).

The coupling of a compound of formula (VII) with a compound of formula (VIII) may be effected in the presence of a base, such as a metal hydride, for example sodium hydride, or an inorganic base such as cesium carbonate, in an aprotic solvent, for example dimethylformamide.

Compounds of formula (VIII) may be prepared from the corresponding dihaloalkane and hydroxyalkyne by conventional chemistry, typically in the presence of an inorganic base, such as aqueous sodium hydroxide, under phase transfer conditions in the presence of a salt such as tetraalkylammonium bromide.

Compounds of formula (VII) may be prepared by ring closure of a compound of formula (IX):

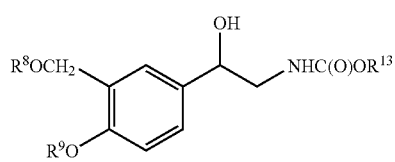

wherein $R^8$ and $R^9$ are as defined for the compound of formula (VII) and $R^{13}$ is $C_{1-6}$alkyl, for example tert-butyl, or aryl, for example phenyl. The ring closure may be effected by treatment with a base, such as a metal hydride, for example sodium hydride, in the presence of an aprotic solvent, for example, dimethylformamide.

Compounds of formula (IX) may be prepared from the corresponding ketone of formula (X):

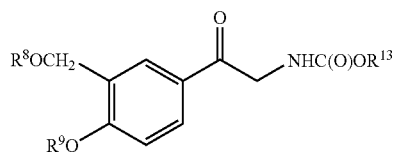

wherein $R^8$ and $R^9$ and $R^{13}$ are as defined for the compound of formula (IX), by reduction by any suitable method, for example by treatment with borane, in the presence of a chiral catalyst, such as CBS-oxazaborolidine, in a suitable solvent such as tetrahydrofuran.

The compound of formula (X) may be prepared from the corresponding halide of formula (XI)

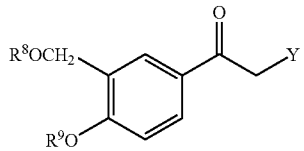

wherein $R^8$ and $R^9$ are as defined for the compound of formula (X) and Y is halo, suitably bromo.

The conversion of a compound of formula (XI) to a compound of formula (X) may be effected by reaction with the protected amine $HN(COOR^{13})_2$ wherein $R^{13}$ is as defined for the compound of formula (X) in the presence of an inorganic base such as cesium carbonate, followed by selective removal of one of the $COOR^{13}$ groups, for example by treatment with an acid such as trifluoroacetic acid.

Compounds of formula (XI) may be prepared from the corresponding compound having free hydroxymethyl and hydroxy substituents (which itself may be prepared from 2-bromo-1-(4-hydroxy)-3-hydroxymethyl-phenethyl)ethanone, the preparation of which is described in GB2140800, by treatment with 2-methoxypropane in acetone in the presence of an acid e.g. p-toluene-sulphonic acid in a nitrogen atmosphere or by other standard methods) by forming the protected groups $R^8OCH_2$— and $R^9O$— wherein $R^8$ and $R^9$ are as defined for the compound of formula (XI). Such methods are described in DE 3513885 (Glaxo).

Compounds of formula (II) or (III) wherein $R^{10}$ is a protecting group may be prepared as described in process (b) below, or by analogous methods to process (c) below.

In a further process (b), a compound of formula (I), (Ia) or (Ib) may be obtained by alkylation of an amine of formula (XII):

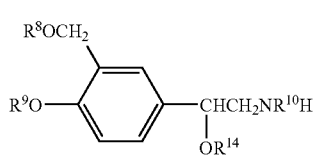

wherein $R^8$, $R^9$, $R^{10}$ and $R^{14}$ are each independently either hydrogen or a protecting group. Suitable protecting groups are discussed in the definition of compounds of formula (II); with a compound of formula (XIII):

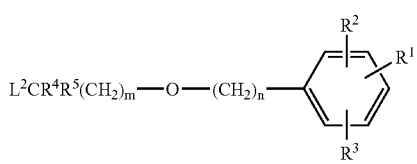

wherein $R^1$, $R^2$, $R^3$, $R^4$, $R^5$, m, and n are as defined for the compound of formula (I), (Ia) or (Ib) and $L^2$ is a leaving group such as halo (typically bromo); followed by removal of any protecting groups present by conventional methods as described above for the deprotection of compounds of formula (II).

The reaction of compounds of formulae (XII) and (XIII) is optionally effected in the presence of an organic base such as a trialkylamine, for example, diisopropylethylamine, and in a suitable solvent for example dimethyl formamide.

Compounds of formula (XII) are known in the art (for example EP-A 0947498) or may be readily prepared by a person skilled in the art.

Compounds of formula (XIII) may be prepared by coupling a compound of formula (VI) as defined above, or a precursor thereof (wherein one or more of the substituents $R^1$, $R^2$ or $R^3$ is a group which is convertible to the desired group $R^1$, $R^2$, or $R^3$) with a compound of formula (VIII) as shown above wherein $R^4$, $R^5$, m, and n are as defined for the compound of formula (XIII) and $L^1$ is a leaving group as defined above.

The coupling of a compound of formula (VIII) with a compound (VI) may be effected by methods analogous to those described above for coupling a compound of formula (V) with a compound of formula (VI), followed by reduction of the resulting alkyne of formula (XIV):

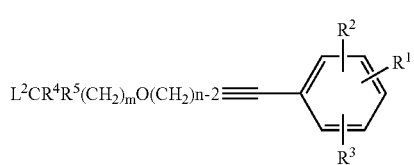

(XIV)

also as described above. If necessary, the substituents $R^1$, $R^2$, and/or $R^3$ may be formed by conventional conversions where a precursor is present.

An alkyne of formula (XIV) may also be prepared by reacting a compound of formula (XV):

$$L^2CR^4R^5(CH_2)m\ L^3 \quad (XV)$$

with a compound of formula (XVI):

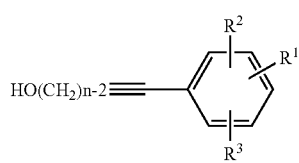

(XVI)

using conventional methods, for example as described for the preparation of compounds (VIII).

Compounds of formula (XVI) may be prepared by reacting a hydroxyalkyne

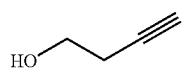

with a compound of formula (VI) using methods analogous to those described above for coupling a compound (V) with a compound (VI).

In a further process (c) a compound of formula (I), (Ia) or (Ib) may be prepared by reacting a compound of formula (XVII):

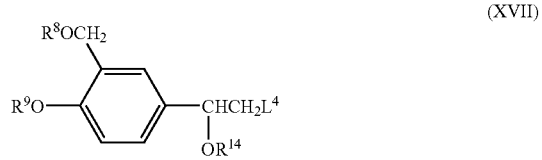

(XVII)

wherein $R^8$, $R^9$ and $R^{14}$ are as hereinbefore defined and $L^4$ is a leaving group, is reacted with an amine of formula (XVIII):

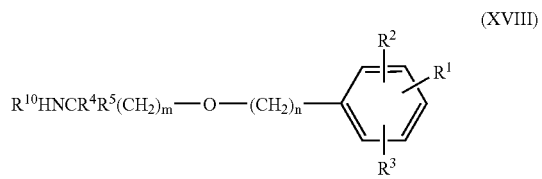

(XVIII)

followed by removal of any protecting groups present by conventional methods as described above for the deprotection of compounds of formula (II).

The reaction may be effected using conventional conditions for such displacement reactions.

Compounds of formula (XVII) may be prepared by methods known in the art.

Compounds of formula (XVIII) may be prepared by reacting a compound of formula (XIII) with an amine $R^{10}NH_2$.

In a further process (d) a compound of formula (I), (Ia) or (Ib) may be prepared by removal of a chiral auxiliary from a compound of formula (IIa):

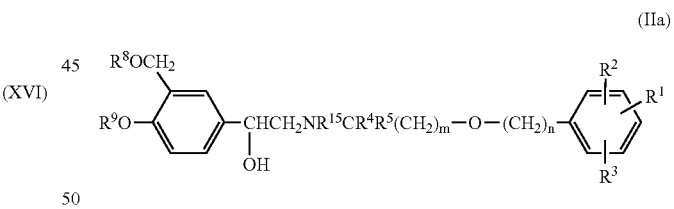

(IIa)

wherein $R^1$-$R^5$, $R^8$, $R^9$, m and n are as hereinbefore defined and $R^{15}$ represents a chiral auxiliary.

A "chiral auxiliary" is a moiety that is introduced into a molecule to influence the stereochemistry of the product formed, and is removed in whole or part at a later time. A chiral auxiliary may simultaneously function as a protecting group.

Many chiral auxiliaries are commercially available, and persons skilled in the art would choose one based on the properties desired i.e. the absolute stereochemistry desired and compatibility with the processes being used. Chiral auxiliaries suitable for use in this process include but are not limited to the S-isomer and/or the R-isomer of phenyl glycinol and substituted derivatives thereof.

The chiral auxiliary is preferably a moiety of the formula:

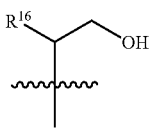

or a single enantiomer thereof, wherein $R^{16}$ represents $C_{1-6}$alkyl or optionally substituted phenyl or benzyl wherein the optional substitution is one or more independently selected from $C_{1-6}$alkyl, halogen, hydroxy, $C_{1-6}$alkoxy or nitro e.g. para-hydroxyphenyl.

More preferably the chiral auxiliary is a moiety:

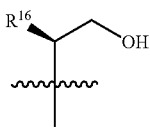

wherein $R^{16}$ is as defined above. Alternatively it may be a moiety of formula:

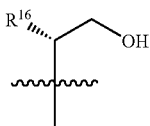

wherein $R^{16}$ is as defined above.

Preferably $R^{16}$ represents phenyl optionally substituted as described above, Most preferably R represents unsubstituted phenyl.

The chiral auxiliary in this process may typically be removed by hydrogenolysis using for example a palladium on carbon catalyst or preferably using palladium hydroxide (Pearlman's catalyst). Advantageously when Pearlman's catalyst is used the removal of the chiral auxiliary is most efficient. This method of removal is especially suitable where $R^1$ is phenyl or a substituted phenyl. Alternatively the nitrogen, to which the auxiliary is attached, may be derivatised under oxidising conditions to form the N-oxide before elimination by heating to give a secondary amine.

A compound of formula (IIa) may be prepared by reduction of the corresponding alkyne of formula (XIX):

Preferably in the compounds of formulae (IIa) and (XIX) the protecting groups $R^8$ and $R^9$ together form a group —$CR^{11}R^{12}$— as in the compounds of formula (III).

Reduction of an alkyne of formula (XIX) may be effected by methods well known in the art, for example by catalytic hydrogenation, using palladium on charcoal or more preferably palladium hydroxide (Pearlman's catalyst). The chiral auxiliary may also be removed under reductive conditions. Advantageously, therefore the reduction of the alkyne and removal of the chiral auxiliary may be effected concomitantly in a 'one-pot' reaction.

An alkyne of formula (XIX) may be prepared by reaction of a compound of formula (XX)

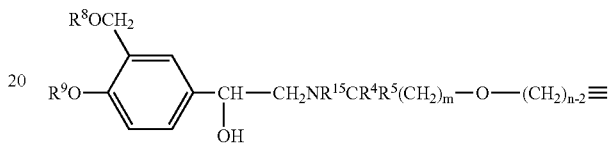

(XX)

with a compound of formula (VI) under conditions described above for coupling of compounds (V) and (VI).

A compound of formula (XX) may be prepared by reacting a compound of formula (XIIa):

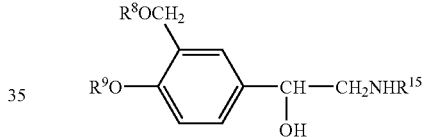

(XIIa)

with an aldehyde of formula (XXI):

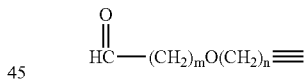

(XXI)

using known methods for effecting reductive amination, e.g. sodium triacetoxyborohydride in a solvent such as chloroform An aldehyde of formula (XXI) may be prepared from a corresponding halide of formula (VIII) using standard tech-

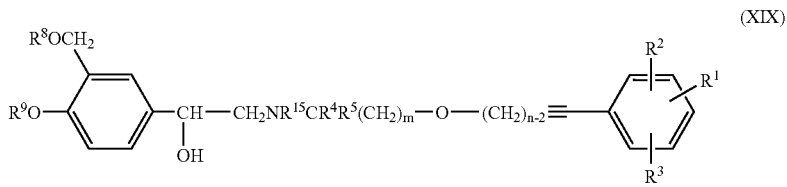

(XIX)

niques such as treatment with sodium bicarbonate in a solvent such as DMSO at elevated temperature, preferably in the range 130-160° C.

A compound of formula (XIIa) may be prepared from a compound of formula (XXII):

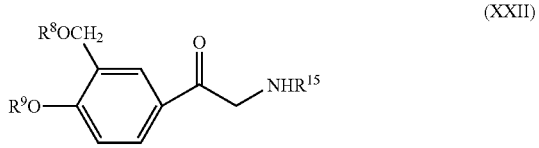

(XXII)

Wherein $R^8$, $R^9$ and $R^{15}$ are as hereinbefore defined by treatment with a reducing agent such as a hydride source e.g. sodium borohydride. Preferably this process takes place in the presence of an inert metal salt such as calcium chloride suitably at non-extreme temperatures e.g. below ambient, such as 0° C. This allows the desired stereochemistry to be introduced efficiently with good enantiomeric excess at an early stage in the synthesis, using inexpensive and relatively harmless reagents. Furthermore, the enantiomeric excess may be increased by recrystallisation of the product of this process.

A compound of formula (XXII) may be prepared from a compound of formula (XI) as hereinbefore defined by reaction with an appropriate chiral amine, e.g. (S)-phenylglycinol, in the presence of a non-nucleophilic base in an inert solvent at non-extreme temperatures.

A detailed description of a process analogous to Route (d) may be found in published International Application Number WO/0196278.

In the above process (d) it is preferred that the protecting groups $R^8$ and $R^9$ together form a protecting group as depicted in formula (III).

It will be appreciated that in any of the routes (a) to (d) described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

The enantiomeric compounds of the invention may be obtained (i) by separation of the components of the corresponding racemic mixture, for example, by means of a chiral chromatography column, enzymic resolution methods, or preparing and separating suitable diastereoisomers, or (ii) by direct synthesis from the appropriate chiral intermediates by the methods described above.

Optional conversions of a compound of formula (I), (Ia) or (Ib) to a corresponding salt may conveniently be effected by reaction with the appropriate acid or base. Optional conversion of a compound of formula (I), (Ia) or (Ib) to a corresponding solvate or physiologically functional derivative may be effected by methods known to those skilled in the art.

According to a further aspect, the present invention provides novel intermediates for the preparation of compounds of formula (I), (Ia) or (Ib), for example:

compounds of formula (II) and (III) as defined above, or an optical isomer, a salt, or a protected derivative thereof; particularly, a compound selected from:

3-{4-[(6-{[(2R)-2-(2,2-Dimethyl-4H-1,3-benzodioxin-6-yl)-2-hydroxyethyl]amino}hexyl)oxy]butyl}benzenesulfonamide;

4-{4-[(6-{[(2R)-2-(2,2-Dimethyl-4H-1,3-benzodioxin-6-yl)-2-hydroxyethyl]amino}hexyl)oxy]butyl}benzenesulfonamide;

2-{4-[(6-{[(2R)-2-(2,2-Dimethyl-4H-1,3-benzodioxin-6-yl)-2-hydroxyethyl]amino}hexyl)oxy]butyl}benzenesulfonamide;

3-{4-[(6-{[(2R)-2-(2,2-Dimethyl-4H-1,3-benzodioxin-6-yl)-2-hydroxyethyl]amino}hexyl)oxy]butyl}-N-methylbenzenesulfonamide;

(1R)-1-(2,2-Dimethyl-4H-1,3-benzodioxin-6-yl)-2-[(6-{4-[3-(morpholin-4-ylsulfonyl)phenyl]butoxy}hexyl)amino]ethanol;

3-{4-[(6-{[(2R)-2-(2,2-Dimethyl-4H-1,3-benzodioxin-6-yl)-2-hydroxyethyl]amino}hexyl)oxy]butyl}-N,N-dimethylbenzenesulfonamide;

3-{4-[(6-{[(2R)-2-(2,2-Dimethyl-4H-1,3-benzodioxin-6-yl)-2-hydroxyethyl]amino}hexyl)oxy]butyl}-N-isopropylbenzenesulfonamide;

N-(tert-Butyl)-3-{4-[(6-{[(2R)-2-(2,2-dimethyl-4H-1,3-benzodioxin-6-yl)-2-hydroxyethyl]amino}hexyl)oxy]butyl}benzenesulfonamide; and (1R)-1-(2,2-Dimethyl-4H-1,3-benzodioxin-6-yl)-2-[(6-{4-[3-(piperidin-1-ylsulfonyl)phenyl]butoxy}hexyl)amino]ethanol;

(1R)-1-(2,2-Dimethyl-4H-1,3-benzodioxin-6-yl)-2-[(6-{4-[3-(piperazin-1-ylsulfonyl)phenyl]butoxy}hexyl)amino]ethanol;

3-{4-[(6-{[(2R)-2-(2,2-Dimethyl-4H-1,3-benzodioxin-6-yl)-2-hydroxyethyl]-amino}hexyl)oxy]butyl}-N-(1-methyl-1-phenylethyl)benzenesulfonamide;

N-[4-(Aminosulfonyl)phenyl]-3-{4-[(6-{[(2R)-2-(2,2-dimethyl-4H-1,3-benzodioxin-6-yl)-2-hydroxyethyl]amino}hexyl)oxy]butyl}benzenesulfonamide;

{3-{4-[(6-{[(2R)-2-(2,2-Dimethyl-4-H-1,3-benzodioxin-6-yl)-2-hydroxyethyl]-amino}hexyl)oxy]butyl}phenyl}methanesulfonamide;

5-{4-[(6-{[(2R)-2-(2,2-Dimethyl-4H-1,3-benzodioxin-6-yl)-2-hydroxyethyl]amino}hexyl)oxy]butyl}-2-methoxybenzenesulfonamide;

3-{5-[(5-{[(2R)-2-(2,2-Dimethyl-4H-1,3-benzodioxin-6-yl)-2-hydroxyethyl]-amino}pentyl)oxy]pentyl}benzenesulfonamide;

3-{3-[(7-{[(2R)-2-(2,2-Dimethyl-4H-1,3-benzodioxin-6-yl)-2-hydroxyethyl]-amino}heptyl)oxy]propyl}benzenesulfonamide;

3-[6-(4-{[(2R)-2-(2,2-Dimethyl-4H-1,3-benzodioxin-6-yl)-2-hydroxyethyl]-amino}butoxy)hexyl]benzenesulfonamide;

3-{3-[(6-{[(2R)-2-(2,2-Dimethyl-4H-1,3-benzodioxin-6-yl)-2-hydroxyethyl]amino}hexyl)oxy]propyl}benzenesulfonamide;

3-{4-[(5-{[(2R)-2-(2,2-Dimethyl-4H-1,3-benzodioxin-6-yl)-2-hydroxyethyl]amino}pentyl)oxy]butyl}benzenesulfonamide;

N-[3-(Aminosulfonyl)phenyl]-3-{4-[(6-{[(2R)-2-(2,2-dimethyl-4H-1,3-benzodioxin-6-yl)-2-hydroxyethyl]amino}hexyl)oxy]butyl}benzenesulfonamide;

N-Benzyl-3-{4-[(6-{[(2R)-2-(2,2-dimethyl-4H-1,3-benzodioxin-6-yl)-2-hydroxyethyl]amino}hexyl)oxy]butyl}benzenesulfonamide;

3-{4-[(6-{[2-(2,2-Dimethyl-4H-1,3-benzodioxin-6-yl)-2-hydroxyethyl]amino}hexyl)oxy]butyl}benzenesulfonamide;

3-{4-[(6-{[(2S)-(2,2-Dimethyl-4H-1,3-benzodioxin-6-yl)-2-hydroxyethyl]amino}hexyl)oxy]butyl}benzenesulfonamide;

N-(4-{[(3-{4-[(6-{[(2R)-2-(2,2-Dimethyl-4H-1,3-benzodioxin-6-yl)-2-hydroxyethyl]amino}hexyl)oxy]butyl}phenyl)sulfonyl]amino}phenyl)acetamide;

N-Cyclobutyl-3-{4-[(6-{[(2R)-2-(2,2-dimethyl-4H-1,3-benzodioxin-6-yl)-2-hydroxyethyl]amino}hexyl)oxy]butyl}benzenesulfonamide;

N-Cyclohexyl-3-{4-[(6-{[(2R)-2-(2,2-dimethyl-4H-1,3-benzodioxin-6-yl)-2-hydroxyethyl]amino}hexyl)oxy]butyl}benzenesulfonamide;

3-{4-[(6-{[(2R)-2-(2,2-Dimethyl-4H-1,3-benzodioxin-6-yl)-2-hydroxyethyl]amino}hexyl)oxy]butyl}-N-(4-fluorophenyl)benzenesulfonamide;

3-{4-[(6-{[(2R)-2-(2,2-Dimethyl-4H-1,3-benzodioxin-6-yl)-2-hydroxyethyl]amino}-hexyl)oxy]butyl}-N-(2-morpholin-4-ylethyl)benzenesulfonamide;

(E)-2-(3-{4-[(6-{[(2R)-2-(2,2-Dimethyl-4H-1,3-benzodioxin-6-yl)-2-hydroxyethyl]amino}hexyl)oxy]butyl}phenyl)-N-methylethenesulfonamide;

(E)-2-(3-{4-[(6-{[(2R)-2-(2,2-Dimethyl-4H-1,3-benzodioxin-6-yl)-2-hydroxyethyl]amino}hexyl)oxy]butyl}phenyl)ethenesulfonamide;

5-{4-[(6-{[(2R)-2-(2,2-Dimethyl-4H-1,3-benzodioxin-6-yl)-2-hydroxyethyl]amino}hexyl)oxy]butyl}[1,1'-biphenyl]-3-sulfonamide;

3-{4-[(6-{[(2R)-2-(2,2-Dimethyl-4H-1,3-benzodioxin-6-yl)-2-hydroxyethyl]amino}hexyl)oxy]butyl}-5-pentylbenzenesulfonamide;

compounds of formula (IV) as defined above, or an optical isomer, a salt, or a protected derivative thereof; particularly, a compound selected from:

3-[4-({6-[(5R)-5-(2,2-Dimethyl-4H-1,3-benzodioxin-6-yl)-2-oxo-1,3-oxazolidin-3-yl]hexyl}oxy)butyl]benzenesulfonamide;

N-[4-(Aminosulfonyl)phenyl]-3-[4-({6-[(5R)-5-(2,2-dimethyl-4H-1,3-benzodioxin-6-yl)-2-oxo-1,3-oxazolidin-3-yl]hexyl}oxy)butyl]benzenesulfonamide;

3-[4-({6-[(5R)-5-(2,2-dimethyl-4H-1,3-benzodioxin-6-yl)-2-oxo-1,3-oxazolidin-3-yl]hexyl}oxy)butyl]-N-(4-fluorophenyl)benzenesulfonamide;

3-[4-({6-[(5R)-5-(2,2-Dimethyl-4H-1,3-benzodioxin-6-yl)-2-oxo-1,3-oxazolidin-3-yl]hexyl}oxy)butyl]-N-(2-morpholin-4-ylethyl)benzenesulfonamide;

N-Cyclohexyl-3-[4-({6-[(5R)-5-(2,2-dimethyl-4H-1,3-benzodioxin-6-yl)-2-oxo-1,3-oxazolidin-3-yl]hexyl}oxy)butyl]benzenesulfonamide;

4-[4-({6-[(5R)-5-(2,2-Dimethyl-4H-1,3-benzodioxin-6-yl)-2-oxo-1,3-oxazolidin-3-yl]hexyl}oxy)butyl]benzenesulfonamide;

2-[4-({6-[(5R)-5-(2,2-Dimethyl-4H-1,3-benzodioxin-6-yl)-2-oxo-1,3-oxazolidin-3-yl]hexyl}oxy)butyl]benzenesulfonamide;

(5R)-5-(2,2-Dimethyl-4H-1,3-benzodioxin-6-yl)-3-(6-{4-[3-(piperazin-1-ylsulfonyl)phenyl]butoxy}hexyl)-1,3-oxazolidin-2-one;

3-[4-({6-[(5R)-5-(2,2-Dimethyl-4H-1,3-benzodioxin-6-yl)-2-oxo-1,3-oxazolidin-3-yl]hexyl}oxy)butyl]-N-(1-methyl-1-phenylethyl)benzenesulfonamide;

3-[4-({6-[(5R)-5-(2,2-Dimethyl-4H-1,3-benzodioxin-6-yl)-2-oxo-1,3-oxazolidin-3-yl]hexyl}oxy)butyl]-N-methylbenzenesulfonamide;

(5R)-5-(2,2-Dimethyl-4H-1,3-benzodioxin-6-yl)-3-(6-{4-[3-(morpholin-4-ylsulfonyl)phenyl]butoxy}hexyl)-1,3-oxazolidin-2-one;

3-[4-({6-[(5R)-5-(2,2-Dimethyl-4H-1,3-benzodioxin-6-yl)-2-oxo-1,3-oxazolidin-3-yl]hexyl}oxy)butyl]-N,N-dimethylbenzenesulfonamide;

3-[4-({6-[(5R)-5-(2,2-Dimethyl-4H-1,3-benzodioxin-6-yl)-2-oxo-1,3-oxazolidin-3-yl]hexyl}oxy)butyl]-N-isopropylbenzenesulfonamide;

N-(tert-Butyl)-3-[4-({6-[(5R)-5-(2,2-dimethyl-4H-1,3-benzodioxin-6-yl)-2-oxo-1,3-oxazolidin-3-yl]hexyl}oxy)butyl]benzenesulfonamide;

(5R)-5-(2,2-Dimethyl-4H-1,3-benzodioxin-6-yl)-3-(6-{4-[3-(piperidin-1-ylsulfonyl)phenyl]butoxy}hexyl)-1,3-oxazolidin-2-one;

3-[4-({6-[(5R)-5-(2,2-Dimethyl-4H-1,3-benzodioxin-6-yl)-2-oxo-1,3-oxazolidin-3-yl]hexyl}oxy)butyl]phenylmethanesulfonamide;

3-[5-({5-[(5R)-5-(2,2-Dimethyl-4H-1,3-benzodioxin-6-yl)-2-oxo-1,3-oxazolidin-3-yl]pentyl}oxy)pentyl]benzenesulfonamide;

5-[4-({6-[(5R)-5-(2,2-Dimethyl-4H-1,3-benzodioxin-6-yl)-2-oxo-1,3-oxazolidin-3-yl]hexyl}oxy)butyl]-2-methoxybenzenesulfonamide;

3-[3-({7-[(5R)-5-(2,2-Dimethyl-4H-1,3-benzodioxin-6-yl)-2-oxo-1,3-oxazolidin-3-yl]heptyl}oxy)propyl]benzenesulfonamide;

3-(6-{4-[(5R)-5-(2,2-Dimethyl-4H-1,3-benzodioxin-6-yl)-2-oxo-1,3-oxazolidin-3-yl]butoxy}hexyl)benzenesulfonamide;

4-{3-[4-({6-[(5R)-5-(2,2-Dimethyl-4H-1,3-benzodioxin-6-yl)-2-oxo-1,3-oxazolidin-3-yl]hexyl}oxy)butyl]phenyl}butane-1-sulfonamide;

3-[5-({6-[(5R)-5-(2,2-Dimethyl-4H-1,3-benzodioxin-6-yl)-2-oxo-1,3-oxazolidin-3-yl]hexyl}oxy)pentyl]benzenesulfonamide;

3-[6-({6-[(5R)-5-(2,2-Dimethyl-4H-1,3-benzodioxin-6-yl)-2-oxo-1,3-oxazolidin-3-yl]hexyl}oxy)hexyl]benzenesulfonamide;

3-[3-({6-[(5R)-5-(2,2-Dimethyl-4H-1,3-benzodioxin-6-yl)-2-oxo-1,3-oxazolidin-3-yl]hexyl}oxy)propyl]benzenesulfonamide;

3-[4-({5-[(5R)-5-(2,2-Dimethyl-4H-1,3-benzodioxin-6-yl)-2-oxo-1,3-oxazolidin-3-yl]pentyl}oxy)butyl]benzenesulfonamide;

N-[3-(Aminosulfonyl)phenyl]-3-[4-({6-[(5R)-5-(2,2-dimethyl-4H-1,3-benzodioxin-6-yl)-2-oxo-1,3-oxazolidin-3-yl]hexyl}oxy)butyl]benzenesulfonamide;

N-Benzyl-3-[4-({6-[(5R)-5-(2,2-dimethyl-4H-1,3-benzodioxin-6-yl)-2-oxo-1,3-oxazolidin-3-yl]hexyl}oxy)butyl]benzenesulfonamide;

3-[4-({6-[(5R)-5-(2,2-Dimethyl-4H-1,3-benzodioxin-6-yl)-2-oxo-1,3-oxazolidin-3-yl]hexyl}oxy)butyl]-N-[(ethylamino)carbonyl]benzenesulfonamide;

3-[4-({6-[5-(2,2-Dimethyl-4H-1,3-benzodioxin-6-yl)-2-oxo-1,3-oxazolidin-3-yl]hexyl}oxy)butyl]benzenesulfonamide;

N-{4-[({3-[4-({6-[(5R)-5-(2,2-Dimethyl-4H-1,3-benzodioxin-6-yl)-2-oxo-1,3-oxazolidin-3-yl]hexyl}oxy)butyl]phenyl}sulfonyl)amino]phenyl}acetamide;

N-Cyclobutyl-3-[4-({6-[(5R)-5-(2,2-dimethyl-4H-1,3-benzodioxin-6-yl)-2-oxo-1,3-oxazolidin-3-yl]hexyl}oxy)butyl]benzenesulfonamide;

3-[4-({6-[(5R)-5-(2,2-Dimethyl-4H-1,3-benzodioxin-6-yl)-2-oxo-1,3-oxazolidin-3-yl]hexyl}oxy)butyl]-N-[2-(2-hydroxyethoxy)ethyl]benzenesulfonamide;

(E)-2-{3-[4-({6-[(5R)-5-(2,2-Dimethyl-4H-1,3-benzodioxin-6-yl)-2-oxo-1,3-oxazolidin-3-yl]hexyl}oxy)butyl]phenyl}-N-methylethenesulfonamide;

(E)-2-{3-[4-({6-[(5R)-5-(2,2-Dimethyl-4H-1,3-benzodioxin-6-yl)-2-oxo-1,3-oxazolidin-3-yl]hexyl}oxy)butyl]phenyl}ethenesulfonamide;

3-[((tert-Butoxycarbonyl) {[2-(trimethylsilyl)ethoxy]methyl}amino)sulfonyl]-5-[4-({6-[(5R)-5-(2,2-dimethyl-4H-1,3-benzodioxin-6-yl)-2-oxo-1,3-oxazolidin-3-yl]hexyl}oxy)butyl]-1,1'-biphenyl;

tert-Butyl {3-[4-({6-[(5R)-5-(2,2-dimethyl-4H-1,3-benzodioxin-6-yl)-2-oxo-1,3-oxazolidin-3-yl]hexyl}oxy)butyl]-5-pentylphenyl}sulfonyl {[2-(trimethylsilyl)ethoxy]methyl}carbamate;

1-{4-[4-({6-[(5R)-5-(2,2-Dimethyl-4H-1,3-benzodioxin-6-yl)-2-oxo-1,3-oxazolidin-3-yl]hexyl}oxy)butyl]phenyl}methanesulfonamide; and 1-{2-[4-({6-[(5R)-5-(2,2-Dimethyl-4H-1,3-benzodioxin-6-yl)-2-oxo-1,3-oxazolidin-3-yl]hexyl}oxy)butyl]phenyl}methanesulfonamide.

For a better understanding of the invention, the following Examples are given by way of illustration.

SYNTHETIC EXAMPLES

Throughout the examples, the following abbreviations are used:

LC: Liquid Chromatography
LCMS: Liquid Chromatography Mass Spectrometry.
RT: retention time
THF: tetrahydofuran
DMF: N,N-dimethylformamide
bp: boiling point
ca: circa
h: hour(s)
min: minute(s)
XRPD: X-ray powder diffraction
All temperatures are given in degrees centigrade.
Silica gel refers to Merck silica gel 60 Art number 7734.
Flash silica gel refers to Merck silica gel 60 Art number 9385.
Biotage refers to prepacked silica gel cartridges containing KP-Sil run on flash 12i chromatography module.
Bond Elut are prepacked cartridges used in parallel purifications, normally under vacuum. These are commercially available from Varian.
LC was conducted on a Luna C18(2) column (5 cm×2.0 mm ID) eluting with 0.05% v/v trifluoroacetic acid in water (solvent A) and 0.05% v/v trifluoroacetic acid in acetonitrile (solvent B) using the following elution gradient 0.00-8.00 min 0% B, 8.00-8.01 min 95% B, 8.01-10.00 min 0% B at a flow rate of 1.0 ml/min with a column temperature of 40° C.
NMR experiments at 400 MHz (unless specified otherwise).
LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0-0.7 min 0% B, 0.7-4.2 min 100% B, 4.2-5.3 min 0% B, 5.3-5.5 min 0% B at a flow rate of 3 ml/min. The mass spectra were recorded on a Fisons VG Platform spectrometer using electrospray positive and negative mode (ES+ve and ES−ve).
The XRPD analysis shown in the Figures were performed on a Phillips X'pert Pro powder diffractometer, Model PW3040/60, serial number DY1379. The method runs from 2 to 45 degrees 2Theta with 0.02 degree 2Theta step size and a 2 second collection time at each step.

Example 1

3-(4-{[6-({(2R)-2-Hydroxy-2-[4-hydroxy-3-(hydroxymethyl)phenyl]ethyl}amino)-hexyl]oxy}butyl)benzenesulfonamide acetate i) Di(tert-butyl) 2-(2,2-dimethyl-4H-1,3-benzodioxin-6-yl)-2-oxoethylimidodicarbonate Cesium carbonate (70.4 g) was added to a stirred suspension of 2-bromo-1-(2,2-dimethyl-4H-1,3-benzodioxin-6-yl)ethanone, (Glaxo, DE 3513885, 1985) (61.8 g) and di-t-butyl iminodicarboxylate (47.15 g) in acetonitrile (600 ml) under nitrogen. After vigorous stirring at 21° for 24 h the mixture was diluted with water (ca800 ml) and the product was extracted with diethyl ether (1 litre, then 200 ml). The combined organic layers were washed with brine, dried ($MgSO_4$) and concentrated to ca400 ml. The white crystals were collected by filtration, washed with diethyl ether and dried to give the title compound (24.4 g) δ ($CDCl_3$) 7.78(1H, dd, J 8, 2 Hz), 7.65 (1H, brs), 6.87(1H, d, J 8 Hz), 4.97(2H, s), 4.88(2H, s), 1.56(6H, s) and 1.48 (18H, s). Further concentration of the mother liquors gave additional product (13.8 g). A third crop (7.1 g) was obtained by chromatographing the mother liquors on silica gel, evaporating the appropriate eluate and triturating with diethyl ether.

ii) tert-Butyl 2-(2,2-dimethyl-4H-1,3-benzodioxin-6-yl)-2-oxoethylcarbamate

Trifluoroacetic acid (92 ml) was added to a stirred solution of di(tert-butyl) 2-(2,2-dimethyl-4H-1,3-benzodioxin-6-yl)-2-oxoethylimidodicarbonate, (352.55 g) in dichloromethane (3.6 litres) at 21° and the reaction was stirred for 1.5 h. Aqueous NaOH solution (1.75 litres) was added and after 10 min the phases were separated. The organic layer was washed with water, dried ($MgSO_4$) and evaporated to an oil. This was stored under high vacuum overnight and then triturated with hexane:ether (3:1) to give the crude product (226.61 g). This was purified by recrystallisation from diethyl ether to give the title compound (122.78 g). Further product (61.5 g) was obtained from the mother liquors by evaporation and chromatography on a Biotage using 15% ethyl acetate in hexane. LCMS RT=3.37 min.

iii) tert-Butyl (2R)-2-(2,2-dimethyl-4H-1,3-benzodioxin-6-yl)-2-hydroxyethylcarbamate A 2M solution of borane-dimethyl sulphide in THF (28 ml) was added slowly to a 1M solution of (R)-tetrahydro-1-methyl-3,3-diphenyl-1H,3H-pyrrolo[1,2-c][1,3,2]oxazaborole in toluene (56 ml) at 0° under nitrogen. A solution of tert-butyl 2-(2,2-dimethyl-4H-1,3-benzodioxin-6-yl)-2-oxoethylcarbamate, (108.2 g) in THF (1.3 litres) was added slowly keeping the temperature below 5° followed by 2M solution of borane-dimethyl sulphide in THF (252 ml) over 50 min. After 1 h, 2M HCl (170 ml) was added with cooling and the mixture was partitioned between ethyl acetate and water. The organic layer was washed with saturated $NaHCO_3$ solution and brine and dried ($MgSO_4$). The solution was concentrated and the product purified by chromatography on flash silica gel (800 g), eluting successively with hexane:ethyl acetate (4:1 then 3:1) to give the title compound (93.3 g), LCMS RT=3.31 min.

iv) (5R)-5-(2,2-Dimethyl-4H-1,3-benzodioxin-6-yl)-1,3-oxazolidin-2-one tert-Butyl (2R)-2-(2,2-dimethyl-4H-1,3-benzodioxin-6-yl)-2-hydroxyethylcarbamate, (86.37 g) in DMF (600 ml) was added dropwise to a stirred suspension of sodium hydride (60% oil dispersion, 11.9 g) in DMF (160 ml) with cooling such that the internal temperature remained at 0° under nitrogen. The mixture was stirred at 21° for 2 h. The mixture was recooled to 0° and 2M HCl (134 ml) was added. The mixture was diluted with water and the product was extracted with ethyl acetate twice. The solution was washed with brine twice, dried ($MgSO_4$) and evaporated to give the title compound (63.55 g) LCMS RT=2.66 min.

v) 6-Bromohexyl but-3-ynyl ether

3-Butyn-1-ol (42.4 ml) was stirred vigorously with 1,6-dibromohexane (260 ml) and tetrabutylammonium bisulphate (2.4 g) in 50% aqueous sodium hydroxide solution (200 ml) under nitrogen for 3 days. Water (ca 700 ml) was added and the organic layer was separated.

The aqueous layer was extracted twice with dichloromethane (2×100 ml) and the combined organic layers were washed with water, dried ($MgSO_4$) and concentrated. The residue in petroleum ether (bp 40-60°) was loaded onto a column of silica gel (1.5 kg) and the column was eluted with petroleum ether (bp 40-600), then 10% diethyl ether in petroleum ether (bp 40-60°) to give the title compound (103.3 g), δ ($CDCl_3$) 3.56(2H, t, J 7 Hz), 3.47(2H, t, J 7 Hz), 3.42(2H, t, J 7 Hz), 2.45(2H, m), 1.99(1H, t, J 2 Hz), 1.87(2H, m), 1.60(2H, m) and 1.50 to 1.33 (4H, m).

vi) (5R)-3-[6-(But-3-ynyloxy)hexyl]-5-(2,2-dimethyl-4H-1,3-benzodioxin-6-yl)-1,3-oxazolidin-2-one (5R)-5-(2,2-dimethyl-4H-1,3-benzodioxin-6-yl)-1,3-oxazolidin-2-one (10 g) in DMF (100 ml) was added dropwise to a stirred suspension of sodium hydride (60% oil dispersion, 2.33 g) in DMF (50 ml) with stirring under nitrogen and maintaining the internal temperature at 0°. Stirring was continued at 0-5° for 1 h. The mixture was recooled to 0° and a solution of 6-bromohexyl but-3-ynyl ether (14.7 g) in DMF (50 ml) was added over 1 min. The mixture was then stirred at 20-30° for 2 h. 2M HCl (9 ml) was added and the mixture was partitioned between water and diethyl ether. The aqueous layer was extracted with more diethyl ether and the combined organic layers were washed twice with brine. After drying ($MgSO_4$) the solution was concentrated and loaded onto a column of silica gel (600 g) set up in diethyl ether:petroleum ether (bp 40-60°) (1:2). The column was eluted successively with this mixture, then (1:1) and then diethyl ether to give the title compound (13.88 g) LCMS RT=3.45 min.

vii) 3-[4-({6-[(5R)-5-(2,2-Dimethyl-4H-1,3-benzodioxin-6-yl)-2-oxo-1,3-oxazolidin-3-yl]hexyl}oxy)but-1-ynyl]benzenesulfonamide (5R)-3-[6-(But-3-ynyloxy)hexyl]-5-(2,2-dimethyl-4H-1,3-benzodioxin-6-yl)-1,3-oxazolidin-2-one (1.79 g) was stirred with 3-iodobenzene sulphonamide (1.4 g) in acetonitrile:triethylamine (1:1, 42 ml) under nitrogen for 10 min. Cuprous iodide (0.083 g) and dichlorobis(triphenylphosphine)palladium (0.192 g) were added and the mixture was stirred for 17 h under nitrogen at 21°. The mixture was evaporated to dryness and the residue was chromatographed on silica gel (250 g) in 30% ethyl acetate:petroleum ether (bp 40-60°), then 50%, then 75% and finally ethyl acetate to give the title compound (2.35 g), LCMS RT=3.44 min.

viii) 3-[4-({6-[(5R)-5-(2,2-Dimethyl-4H-1,3-benzodioxin-6-yl)-2-oxo-1,3-oxazolidin-3-yl]hexyl}oxy)butyl]benzenesulfonamide 3-[4-({6-[(5R)-5-(2,2-Dimethyl-4H-1,3-benzodioxin-6-yl)-2-oxo-1,3-oxazolidin-3-yl]hexyl}oxy)but-1-ynyl]benzenesulfonamide (2.35 g) was stirred with platinum oxide (0.3 g) in THF (30 ml) under hydrogen for 2 h. The catalyst was removed by filtration using a filter aid and the filter cake was leached with ethyl acetate. The combined filtrates were passed through silica gel (200 g) in ethyl acetate and the eluate was evaporated to give the title compound (2.32 g), LCMS RT=3.49 min.

ix) 3-{4-[(6-{[(2R)-2-(2,2-Dimethyl-4H-1,3-benzodioxin-6-yl)-2-hydroxyethyl]amino}hexyl)oxy]butyl}benzenesulfonamide 3-[4-({6-[(5R)-5-(2,2-Dimethyl-4H-1,3-benzodioxin-6-yl)-2-oxo-1,3-oxazolidin-3-yl]hexyl}oxy)butyl]benzenesulfonamide (0.43 g) was stirred in THF (10 ml) while purging with a vigorous stream of nitrogen for 5 min. Potassium trimethylsilanoate (0.43 g) was added and the mixture was stirred at 70° under nitrogen for 2.5 h. The mixture was partitioned between dichloromethane and pH 6.4 phosphate buffer and the aqueous layer was extracted with more dichloromethane. The combined organic layers were washed with water, dried ($MgSO_4$) and concentrated. The residue was purified on silica gel (60 g), eluting successively with ethyl acetate:petroleum ether (bp 40-60°) (1:1), ethyl acetate, 10% then 20% methanol in ethyl acetate to give the title compound (0.286 g), LCMS RT=2.56 min.

x) 3-(4-{[6-({(2R)-2-Hydroxy-2-[4-hydroxy-3-(hydroxymethyl)phenyl]ethyl}amino)hexyl]oxy}butyl)benzenesulfonamide acetate 3-{4-[(6-{[(2R)-2-(2,2-dimethyl-4H-1,3-benzodioxin-6-yl)-2-hydroxyethyl]amino}hexyl)oxy]butyl}benzenesulfonamide (0.283 g) was stirred with acetic acid (8 ml) and water (4 ml) at 70° for 35 min before evaporating to dryness. The residue was re-evaporated twice with toluene to give the title compound (0.318 g) LCMS RT=2.34 min ES+ve 495 (MH)⁺.

Example 2

4-(4-{[6-({(2R)-2-Hydroxy-2-[4-hydroxy-3-(hydroxymethyl)phenyl]ethyl}amino)hexyl]oxy}butyl)benzenesulfonamide acetate i) 4-[4-({6-[(5R)-5-(2,2-Dimethyl-4H-1,3-benzodioxin-6-yl)-2-oxo-1,3-oxazolidin-3-yl]hexyl}oxy)but-1-ynyl]benzenesulfonamide was prepared using methods similar to those described in Example 1 vii.
LCMS RT=3.47 min.

ii) 4-[4-({6-[(5R)-5-(2,2-Dimethyl-4H-1,3-benzodioxin-6-yl)-2-oxo-1,3-oxazolidin-3-yl]hexyl oxy)butyl]benzenesulfonamide was prepared using methods similar to those described in Example 1 viii. LCMS RT=3.47 min.

iii) 4-{4-[(6-{[(2R)-2-(2,2-Dimethyl-4H-1,3-benzo-dioxin-6-yl)-2-hydroxyethyl]amino}hexyl)oxy]butyl}benzenesulfonamide was prepared using methods similar to those described in Example 1 ix.
LCMS RT=2.65 min.

iv) 4-(4-{[6-({(2R)-2-Hydroxy-2-[4-hydroxy-3-(hydroxymethyl)phenyl]ethyl}amino)hexyl]oxy}butyl)benzenesulfonamide acetate was prepared using methods similar to those described in Example 1 x.
LCMS RT=2.38 min, ES+ve 495 (MH)$^+$.

Example 3

2-(4-{[6-({(2R)-2-Hydroxy-2-[4-hydroxy-3-(hydroxymethyl)phenyl]ethyl}amino)hexyl]oxy}butyl)benzenesulfonamide acetate i) 2-[4-({6-[(5R)-5-(2,2-Dimethyl-4H-1,3-benzo-dioxin-6-yl)-2-oxo-1,3-oxazolidin-3-yl]hexyl}oxy)butyl-ynyl]benzenesulfonamide was prepared using methods similar to those described in Example 1 vii.
LCMS RT=3.58 min.

ii) 2-[4-({6-[(5R)-5-(2,2-Dimethyl-4H-1,3-benzo-dioxin-6-yl)-2-oxo-1,3-oxazolidin-3-yl]hexyl}oxy)butyl]benzenesulfonamide was prepared using methods similar to those described in Example 1 viii.
LCMS RT=3.61 min.

iii) 2-{4-[(6-{[(2R)-2-(2,2-Dimethyl-4H-1,3-benzo-dioxin-6-yl)-2-hydroxyethyl]amino}hexyl)oxy]butyl}-benzenesulfonamide was prepared using methods similar to those described in Example 1 ix.
LCMS RT=2.80 min.

iv) 2-(4-{[6-({(2R)-2-Hydroxy-2-[4-hydroxy-3-(hydroxymethyl)phenyl]ethyl}amino)hexyl]oxy}butyl)benzenesulfonamide acetate was prepared using methods similar to those described in Example 1×
LCMS RT=2.43 min, ES+ve 495 (MH)$^+$.

Example 4

3-(4-{[6-({(2R)-2-Hydroxy-2-[4-hydroxy-3-(hydroxymethyl)phenyl]ethyl}-amino)hexyl]oxy}butyl)-N-methylbenzenesulfonamide acetate i) 3-[4-({6-[(5R)-5-(2,2-Dimethyl-4H-1,3-benzo-dioxin-6-yl)-2-oxo-1,3-oxazolidin-3-yl]hexyl}oxy)but-1-ynyl]-N-methylbenzenesulfonamide was prepared using methods similar to those described in Example 1 vii.
ES+ve 571 (MH)$^+$.

ii) 3-[4-({6-[(5R)-5-(2,2-Dimethyl-4H-1,3-benzo-dioxin-6-yl)-2-oxo-1,3-oxazolidin-3-yl]hexyl}oxy)butyl]-N-methylbenzenesulfonamide was prepared using methods similar to those described in Example 1 viii.
ES+ve 575 (MH)$^+$.

iii) 3-{4-[(6-{[(2R)-2-(2,2-Dimethyl-4H-1,3-benzo-dioxin-6-yl)-2-hydroxyethyl]amino}hexyl)oxy]butyl}-N-methylbenzenesulfonamide was prepared using methods similar to those described in Example 1 ix.
ES+ve 549 (MH)$^+$.

iv) 3-(4-{[6-({(2R)-2-Hydroxy-2-[4-hydroxy-3-(hydroxymethyl)phenyl]ethyl}-amino)hexyl]oxy}butyl)-N-methylbenzenesulfonamide acetate was prepared using methods similar to those described in Example 1 x.
LCMS RT=2.45 min ES+ve 509 (MH)$^+$.

Example 5

2-(Hydroxymethyl)-4-{(1R)-1-hydroxy-2-[(6-{4-[3-(morpholin-4-ylsulfonyl)phenyl]butoxy}hexyl)amino]ethyl}phenol acetate i) (5R)-5-(2,2-Dimethyl-4H-1,3-benzodioxin-6-yl)-3-[6-({4-[3-(morpholin-4-ylsulfonyl)phenyl]but-3-ynyl}oxy)hexyl]-1,3-oxazolidin-2-one was prepared using methods similar to those described in Example 1 vii.
ES+ve 627 (MH)$^+$.

ii) (5R)-5-(2,2-Dimethyl-4H-1,3-benzodioxin-6-yl)-3-(6-{4-[3-(morpholin-4-ylsulfonyl)phenyl]butoxy}hexyl)-1,3-oxazolidin-2-one was prepared using methods similar to those described in Example 1 viii.
ES+ve 631 (MH)$^+$.

iii) (1R)-1-(2,2-Dimethyl-4H-1,3-benzodioxin-6-yl)-2-[(6-{4-[3-(morpholin-4-ylsulfonyl)phenyl]butoxy}hexyl)amino]ethanol was prepared using methods similar to those described in Example 1 ix.
ES+ve 605 (MH)$^+$.

iv) 2-(Hydroxymethyl)-4-{(1R)-1-hydroxy-2-[(6-{4-[3-(morpholin-4-ylsulfonyl)phenyl]butoxy}hexyl)amino]ethyl}phenol acetate was prepared using methods similar to those described in Example 1x.
LCMS RT=2.54 min ES+ve 565 (MH)$^+$.

Example 6

3-(4-{[6-({(2R)-2-Hydroxy-2-[4-hydroxy-3-(hydroxymethyl)phenyl]ethyl}-amino)hexyl]oxy}butyl)-N,N-dimethylbenzenesulfonamide acetate i) 3-[4-({6-[(5R)-5-(2,2-Dimethyl-4H-1,3-benzodioxin-6-yl)-2-oxo-1,3-oxazolidin-3-yl]hexyl}oxy)but-1-ynyl]-N,N-dimethylbenzenesulfonamide A mixture of (5R)-3-[6-(but-3-ynyloxy)hexyl]-5-(2,2-dimethyl-4H-1,3-benzodioxin-6-yl)-1,3-oxazolidin-2-one (0.256 g) and 3-bromo-N,N-dimethylbenzene sulphonamide (0.208 g) in pyrrolidine (4 ml) was degassed using vacuum/nitrogen cycle. Cuprous iodide (0.005 g) and dichlorobis(triphenylphosphine)palladium (0.037 g) were added and the mixture was stirred at 80° for 45 min under nitrogen. The mixture was diluted with EtOAc and washed with water. The aqueous phase was extracted with EtOAc and the combined organic phases washed with brine, dried ($Na_2SO_4$) and evaporated to dryness. The residue was dissolved in $CH_2Cl_2$ and applied to a silica Bond Elut Cartridge (10 g). The cartridge was eluted with $CH_2Cl_2$, cyclohexane/$Et_2O$, $Et_2O$ and EtOAc. Evaporation of the ether fractions gave an oil which was repurified by silica Bond Elut to give the title compound (0.23 g), ES+ve 585 (MH)+.

ii) 3-[4-({6-[(5R)-5-(2,2-Dimethyl-4H-1,3-benzodioxin-6-yl)-2-oxo-1,3-oxazolidin-3-yl]hexyl}oxy)butyl]-N,N-dimethylbenzenesulfonamide was prepared using methods similar to those described in Example 1 viii.
ES+ve 587 (MH)+.

iii) 3-{4-[(6-{[(2R)-2-(2,2-Dimethyl-4H-1,3-benzodioxin-6-yl)-2-hydroxyethyl]amino}hexyl)oxy]butyl}-N,N-dimethylbenzenesulfonamide was prepared using methods similar to those described in Example 1 ix.
ES+ve 563 (MH)+.

iv) 3-(4-{[6-({(2R)-2-Hydroxy-2-[4-hydroxy-3-(hydroxmethyl)phenyl]ethyl}-amino)hexyl]oxy}butyl)-N,N-dimethylbenzenesulfonamide acetate was prepared using methods similar to those described in Example 1 x.
LCMS RT=2.52 min ES+ve 523 (MH)+.

Example 7

3-(4-{[6-({(2R)-2-Hydroxy-2-[4-hydroxy-3-(hydroxymethyl)phenyl]ethyl}-amino)hexyl]oxy}butyl)-N-isopropylbenzenesulfonamide acetate i) 3-[4-({6-[(5R)-5-(2,2-Dimethyl-4H-1,3-benzodioxin-6-yl)-2-oxo-1,3-oxazolidin-3-yl]hexyl}oxy)but-1-ynyl]-N-isopropylbenzenesulfonamide was prepared using methods similar to those described in Example 6 i.
ES+ve 599 (MH)+.

ii) 3-[4-({6-[(5R)-5-(2,2-Dimethyl-4H-1,3-benzodioxin-6-yl)-2-oxo-1,3-oxazol idin-3-yl]hexyl}oxy)butyl]-N-isopropylbenzenesulfonamide was prepared using methods similar to those described in Example 1 viii.
ES+ve 603 (MH)+.

iii) 3-{4-[(6-{[(2R)-2-(2,2-Dimethyl-4H-1,3-benzodioxin-6-yl)-2-hydroxyethyl]amino}hexyl)oxy]butyl}-N-isopropylbenzenesulfonamide was prepared using methods similar to those described in Example 1 ix.
ES+ve 577 (MH)+.

iv) 3-(4-{[6-({(2R)-2-Hydroxy-2-[4-hydroxy-3-(hydroxymethyl)phenyl]ethyl}-amino)hexyl]oxy}butyl)-N-isopropylbenzenesulfonamide acetate was prepared using methods similar to those described in Example 1 x.
LCMS RT=2.56 min ES+ve 537 (MH)+.

Example 8

N-(tert-Butyl)-3-(4-{[6-({(2R)-2-hydroxy-2-[4-hydroxy-3-(hydroxymethyl)phenyl]ethyl}amino)hexyl]oxy}butyl)benzenesulfonamide acetate i) N-(tert-Butyl)-3-[4-({6-[(5R)-5-(2,2-dimethyl-4H-1,3-benzodioxin-6-yl)-2-oxo-1,3-oxazolidin-3-yl]hexyl}oxy)but-1-ynyl]benzenesulfonamide was prepared using methods similar to those described in Example 6i.
ES+ve 613 (MH)+.

ii) N-(tert-Butyl)-3-[4-({6-[(5R)-5-(2,2-dimethyl-4H-1,3-benzodioxin-6-yl)-2-oxo-1,3-oxazolidin-3-yl]hexyl}oxy)butyl]benzenesulfonamide was prepared using methods similar to those described in Example 1 viii.
ES+ve 617 (MH)+.

iii) N-(tert-Butyl)-3-{4-[(6-{[(2R)-2-(2,2-dimethyl-4H-1,3-benzodioxin-6-yl)-2-hydroxyethyl]amino}hexyl)oxy]butyl}benzenesulfonamide was prepared using methods similar to those described in Example 1 ix.
ES+ve 591 (MH)+.

iv) N-(tert-Butyl)-3-(4-{[6-({(2R)-2-hydroxy-2-[4-hydroxy-3-(hydroxymethyl)phenyl]ethyl}amino)hexyl]oxy}butyl)benzenesulfonamide acetate was prepared using methods similar to those described in Example 1x.
LCMS RT=2.63 min ES+ve 551 (MH)+.

Example 9

2-(Hydroxymethyl)-4-{(1R)-1-hydroxy-2-[(6-{4-[3-(piperidin-1-ylsulfonyl)phenyl]butoxy}hexyl)amino]ethyl}phenol acetate i) (5R)-5-(2,2-Dimethyl-4H-1,3-benzodioxin-6-yl)-3-[6-({4-[3-(piperidin-1-ylsulfonyl)phenyl]but-3-ynyl}oxy)hexyl]-1,3-oxazolidin-2-one was prepared using methods similar to those described in Example 6 i.
ES+ve 625 (MH)+.

ii) (5R)-5-(2,2-Dimethyl-4H-1,3-benzodioxin-6-yl)-3-(6-{4-[3-(piperidin-1-ylsulfonyl)phenyl]butoxy}hexyl)-1,3-oxazolidin-2-one was prepared using methods similar to those described in Example 1 viii.
ES+ve 629 (MH)+.

iii) (1R)-1-(2,2-Dimethyl-4H-1,3-benzodioxin-6-yl)-2-[(6-{4-[3-(piperidin-1-ylsulfonyl)phenyl]butoxy}hexyl)amino]ethanol was prepared using methods similar to those described in Example 1 ix.
ES+ve 603 (MH)+.

iv) 2-(Hydroxymethyl)-4-{(1R)-1-hydroxy-2-[(6-{4-[3-(piperidin-1-ylsulfonyl)phenyl]butoxy}hexyl)amino]ethyl}phenol acetate was prepared using methods similar to those described in Example 1 x.
LCMS RT=2.72 min ES+ve 563 (MH)+.

Example 10

1-[3-(4-{[6-({(2R)-2-Hydroxy-2-[4-hydroxy-3-(hydroxymethyl)phenyl]ethyl}amino)-hexyl]oxy}butyl)phenyl]methanesulfonamide i) Sodium (3-iodophenyl)methanesulfonate

A solution of 3-iodobenzyl bromide (3 g) and sodium sulphite (1.26 g) in acetone (15 ml) and water (30 ml) was heated at 70° for 3 h. The solvent was removed under reduced pressure and the residue was triturated in ether to give the title compound (3.8 g). LCMS RT=3.66 min.

ii) (3-Iodophenyl)methanesulfonyl chloride

A stirred mixture of sodium (3-iodophenyl)methanesulfonate (3.6 g) and phosphoryl chloride (10 ml) in sulpholane (20 ml) and acetonitrile (30 ml) was heated at 70° for 2 h. The mixture was poured onto crushed ice (200 ml) and the precipitated product was collected and dried to give the title product (2.8 g) LCMS RT=3.47 min.

iii) (3-Iodophenyl)methanesulfonamide

A stirred solution of (3-iodophenyl)methanesulfonyl chloride (1 g) in THF (20 ml) was treated with 0.88 ammonia (25 ml) at room temperature for 30 min. The solvent was removed under reduced pressure and the residue was triturated in ether to give the title compound (0.35 g).
LCMS RT=2.71 min.

iv) {3-[4-({6-[(5R)-5-(2,2-Dimethyl-4H-1,3-benzodioxin-6-yl)-2-oxo-1,3-oxazolidin3-yl]hexyl}oxy)but-1-ynyl]phenyl}methanesulfonamide was prepared using methods similar to those described in Example 1 vii.
ES+ve 571 (MH)+ v) 3-[4-({6-[(5R)-5-(2,2-Dimethyl-4H-1,3-benzodioxin-6-yl)-2-oxo-1,3-oxazolidin-3-yl]hexyl}oxy)butyl]phenylmethanesulfonamide was prepared using methods similar to those described in Example 1 viii.
ES+ve 575 (MH)+ vi) {3-{4-[(6-{[(2R)-2-(2,2-Dimethyl-4-H-1,3-benzodioxin-6-yl)-2-hydroxyethyl]amino}hexyl)oxy]butyl}phenyl}methanesulfonamide was prepared using methods similar to those described in Example 1 ix.
ES+ve 549 (MH)+ vii) [3-(4-{[6-({(2R)-2-Hydroxy-2-[4-hydroxy-3-(hydroxymethyl)phenyl]-ethyl}amino)hexyl]oxy}butyl)phenyl]methanesulfonamide was prepared using methods similar to those described in Example 1x.
LCMS RT=2.22 min ES+ve 509 (MH)+

Example 11

3-(5-{[5-({(2R)-2-Hydroxy-2-[4-hydroxy-3-(hydroxymethyl)phenyl]ethyl}amino)pentyl]oxy}pentyl)benzenesulfonamide acetate i) 5-[(5-Bromopentyl)oxy]pent-1-yne was prepared using methods similar to those described in Example 1 v.
LCMS RT=3.62 min.

ii) (5R)-5-(2,2-Dimethyl-4H-1,3-benzodioxin-6-yl)-3-[5-(pent-4-ynyloxy)pentyl]-1,3-oxazolidin-2-one was prepared using methods similar to those described in Example 1 vi.
LCMS RT=3.50 min.

iii) 3-[5-({5-[(5R)-5-(2,2-Dimethyl-4H-1,3-benzodioxin-6-yl)-2-oxo-1,3-oxazolidin-3-yl]pentyl}oxy)pent-1-ynyl]benzenesulfonamide was prepared using methods similar to those described in Example 1 vii.
LCMS RT=3.42 min.

iv) 3-[5-({5-[(5R)-5-(2,2-Dimethyl-4H-1,3-benzo-dioxin-6-yl)-2-oxo-1,3-oxazolidin-3-yl]pentyl}oxy)pentyl]benzenesulfonamide was prepared using methods similar to those described in Example 1 viii.
LCMS RT=3.58 min.

v) 3-{5-[(5-{[(2R)-2-(2,2-Dimethyl-4H-1,3-benzo-dioxin-6-yl)-2-hydroxyethyl]amino}pentyl)oxy]pentyl}benzenesulfonamide was prepared using methods similar to those described in Example 1 ix.
LCMS RT=2.75 min.

vi) 3-(5-{[5-({(2R)-2-Hydroxy-2-[4-hydroxy-3-(hydroxymethyl)phenyl]ethyl}amino)pentyl]oxy}pentyl)benzenesulfonamide acetate was prepared using methods similar to those described in Example 1 x.
LCMS RT=2.46 min, ES+ve 495 (MH)$^+$.

Example 12

3-(3-{[7-({(2R)-2-Hydroxy-2-[4-hydroxy-3-(hydroxymethyl)phenyl]ethyl}amino)heptyl]oxy}propyl)benzenesulfonamide acetate i) 3-[(7-Bromoheptyl)oxy]prop-1-yne was prepared using methods similar to those described in Example 1 v.
LCMS RT=3.63 min.

ii) (5R)-5-(2,2-Dimethyl-4H-1,3-benzodioxin-6-yl)-3-[7-(prop-2-ynyloxy)heptl]-1,3-oxazolidin-2-one was prepared using methods similar to those described in Example 1 vi.
LCMS RT=3.57 min.

iii) 3-[3-({7-[(5R)-5-(2,2-Dimethyl-4H-1,3-benzo-dioxin-6-yl)-2-oxo-1,3-oxazolidin-3-yl]heptyl}oxy)prop-1-ynyl]benzenesulfonamide was prepared using methods similar to those described in Example 1 vii.
LCMS RT=3.51 min.

iv) 3-[3-({7-[(5R)-5-(2,2-Dimethyl-4H-1,3-benzo-dioxin-6-yl)-2-oxo-1,3-oxazolidin-3-yl]heptyl}oxy)propyl]benzenesulfonamide was prepared using methods similar to those described in Example 1 viii.
LCMS RT=3.58 min.

v) 3-{3-[(7-{[(2R)-2-(2,2-Dimethyl-4H-1,3-benzo-dioxin-6-yl)-2-hydroxyethyl]amino}heptyl)oxy]propyl}benzenesulfonamide was prepared using methods similar to those described in Example 1 ix.
LCMS RT=2.75 min.

vi) 3-(3-{[7-({(2R)-2-Hydroxy-2-[4-hydroxy-3-(hydroxymethyl)phenyl]ethyl}amino)heptyl]oxy}propyl)benzenesulfonamide acetate was prepared using methods similar to those described in Example 1 x.
LCMS RT=2.46 min, ES+ve 495 (MH)$^+$.

Example 13

3-{6-[4-({(2R)-2-Hydroxy-2-[4-hydroxy-3-(hydroxymethyl)phenyl]ethyl}amino)butoxy]hexyl}benzenesulfonamide acetate i) 6-(4-Bromobutoxy)hex-1-yne was prepared using methods similar to those described in Example 1 v.
LCMS RT=3.49 min.

ii) (5R)-5-(2,2-Dimethyl-4H-1,3-benzodioxin-6-yl)-3-[4-(hex-5-ynyloxy)butyl]-1,3-oxazolidin-2-one was prepared using methods similar to those described in Example 1 vi.
LCMS RT=3.48 min.

iii) 3-(6-{-4-[(5R)-5-(2,2-Dimethyl-4H-1,3-benzo-dioxin-6-yl)-2-oxo-1,3-oxazolidin-3-yl]butoxy}hex-1-ynyl)benzenesulfonamide was prepared using methods similar to those described in Example 1 vii.
LCMS RT=3.42 min.

iv) 3-(6-{4-[(5R)-5-(2,2-Dimethyl-4H-1,3-benzo-dioxin-6-yl)-2-oxo-1,3-oxazolidin-3-yl]butoxy}hexyl)benzenesulfonamide was prepared using methods similar to those described in Example 1 viii.
LCMS RT=3.58 min.

v) 3-[6-(4-{[(2R)-2-(2,2-Dimethyl-4H-1,3-benzo-dioxin-6-yl)-2-hydroxyethyl]amino}butoxy)hexyl]benzenesulfonamide was prepared using methods similar to those described in Example 1 ix.
LCMS RT=2.66 min.

vi) 3-{6-[4-({(2R)-2-Hydroxy-2-[4-hydroxy-3-(hydroxymethyl)phenyl]ethyl}amino)butoxy]hexyl}benzenesulfonamide acetate was prepared using methods similar to those described in Example 1 x.
LCMS RT=2.47 min, ES+ve 495 (MH)$^+$.

Example 14

4-[3-(4-{[6-({(2R)-2-Hydroxy-2-[4-hydroxy-3-(hydroxymethyl)phenyl]ethyl}amino)hexyl]oxy}butyl)phenyl]butane-1-sulfonamide i) 4-(3-Iodophenyl)butyl methanesulfonate 4-(3-Iodophenyl)butan-1-ol (1.7 g) was stirred with diisopropylamine (1.74 ml) and methanesulfonyl chloride (0.66 ml) in dichloromethane (50 ml) at 21° for 2 h. The solution was washed successively with sodium bicarbonate solution, water, water acidified with a few drops of 2M HCl and water, each time back extracting with dichloromethane. The combined organic layers were dried (MgSO$_4$) and evaporated to give the title compound (2,23 g), tlc R$_f$=0.28 (1:3 ethyl acetate in cyclohexane)

ii) 4-(3-Iodophenyl)butane-1-sulfonamide 4-(3-Iodophenyl)butyl methanesulfonate (0.354 g) was stirred with sodium iodide (0.75 g) in acetone (5 ml) under nitrogen for 3 h and at 35° for 30 min. The mixture was partitioned between dichloromethane and water. The aqueous layer was extracted with more dichloromethane and the combined organic layers were washed with water. After drying (MgSO$_4$) the solution was evaporated to an oil. This was dissolved in ethanol (10 ml) and water (5 ml) and the mixture was refluxed on a steam bath for 12 h with sodium sulfite (0.138 g). The mixture was cooled and the solid was collected by filtration, washed with water and dried. This residue was refluxed with phosphorus oxychloride (4 ml) under nitrogen for 4 h and then blown dry with a stream of nitrogen. 0.880 Ammonia solution (5 ml) was added and the mixture was refluxed for 2 h. More ammonia solution (5 ml) was added and refluxing was continued for 45 min. The mixture was cooled and the solid was collected by filtration, washed with water and dried to give the title compound (0.2 g) LCMS RT=3.15 min.

iii) 4-{3-[4-({6-[(5R)-5-(2,2-Dimethyl-4H-1,3-benzodioxin-6-yl)-2-oxo-1,3-oxazolidin-3-yl]hexyl}oxy)but-1-ynyl]phenyl}butane-1-sulfonamide was prepared using methods similar to those described in Example 1 vii.
LCMS RT=3.62 min.

iv) 4-{3-[4-({6-[(5R)-5-(2,2-Dimethyl-4H-1,3-benzodioxin-6-yl)-2-oxo-1,3-oxazolidin-3-yl]hexyl}oxy)butyl]phenyl}butane-1-sulfonamide was prepared using methods similar to those described in Example 1 viii.
LCMS RT=3.71 min.

v) 4-[3-(4-{[6-({(2R)-2-Hydroxy-2-[4-hydroxy-3-(hydroxymethyl)phenyl]ethyl}amino)hexyl]oxy}butyl)phenyl]butane-1-sulfonamide 4-{3-[4-({6-[(5R)-5-(2,2-Dimethyl-4H-1,3-benzodioxin-6-yl)-2-oxo-1,3-oxazolidin-3-yl]hexyl}oxy)butyl]phenyl}butane-1-sulfonamide (0.097 g) was stirred and refluxed with potassium trimethylsilanoate (0.1 g) under nitrogen for 2 h. The mixture was evaporated to dryness and re-evaporated with methanol. The residue was taken up in methanol and loaded onto a Bond Elut SCX2 cartridge (10 g) which had been preconditioned with methanol. The cartridge was left for 30 min and then eluted successively with methanol and then 1% 0.880 aqueous ammonia solution in methanol. This gave the title compound (0.064 g), LCMS RT=2.72 min, ES+ve 551 (MH)$^+$.

Example 15

3-(5-{[6-({(2R)-2-Hydroxy-2-[4-hydroxy-3-(hydroxymethyl)phenyl]ethyl}amino)hexyl]oxy}pentyl)benzenesulfonamide i) 5-[(6-bromohexyl)oxy]pent-1-yne was prepared using methods similar to those described in Example 1 v.
GCMS RT=5.6 min ii) (5R)-5-(2,2-Dimethyl-4H-1,3-benzodioxin-6-yl)-3-[6-(pent-4-ynyloxy)hexyl]-1,3-oxazolidin-2-one was prepared using methods similar to those described in Example 1 iv.
LCMS RT=3.65 min iii) 3-[5-({6-[(5R)-5-(2,2-Dimethyl-4H-1,3-benzodioxin-6-yl)-2-oxo-1,3-oxazolidin-3-yl]hexyl}oxy)pent-1-ynyl]benzenesulfonamide was prepared using methods similar to those described in Example 1 vii.
LCMS RT=3.76 min iv) 3-[5-({6-[(5R)-5-(2,2-Dimethyl-4H-1,3-benzodioxin-6-yl)-2-oxo-1,3-oxazolidin-3-yl]hexyl}oxy)pentyl]benzenesulfonamide was prepared using methods similar to those described in Example 1 viii.
LCMS RT=3.57 min v) 3-(5-{[6-({(2R)-2-Hydroxy-2-[4-hydroxy-3-(hydroxymethyl)phenyl]ethyl}amino)hexyl]oxy}pentyl)benzenesulfonamide was prepared using methods similar to those described in Example 14 v.
LCMS R=2.47 min, ES+ve 509 (MH)$^+$.

Example 16

3-(6-{[6-({(2R)-2-Hydroxy-2-[4-hydroxy-3-(hydroxymethyl)phenyl]ethyl}amino)hexyl]oxy}hexyl)benzenesulfonamide i) 6-[(6-Bromohexyl)oxy]hex-1-yne was prepared using methods similar to those described in Example 1 v.
GCMS RT=5.99 min ii) (5R)-5-(2,2-Dimethyl-4H-1,3-benzodioxin-6-yl)-3-[6-(hex-5-ynyloxy)hexyl]-1,3-oxazolidin-2-one was prepared using methods similar to those described in Example 1 iv.
LCMS RT=3.73 min iii) 3-[6-({6-[(5R)-5-(2,2-Dimethyl-4H-1,3-benzodioxin-6-yl)-2-oxo-1,3-oxazolidin-3-yl]hexyl}oxy)hex-1-ynyl]benzenesulfonamide was prepared using methods similar to those described in Example 1 vii.
LCMS RT=3.74 min iv) 3-[6-({6-[(5R)-5-(2,2-Dimethyl-4H-1,3-benzodioxin-6-yl)-2-oxo-1,3-oxazolidin-3-yl]hexyl}oxy)hexyl]benzenesulfonamide was prepared using methods similar to those described in Example 1 viii.
LCMS RT=3.69 min v) 3-(6-{[6-({(2R)-2-hydroxy-2-[4-hydroxy-3-(hydroxymethyl)phenyl]ethyl}amino)hexyl]oxy}hexyl)benzenesulfonamide was prepared using methods similar to those described in Example 14 v.
LCMS RT=2.57 min, ES+ve 523 (MH)$^+$.

Example 17

3-(3-{[6-({(2R)-2-Hydroxy-2-[4-hydroxy-3-(hydroxymethyl)phenyl]ethyl}amino)hexyl]oxy}propyl)benzenesulfonamide acetate i) 3-[(6-Bromohexyl)oxy]prop-1-yne was prepared using methods similar to those described in Example 1 v.
δ (CDCl$_3$) 4.13 (2H, s), 3.52 (2H, t, J 7 Hz), 3.41 (2H, t, J 7 Hz), 2.42 (1H, t J 2 Hz), 1.91 to 1.82 (2H, m), 1.66 to 1.58 (2H, m) and 1.51 to 1.35 (4H, m).

ii) (5R)-5-(2,2-Dimethyl-4H-1,3-benzodioxin-6-yl)-3-[6-(prop-2-ynyloxy)hexyl]-1,3-oxazolidin-2-one was prepared using methods similar to those described in Example 1 vi.
LCMS RT=3.45 min iii) 3-[3-({6-[(5R)-5-(2,2-Dimethyl-4H-1,3-benzodioxin-6-yl)-2-oxo-1,3-oxazolidin-3-yl]hexyl}oxy)prop-1-ynyl]benzenesulfonamide was prepared using methods similar to those described in Example 1 vii.
LCMS RT=3.52 min iv) 3-[3-({6-[(5R)-5-(2,2-Dimethyl-4H-1,3-benzodioxin-6-yl)-2-oxo-1,3-oxazolidin-3-yl]hexyl}oxy)propyl]benzenesulfonamide was prepared using methods similar to those described in Example 1 viii.
LCMS RT=3.48 min v) 3-{3-[(6-{[(2R)-2-(2,2-Dimethyl-4H-1,3-benzodioxin-6-yl)-2-hydroxyethyl]amino}hexyl)oxy]propyl}benzenesulfonamide was prepared using methods similar to those described in Example 1 ix.
LCMS RT=2.81 min vi) 3-(3-{[6-({(2R)-2-Hydroxy-2-[4-hydroxy-3-(hydroxymethyl)phenyl]ethyl}amino)hexyl]oxy}propyl)benzenesulfonamide acetate was prepared using methods similar to those described in Example 1 x.
LCMS RT=2.48 min, ES+ve 481 (MH)$^+$.

Example 18

3-(4-{[5-({(2R)-2-Hydroxy-2-[4-hydroxy-3-(hydroxymethyl)phenyl]ethyl}amino)pentyl]oxy}butyl)benzenesulfonamide acetate i) 4-[(5-Bromopentyl)oxy]but-1-yne was prepared using methods similar to those described in Example 1 v.
δ (MeOD) 3.43 (2H, t, J 7 Hz), 3.41 to 3.32 (4H, m), 2.32 (2H, dt, J 2,7 Hz), 2.15 (1H, t, J 2 Hz), 1.81 to 1.73 (2H, m), 1.54 to 1.38 (4H, m).

ii) (5R)-3-[5-(But-3-ynyloxy)pentyl]-5-(2,2-dimethyl-4H-1,3-benzodioxin-6-yl)-1,3-oxazolidin-2-one was prepared using methods similar to those described in Example 1 vi.
LCMS RT=3.87 min iii) 3-[4-({5-[(5R)-5-(2,2-Dimethyl-4H-1,3-benzodioxin-6-yl)-2-oxo-1,3-oxazolidin-3-yl]pentyl}oxy)but-1-ynyl]benzenesulfonamide was prepared using methods similar to those described in Example 1 vii.
LCMS RT=3.47 min iv) 3-[4-(5-[(5R)-5-(2,2-Dimethyl-4H-1,3-benzodioxin-6-yl)-2-oxo-1,3-oxazolidin-3-yl]pentyl}oxy)butyl]benzenesulfonamide was prepared using methods similar to those described in Example 1 viii.
LCMS RT=3.37 min v) 3-{4-[(5-{[(2R)-2-(2,2-Dimethyl-4H-1,3-benzodioxin-6-yl)-2-hydroxyethyl]amino}pentyl)oxy]butyl}benzenesulfonamide was prepared using methods similar to those described in Example 1 ix.
LCMS RT=2.81 min vi) 3-(4-{[5-({(2R)-2-Hydroxy-2-[4-hydroxy-3-(hydroxymethyl)phenyl]ethyl}amino)pentyl]oxy}butyl)benzenesulfonamide acetate was prepared using methods similar to those described in Example 1 x.
LCMS RT=2.41 min, ES+ve 481 (MH)+.

Example 19

N-[3-(Aminosulfonyl)phenyl]-3-(4-{[6-({(2R)-2-hydroxy-2-[4-hydroxy-3-(hydroxymethyl)phenyl]ethyl}amino)hexyl]oxy}butyl)benzenesulfonamide acetate N-[3-(Aminosulfonyl)phenyl]-3-[4-({6-[(5R)-5-(2,2-dimethyl-4H-1,3-benzodioxin-6-yl)-2-oxo-1,3-oxazolidin-3-yl]hexyl}oxy)but-1-ynyl]benzenesulfonamide was prepared using methods similar to those described in Example 1 vii.
LCMS RT=3.72 min.

i) N-[3-(Aminosulfonyl)phenyl]-3-[4-({6-[(5R)-5-(2,2-dimethyl-4H-1,3-benzodioxin-6-yl)-2-oxo-1,3-oxazolidin-3-yl]hexyl}oxy)butyl]benzenesulfonamide was prepared using methods similar to those described in Example 1 viii.
LCMS RT=3.61 min.

ii) N-[3-(Aminosulfonyl)phenyl]-3-{4-[(6-{[(2R)-2-(2,2-dimethyl-4H-1,3-benzodioxin-6-yl)-2-hydroxyethyl]amino}hexyl)oxy]butyl}benzenesulfonamide was prepared using methods similar to those described in Example 1 ix.
LCMS RT=2.88 min.

iii) N-[3-(Aminosulfonyl)phenyl]-3-(4-{[6-({(2R)-2-hydroxy-2-[4-hydroxy-3-(hydroxymethyl)phenyl]ethyl}amino)hexyl]oxy}butyl)benzenesulfonamide acetate was prepared using methods similar to those described in Example 1 x.
LCMS RT=2.95 min, ES+ve 650 (MH)+.

Example 20

1-[4-(4-{[6-({(2R)-2-Hydroxy-2-[4-hydroxy-3-(hydroxymethyl)phenyl]ethyl}amino)hexyl]oxy}butyl)phenyl]methanesulfonamide i) Sodium (4-iodophenyl)methanesulfonate was prepared using methods similar to those described in Example 10 i.
tlc (SiO$_2$, 1:1 EtOAc/Cyclohexane/1% AcOH)Rf=0.57).

ii) 1-(4-Iodophenyl)methanesulfonamide was prepared using methods similar to those described in Example 10 iii.
LCMS RT=2.63 min iii) 1-{4-[4-({6-[(5R)-5-(2,2-Dimethyl-4H-1,3-benzodioxin-6-yl)-2-oxo-1,3-oxazolidin-3-yl]hexyl}oxy)but-1-ynyl]phenyl}methanesulfonamide was prepared using methods similar to those described in Example 1 vii.
LCMS RT=3.43 min iv) 1-{4-[4-({6-[(5R)-5-(2,2-Dimethyl-4H-1,3-benzodioxin-6-yl)-2-oxo-1,3-oxazolidin-3-yl]hexyl}oxy)butyl]phenyl}methanesulfonamide was prepared using methods similar to those described in Example 1 viii.
LCMS RT=3.50 min v) 1-[4-(4-{[6-({(2R)-2-Hydroxy-2-[4-hydroxy-3-(hydroxymethyl)phenyl]ethyl}amino)hexyl]oxy}butyl)phenyl]methanesulfonamide was prepared using methods similar to those described in Example 14 v.
LCMS RT=2.35, ES+ve 509 (MH)+.

Example 21

1-[2-(4-{[6-({(2R)-2-Hydroxy-2-[4-hydroxy-3-(hydroxymethyl)phenyl]ethyl}amino)hexyl]oxy}butyl)phenyl]methanesulfonamide i) Sodium (2-iodophenyl)methanesulfonate was prepared using methods similar to those described in Example 10 i.
tlc (SiO$_2$, 1:1 EtOAc/Cyclohexane/1% AcOH)Rf=0.63.

ii) 1-(2-Iodophenyl)methanesulfonamide was prepared using methods similar to those described in Example 10 iii.
LCMS RT=2.44 min iii) 1-{2-[4-({6-[(5R)-5-(2,2-Dimethyl-4H-1,3-benzodioxin-6-yl)-2-oxo-1,3-oxazolidin-3-yl]hexyl}oxy)but-1-ynyl]phenyl}methanesulfonamide was prepared using methods similar to those described in Example 1 vii.
LCMS RT=3.46 min iv) 1-{2-[4-({6-[(5R)-5-(2,2-Dimethyl-4H-1,3-benzodioxin-6-yl)-2-oxo-1,3-oxazolidin-3-yl]hexyl}oxy)butyl]phenyl}methanesulfonamide was prepared using methods similar to those described in Example 1 viii.
LCMS RT=3.50 min v) 1-[2-(4-({6-[({(2R)-2-Hydroxy-2-[4-hydroxy-3-(hydroxymethyl)phenyl]ethyl}amino)hexyl]oxy}butyl)phenyl]methanesulfonamide was prepared using methods similar to those described in Example 14 v.
LCMS RT=2.40, ES+ve 509 (MH)+.

Example 22

N-Benzyl-3-(4-{[6-({(2R)-2-hydroxy-2-[4-hydroxy-3-(hydroxymethyl)phenyl]ethyl}amino)hexyl]oxy}butyl)benzenesulfonamide acetate i) N-Benzyl-3-[4-({6-[(5R)-5-(2,2-dimethyl-4H-1,3-benzodioxin-6-yl)-2-oxo-1,3-oxazolidin-3-yl]hexyl}oxy)but-1-ynyl]benzenesulfonamide was prepared using methods similar to those described in Example 6 i. ES+ve 647 (MH)+ ii) N-Benzyl-3-[4-({6-[(5R)-5-(2,2-dimethyl-4H-1,3-benzodioxin-6-yl)-2-oxo-1,3-oxazolidin-3-yl]hexyl}oxy)butyl]benzenesulfonamide was prepared using methods similar to those described in Example 1 viii. ES+ve 651 (MH)+ iii) N-Benzyl-3-{4-[(6-{[(2R)-2-(2,2-dimethyl-4H-3-benzodioxin-6-yl)-2-hydroxyethyl]amino}hexyl)oxy]butyl}benzenesulfonamide was prepared using methods similar to those described in Example 1 ix. ES+ve 625 (MH)+ iv) N-benzyl-3-(4-{[6-({(2R)-2-hydroxy-2-[4-hydroxy-3- was prepared using methods similar to those described in Example 1 x. LCMS RT=2.72 min, ES+ve 585 (MH)+

Example 23

4-{(1R)-2-[(6-{4-[3-({[(Ethylamino)carbonyl]amino}sulfonyl)phenyl]butoxy}hexyl)amino]-1-hydroxyethyl}-1-hydroxy-2-(hydroxymethyl)benzene acetate i) 3-[4-({6-[(5R)-5-(2,2-Dimethyl-4H-1,3-benzodioxin-6-yl)-2-oxo-1,3-oxazolidin-3-yl]hexyl}oxy)butyl]-N-[(ethylamino)carbonyl]benzenesulfonamide Ethyl isocyanate (0.015 g) was added to a stirred mixture of 3-[4-({6-[(5R)-5-(2,2-dimethyl-4H-1,3-benzodioxin-6-yl)-2-oxo-1,3-oxazolidin-3-yl]hexyl}oxy)butyl]benzenesulfonamide (0.11 g) and K$_2$CO$_3$ (0.055 g) in acetone (2 ml). The mixture was heated at reflux for 2 h then ethyl isocyanate (0.005 g) was added. After 0.5 h the reaction mixture was cooled and quenched with water (1 ml). The mixture was partitioned between EtOAc (20 ml) and H$_2$O (20 ml). The aqueous phase was extracted with EtOAc (20 ml). The combined EtOAc phases were washed with brine (10 ml) then dried (Na$_2$SO$_4$) and concentrated. The residue was purified by SPE (silica 5 g) with
CH$_2$Cl$_2$ (2×15 ml), Et$_2$O (2×15 ml) and EtOAc (2×15 ml), evaporation of the EtOAc fractions afforded the title compound (0.067 g). ES+ve 632 (MH)+ ii) 4-{(1R)-2-[(6-{4-[3-({[(Ethylamino)carbonyl]amino}sulfonyl)phenyl]butoxy}hexyl)amino]-1-hydroxyethyl}-1-hydroxy-2-(hydroxymethyl)benzene acetate was prepared using methods similar to those described in Example 1×. LCMS RT=2.86 min, ES+ve 606 (MH)+

Example 24

3-(4-{[6-({2-Hydroxy-2-[4-hydroxy-3-(hydroxymethyl)phenyl]ethyl}amino)hexyl]oxy}butyl)benzenesulfonamide acetate i) tert-Butyl 2-(2,2-dimethyl-4H-1,3-benzodioxin-6-yl)-2-hydroxyethylcarbamate Recrystallisation of a batch of 3:1 (R:S) Example 1 iii (78.94 g) gave the title compound (27.6 g).
LCMS RT=3.31 min ii) 5-(2,2-Dimethyl-4H-1,3-benzodioxin-6-yl)-1,3-oxazolidin-2-one was prepared using methods similar to those described in Example 1 iv. ES+ve 250 (MH)+ iii) 3-[6-(But-3-ynyloxy)hexyl]-5-(2,2-dimethyl-4H-1,3-benzodioxin-6-yl)-1,3-oxazolidin-2-one was prepared using methods similar to those described in Example 1 vi. ES+ve 402 (MH)+ iv) 3-[4-({6-[5-(2,2-Dimethyl-4H-1,3-benzodioxin-6-yl)-2-oxo-1,3-oxazolidin-3-yl]hexyl}oxy)but-1-ynyl]benzenesulfonamide was prepared using methods similar to those described in Example 1 vii. ES+ve 557 (MH)+ v) 3-[4-({6-[5-(2,2-Dimethyl-4H-1,3-benzodioxin-6-yl)-2-oxo-1,3-oxazolidin-3-yl]hexyl}oxy)butyl]benzenesulfonamide was prepared using methods similar to those described in Example 1 viii. ES+ve 561 (MH)+ vi) 3-{4-[(6-{[2-(2,2-Dimethyl-4H-1,3-benzodioxin-6-yl)-2-hydroxyethyl]amino}hexyl)oxy]butyl}benzenesulfonamide was prepared using methods similar to those described in Example 1 ix. ES+ve 535 (MH)+ vii) 3-(4-{[6-({2-Hydroxy-2-[4-hydroxy-3-(hydroxymethyl)phenyl]ethyl}amino)hexyl]oxy}butyl)benzenesulfonamide acetate was prepared using methods similar to those described in Example 1×. LCMS RT=2.90 min, ES+ve 495 (MH)+

Example 25

3-(4-{[6-({(2S)-2-Hydroxy-2-[4-hydroxy-3-(hydroxymethyl)phenyl]ethyl}amino)hexyl]oxy}butyl)benzenesulfonamide acetate i) 3-{-4-[(6-{[(2S)-2-(2,2-Dimethyl-4H-1,3-benzodioxin-6-yl)-2-hydroxyethyl]amino}hexyl)oxy]butyl}benzenesulfonamide Resolution of 3-{4-[(6-{2-(2,2-dimethyl-4H-1,3-benzodioxin-6-yl)-2-hydroxyethyl]amino}hexyl)oxy]

butyl}benzenesulfonamide (0.403 g) on an HPLC Chiralcel OJ column using 40% ethanol/heptane afforded the title compound (0.096 g).

ii) 3-(4-{[6-({(2S)-2-Hydroxy-2-[4-hydroxy-3-(hydroxymethyl)phenyl]ethyl}amino)hexyl]oxy}butyl)benzenesulfonamide acetate was prepared using methods similar to those described in Example 1 x. LCMS RT=2.44 min, ES+ve 495 (MH)$^+$

Example 26

N-[4-({[3-(4-{[6-({(2R)-2-Hydroxy-2-[4-hydroxy-3-(hydroxymethyl)phenyl]ethyl}amino)hexyl]oxy}butyl)phenyl]sulfonyl}amino)phenyl]acetamide acetate i) N-{4-[({3-[4-({6-[(5R)-5-(2,2-Dimethyl-4H-1,3-benzodioxin-6-yl)-2-oxo-1,3-oxazolidin-3-yl]hexyl}oxy)but-1-ynyl]phenyl}sulfonyl)amino]phenyl}acetamide was prepared using methods similar to those described in Example 1 vii. ES−ve 688 (M−H)$^-$ ii) N-{4-[({3-[4-({6-[(5R)-5-(2,2-Dimethyl-4H-1,3-benzodioxin-6-yl)-2-oxo-1,3-oxazolidin-3-yl]hexyl}oxy)butyl]phenyl}sulfonyl)amino]phenyl}acetamide was prepared using methods similar to those described in Example 1 viii. ES−ve 692 (M−H)$^-$ iii) N-(4-{[(3-{4-[(6-{[(2R)-2-(2,2-Dimethyl-4H-1,3-benzodioxin-6-yl)-2-hydroxyethyl]amino}hexyl)oxy] butyl}phenyl)sulfonyl]amino}phenyl)acetamide was prepared using methods similar to those described in Example 1 ix. ES+ve 668 (MH)$^+$ iv) N-[4-({[3-(4-{[6-({(2R)-2-Hydroxy-2-[4-hydroxy-3-(hydroxymethyl)phenyl]ethyl}amino)hexyl]oxy}butyl)phenyl]sulfonyl}amino)phenyl]acetamide acetate GW671337A R5965/48/11 was prepared using methods similar to those described in Example 1×. LCMS RT=2.59 min, ES+ve 628 (MH)$^+$

Example 27

N-Cyclobutyl-3-(4-{[6-({(2R)-2-hydroxy-2-[4-hydroxy-3-(hydroxymethyl)phenyl]ethyl}amino)hexyl]oxy}butyl)benzenesulfonamide acetate (i) N-Cyclobutyl-3-[4-({6-[(5R)-5-(2,2-dimethyl-4H-1,3-benzodioxin-6-yl)-2-oxo-1,3-oxazolidin-3-yl]hexyl}oxy)but-1-ynyl]benzenesulfonamide was prepared using methods similar to those described in Example 1 vii. ES+ve 611 (MH)$^+$ ii) N-Cyclobutyl-3-[4-({6-[(5R)-5-(2,2-dimethyl-4H-1,3-benzodioxin-6-yl)-2-oxo-1,3-oxazolidin-3-yl]hexyl}oxy)butyl]benzenesulfonamide was prepared using methods similar to those described in Example 1 viii. ES+ve 615 (MH)$^+$ iii) N-Cyclobutyl-3-{4-[(6-{[(2R)-2-(2,2-dimethyl-4H-1,3-benzodioxin-6-yl)-2-hydroxyethyl]amino}hexyl)oxy]butyl}benzenesulfonamide was prepared using methods similar to those described in Example 1 ix. ES+ve 589 (MH)$^+$ iv) N-Cyclobutyl-3-(4-{[6-({(2R)-2-hydroxy-2-[4-hydroxy-3-(hydroxymethyl)phenyl]ethyl}amino)hexyl]oxy}butyl)benzenesulfonamide acetate was prepared using methods similar to those described in Example 1 x. LCMS RT=2.72 min, ES+ve 549 (MH)$^+$

Example 28

N-Cyclohexyl-3-(4-{[6-({(2R)-2-hydroxy-2-[4-hydroxy-3-(hydroxymethyl)phenyl]ethyl}amino)hexyl]oxy}butyl)benzenesulfonamide acetate i) N-Cyclohexyl-3-[4-({6-[(5R)-5-(2,2-dimethyl-4H-1,3-benzodioxin-6-yl)-2-oxo-1,3-oxazolidin-3-yl]hexyl}oxy)but-1-ynyl]benzenesulfonamide was prepared using methods similar to those described in Example 1 vii. ES+ve 639 (MH)$^+$ ii) N-Cyclohexyl-3-[4-({6-[(5R)-5-(2,2-dimethyl-4H-1,3-benzodioxin-6-yl)-2-oxo-1,3-oxazolidin-3-yl]hexyl}oxy)butyl]benzenesulfonamide was prepared using methods similar to those described in Example 1 viii. ES+ve 643 (MH)$^+$ iii) N-Cyclohexyl-3-{4-[(6-{[(2R)-2-(2,2-dimethyl-4H-1,3-benzodioxin-6-yl)-2-hydroxyethyl]amino}hexyl)oxy]butyl}benzenesulfonamide was prepared using methods similar to those described in Example 1 ix. ES+ve 617 (MH)$^+$ iv) N-Cyclohexyl-3-(4-{[6-({(2R)-2-hydroxy-2-[4-hydroxy-3-(hydroxymethyl)phenyl]ethyl}amino)hexyl]oxy}butyl)benzenesulfonamide acetate was prepared using methods similar to those described in Example 1 x. LCMS RT=2.85 min, ES+ve 577 (MH)$^+$

Example 29

3-(4-{[6-({(2R)-2-Hydroxy-2-[4-hydroxy-3-(hydroxymethyl)phenyl]ethyl}amino)hexyl]oxy}butyl)-N-(2-morpholin-4-ylethyl)benzenesulfonamide acetate i) 3-[4-({6-[(5R)-5-(2,2-Dimethyl-4H-1,3-benzodioxin-6-yl)-2-oxo-1,3-oxazolidin-3-yl]hexyl}oxy)but-1-ynyl]-N-(2-morpholin-4-ylethyl)benzenesulfonamide was prepared using methods similar to those described in Example 1 vii. ES+ve 670 (MH)$^+$ ii) 3-[4-({6-[(5R)-5-(2,2-Dimethyl-4H-1,3-benzodioxin-6-yl]-2-oxo-1,3-oxazolidin-3-yl]hexyl}oxy)butyl]-N-(2-morpholin-4-ylethyl)benzenesulfonamide was prepared using methods similar to those described in Example 1 viii. ES+ve 674 (MH)⁺ iii) 3-{4-[(6-{[(2R)-2-(2,2-Dimethyl-4H-1,3-benzodioxin-6-yl)-2-hydroxyethyl]-amino}hexyl)oxy]butyl}-N-(2-morpholin-4-ylethyl)benzenesulfonamide was prepared using methods similar to those described in Example 1 ix. ES+ve 648 (MH)⁺ iv) 3-(4-{[6-({(2R)-2-Hydroxy-2-[4-hydroxy-3-(hydroxymethyl)phenyl]ethyl}-amino)hexyl]oxy}butyl)-N-(2-morpholin-4-ylethyl)benzenesulfonamide acetate was prepared using methods similar to those described in Example 1 x. LCMS RT=2.22 min, ES+ve 608 (MH)⁺

Example 30

N-[2-(2-Hydroxyethoxy)ethyl]-3-(4-{[6-({(2R)-2-hydroxy-2-[4-hydroxy-3-(hydroxymethyl)phenyl]ethyl}amino)hexyl]oxy}butyl)benzenesulfonamide i) 3-[4-({6-[(5R)-5-(2,2-Dimethyl-4H-1,3-benzodioxin-6-yl]-2-oxo-1,3-oxazolidin-3-yl]hexyl}oxy)but-1-ynyl]-N-[2-(2-hydroxyethoxy)ethyl]benzenesulfonamide was prepared using methods similar to those described in Example 6 i. ES+ve 645 (MH)⁺ ii) 3-[4-({6-[(5R)-5-(2,2-Dimethyl-4H-1,3-benzodioxin-6-yl]-2-oxo-1,3-oxazolidin-3-yl]hexyl}oxy)butyl]-N-[2-(2-hydroxyethoxy)ethyl]benzenesulfonamide was prepared using methods similar to those described in Example 1 viii. ES+ve 647 (MH)⁻ iii) N-[2-(2-Hydroxyethoxy)ethyl]-3-(4-{[6-({(2R)-2-hydroxy-2-[4-hydroxy-3-(hydroxymethyl)phenyl]ethyl}amino)hexyl]oxy}butyl)benzenesulfonamide was prepared using methods similar to those described in Example 14 v. LCMS RT=2.62 min, ES+ve 583 (MH)⁺

Example 31

N-(4-Fluorophenyl)-3-(4-{[6-({(2R)-2-hydroxy-2-[4-hydroxy-3-(hydroxymethyl)phenyl]ethyl}amino)hexyl]oxy}butyl)benzenesulfonamide acetate i) 3-[4-({6-[(5R)-5-(2,2-Dimethyl-4H-1,3-benzodioxin-6-yl]-2-oxo-1,3-oxazolidin-3-yl]hexyl}oxy)but-1-ynyl]-N-(4-fluorophenyl)benzenesulfonamide was prepared using methods similar to those described in Example 1 vii. ES+ve 651 (MH)⁺ ii) 3-[4-({6-[(5R)-5-(2,2-dimethyl-4H-1,3-benzodioxin-6-yl]-2-oxo-1,3-oxazolidin-3-yl]hexyl}oxy)butyl]-N-(4-fluorophenyl)benzenesulfonamide was prepared using methods similar to those described in Example 1 viii. ES+ve 655 (MH)⁺ iii) 3-{-4-[(6-{[(2R)-2-(2,2-Dimethyl-4H-1,3-benzodioxin-6-yl)-2-hydroxyethyl]amino}hexyl)oxy]butyl}-N-(4-fluorophenyl)benzenesulfonamide was prepared using methods similar to those described in Example 1 ix. ES+ve 629 (MH)⁺ iv) N-(4-Fluorophenyl)-3-(4-{[6-({(2R)-2-hydroxy-2-[4-hydroxy-3-(hydroxymethyl)phenyl]ethyl}amino)hexyl]oxy}butyl)benzenesulfonamide acetate was prepared using methods similar to those described in Example 1 x. LCMS RT=2.81 min, ES+ve 589 (MH)⁺

Example 32

N-[4-(Aminosulfonyl)phenyl]-3-(4-{[6-({(2R)-2-hydroxy-2-[4-hydroxy-3-(hydroxymethyl)phenyl]ethyl}amino)hexyl]oxy}butyl)benzenesulfonamide acetate i) N-[4-(Aminosulfonyl)phenyl]-3-[4-({6-[(5R)-5-(2,2-dimethyl-4H-1,3-benzodioxin-6-yl)-2-oxo-1,3-oxazolidin-3-yl]hexyl}oxy)but-1-ynyl]benzenesulfonamide was prepared using methods similar to those described in Example 1 vii. ES+ve 712 (MH)⁺ ii) N-[4-(Aminosulfonyl)phenyl]-3-[4-({6-[(5R)-5-(2,2-dimethyl-4H-1,3-benzodioxin-6-yl)-2-oxo-1,3-oxazolidin-3-yl]hexyl}oxy)butyl]benzenesulfonamide was prepared using methods similar to those described in Example 1 viii. ES+ve 716 (MH)⁺ iii) N-[4-(Aminosulfonyl)phenyl]-3-{4-[(6-{[(2R)-2-(2,2-dimethyl-4H-1,3-benzodioxin-6-yl)-2-hydroxyethyl]amino}hexyl)oxy]butyl}benzenesulfonamide was prepared using methods similar to those described in Example 1 ix. ES+ve 690 (MH)⁺ iv) N-[4-(Aminosulfonyl)phenyl]-3-(4-{[6-({(2R)-2-hydroxy-2-[4-hydroxy-3-(hydroxymethyl)phenyl]ethyl}amino)hexyl]oxy}butyl)benzenesulfonamide acetate was prepared using methods similar to those described in Example 1 x. LCMS RT=2.61 min, ES+ve 650 (MH)⁺

Example 33

2-(Hydroxymethyl)-4-{(1R)-1-hydroxy-2-[(6-{-4-[3-(piperazin-1-ylsulfonyl)phenyl]butoxy}hexyl)amino]ethyl}phenol acetate i) (5R)-5-(2,2-Dimethyl-4H-1,3-benzodioxin-6-yl)-3-[6-({4-[3-(piperazin-1-ylsulfonyl)phenyl]but-3-ynyl}oxy)hexyl]-1,3-oxazolidin-2-one was prepared using methods similar to those described in Example 1 vii. ES+ve 626 (MH)$^+$ ii) (5R)-5-(2,2-Dimethyl-4H-1,3-benzodioxin-6-yl)-3-(6-{4-[3-(piperazin-1-ylsulfonyl)phenyl]butoxy}hexyl)-1,3-oxazolidin-2-one was prepared using methods similar to those described in Example 1 viii. ES+ve 630 (MH)$^+$ iii) (1R)-1-(2,2-Dimethyl-4H-1,3-benzodioxin-6-yl)-2-[(6-{4-[3-(piperazin-1-ylsulfonyl)phenyl]butoxy}hexyl)amino]ethanol was prepared using methods similar to those described in Example 1 ix. ES+ve 604 (MH)$^+$ iv) 2-(Hydroxymethyl)-4-{(1R)-1-hydroxy-2-[(6-14-[3-(piperazin-1-ylsulfonyl)phenyl]butoxy}hexyl)amino]ethyl}phenol acetate was prepared using methods similar to those described in Example 1 x. LCMS RT=2.23 min, ES+ve 564 (MH)$^+$

Example 34

3-(4-{[6-({(2R)-2-Hydroxy-2-[4-hydroxy-3-(hydroxymethyl)phenyl]ethyl}amino)hexyl]oxy}butyl)-N-(1-methyl-1-phenylethyl)benzenesulfonamide acetate i) 3-[4-({6-[(5R)-5-(2,2-Dimethyl-4H-1,3-benzodioxin-6-yl)-2-oxo-1,3-oxazolidin-3-yl]hexyl}oxy)but-1-ynyl]-N-(1-methyl-1-phenylethyl)benzenesulfonamide was prepared using methods similar to those described in Example 1 vii. ES–ve 673 (M–H)$^-$ ii) 3-[4-({6-[(5R)-5-(2,2-Dimethyl-4H-1,3-benzodioxin-6-yl)-2-oxo-1,3-oxazolidin-3-yl]hexyl}oxy)butyl]-N-(1-methyl-1-phenylethyl)benzenesulfonamide was prepared using methods similar to those described in Example 1 viii. ES–ve 677 (M–H)$^-$ iii) 3-{4-[(6-{[(2R)-2-(2,2-Dimethyl-4H-1,3-benzodioxin-6-yl)-2-hydroxyethyl]-amino}hexyl)oxy]butyl}-N-(1-methyl-1-phenylethyl)benzenesulfonamide was prepared using methods similar to those described in Example 1 ix. ES+ve 653 (MH)$^+$ iv) 3-(4-{[6-({(2R)-2-Hydroxy-2-[4-hydroxy-3-(hydroxymethyl)phenyl]ethyl}-amino)hexyl]oxy}butyl)-N-(1-methyl-1-phenylethyl)benzenesulfonamide acetate was prepared using methods similar to those described in Example 1 x. LCMS RT=2.90 min, ES+ve 613 (MH)$^+$

Example 35

5-(4-{[6-({(2R)-2-Hydroxy-2-[4-hydroxy-3-(hydroxymethyl)-phenyl]ethyl}amino)hexyl]oxy}butyl)-2-methoxybenzenesulfonamide acetate i) 5-[4-({6-[(5R)-5-(2,2-Dimethyl-4H-1,3-benzodioxin-6-yl)-2-oxo-1,3-oxazolidin-3-yl]hexyl}oxy)but-1-ynyl]-2-methoxybenzenesulfonamide was prepared using methods similar to those described in Example 1 vii. ES+ve 587 (MH)$^+$ ii) 5-[4-({6-[(5R)-5-(2,2-Dimethyl-4H-1,3-benzodioxin-6-yl)-2-oxo-1,3-oxazolidin-3-yl]hexyl}oxy)butyl]-2-methoxybenzenesulfonamide was prepared using methods similar to those described in Example 1 viii. ES+ve 591 (MH)$^+$ iii) 5-{4-[(6-{[(2R)-2-(2,2-Dimethyl-4H-1,3-benzodioxin-6-yl)-2-hydroxyethyl]amino}hexyl)oxy]butyl}-2-methoxybenzenesulfonamide was prepared using methods similar to those described in Example 1 ix. ES+ve 565 (MH)$^+$ iv) 5-(4-{[6-({(2R)-2-Hydroxy-2-[4-hydroxy-3-(hydroxymethyl)phenyl]ethyl}amino)hexyl]oxy}butyl)-2-methoxybenzenesulfonamide acetate was prepared using methods similar to those described in Example 1 x. LCMS RT=2.41 min, ES+ve 525 (MH)$^+$

Example 36

(E)-2-[3-(4-{[6-({(2R)-2-Hydroxy-2-[4-hydroxy-3-(hydroxymethyl)phenyl]ethyl}amino)hexyl]oxy}butyl)phenyl]-N-methylethenesulfonamide i) 4-(3-Bromophenyl)but-3-yn-1-ol A stirred, cooled solution of 1-bromo-3-iodobenzene (31 g) and 3-butyn-ol (7 ml) in acetonitrile (100 ml) and triethylamine (100 ml) was purged with nitrogen for 20 min under nitrogen. Dichlorobis(triphenylphosphine)palladium (500 mg) and cuprous iodide (800 mg) were added. The mixture was stirred for 18 h and then the solvent was removed invacuo. The residual oil was triturated with ethyl acetate (200 ml) and filtered. The filtrate was evaporated to dryness and the residue was purified by chromatography on Biotage (90 g) eluting with light petroleum 40-60°-diethyl ether (3:2) to give the title compound (21 g). LCMS RT=3.26 min.

ii) 4-(3-Bromophenyl)butan-1-ol

A solution of 4-(3-bromophenyl)but-3-yn-1-ol (21 g) in ethanol (1000 ml) was hydrogenated over platinum oxide iii) 1-Bromo-3-{4-[(6-bromohexyl)oxy]butyl}benzene

A stirred mixture of 4-(3-bromophenyl)butan-1-ol (18 g) and 1,6 dibromohexane (48 ml) in 50% aq. sodium hydroxide (500 ml) with tetrabutylammonium bromide (1.5 g) was stirred for 2d at 20°. The mixture was poured into water (1000 ml) and extracted into ethyl acetate (3×500 ml). The combined extracts were washed with water (1000 ml), dried ($Na_2SO_4$). The solvent was removed in-vacuo and the residual oil was purified by flash chromatography (500 g) using dichloromethane as eluent, changing to light petroleum (40-60°)-diethyl ether (9:1) to give the title compound (18 g). LCMS RT=4.34 min.

iv) (5R)-3-{6-[4-(3-Bromophenyl)butoxy]hexyl}-5-(2,2-dimethyl-4H-1,3-benzodioxin-6-yl)-1,3-oxazolidin-2-one Sodium hydride (60% dispersion in oil, 690 mg) was added to a stirred solution of 5R-(2,2-dimethyl-4H-1,3-benzodioxin-6yl)-1,3-oxazolidin-2-one (3.0 g) in dry DMF (35 ml) at 5° C. under nitrogen. After 20 min a solution of 1-bromo-3-{4-[(6-bromohexyl)oxy]butyl}benzene (5.64 g) in dry DMF (15 ml) was added. The mixture was stirred at ambient temperature for 4 h. The mixture was poured into an ammonium chloride solution (300 ml) and extracted into ethyl acetate (3×100 ml). The combined extracts were washed with water (200 ml), dried ($Na_2SO_4$) and evaporated. The residual oil was purified by chromatography on Biotage (90 g) eluting with diethyl ether-light petroleum (bp 40-60) (4:1) to give the title compound (5.2 g). LCMS RT=4.13 min.

v) (E)-2-{3-[4-({6-[(5R)-5-(2,2-Dimethyl-4H-1,3-benzodioxin-6-yl)-2-oxo-1,3-oxazolidin-3-yl]hexyl}oxy)butyl]phenyl}-N-methylethenesulfonamide A stirred mixture (5R)-3-{6-[4-(3-bromophenyl)butoxy]hexyl}-5-(2,2-dimethyl-4H-1,3-benzodioxin-6-yl)-1,3-oxazolidin-2-one (1.0 g), N-methylethenesulphonamide (WO 95/09166), (462 mg), tri-o-tolylphosphine (200 mg), palladium acetate (165 mg) and triethylamine (5 ml) in dry DMF (15 ml) was heated at 90° C. for 18 h. The mixture was cooled and filtered. The filtrate was poured into water (200 ml) and extracted into ethyl acetate (3×50 ml). The combined extracts were washed with water (100 ml) and ($Na_2SO_4$) and evaporated in vacuo. The residual oil was purified by chromatography on Biotage (40 g) eluting with diethyl ether-ethyl acetate (9:1) to give the title compound (220 mg). LCMS RT=3.70 min.

vi) (E)-2-(3-{4-[(6-{[(2R)-2-(2,2-Dimethyl-4H-1,3-benzodioxin-6-yl)-2-hydroxyethyl]amino}hexyl)oxy]butyl}phenyl)-N-methylethenesulfonamide Was prepared using methods similar to those described in Example 1ix.
LCMS RT=2.96 min vii) (E)-2-[3-(4-{[6-({(2R)-2-Hydroxy-2-[4-hydroxy-3-(hydroxymethyl)phenyl]ethyl}amino)hexyl]oxy}butyl)phenyl]-N-methylethenesulfonamide A solution of (E)-2-(3-{4-[(6-{[(2R)-2-(2,2-dimethyl-4H-1,3-benzodioxin-6-yl)-2-hydroxyethyl]amino}hexyl)oxy]butyl}phenyl)-N-methylethenesulfonamide (100 mg) in methanol (15 ml) was administered onto a Bond Elut SCX2 cartridge (10 g), which had been preconditioned in methanol. The cartridge was eluted with methanol (2×25 ml) followed by 15% aq. ammonia-methanol (2×20 ml). Evaporation of the latter fractions gave the title compound (70 mg) LCMS RT=2.59 min, ES+ve 535 (MH)+ viii) (E)-2-[3-(4-{[6-({(2R)-2-Hydroxy-2-[4-hydroxy-3-(hydroxymethyl)phenyl]ethyl}amino)hexyl]oxy}butyl)phenyl]-N-methylethanesulfonamide compound with (2E)-but-2-enedioic acid (1:1)

A solution of (E)-2-[3-(4-{[6-({(2R)-2-hydroxy-2-[4-hydroxy-3-(hydroxymethyl)phenyl]ethyl}amino)hexyl]oxy}butyl)phenyl]-N-methylethenesulfonamide (60 mg) and fumaric acid (6.5 mg) in ethanol was evaporated to dryness to give the title compound (66 mg) LCMS RT=2.65 min, ES+ve 537 (MH)$^+$

Example 37

2-[3-(4-{[6-({(2R)-2-Hydroxy-2-[4-hydroxy-3-(hydroxymethyl)phenyl]ethyl}amino)hexyl]oxy}butyl)phenyl]ethanesulfonamide i) tert-Butyl vinylsulfonylcarbamate

Di-tert-butyldicarbonate (8.62 g) was added to a stirred, cooled (ice bath) solution of ethenesulphonamide (S. Hirooka, *Bull. Chem. Soc. Jpn*. 1991, 64, 1431) (3.4 g), 4-(dimethylamino)pyridine (410 mg) and triethylamine (7 ml) in dichloromethane (40 ml) under nitrogen. The solution was stirred for 30 min, washed with 2M hydrochloric acid (30 ml), water (50 ml) and dried ($Na_2SO_4$) to give the title compound (5.0 g). Tlc ($SiO_2$, 1:1 diethyl ether-cyclohexane) Rf=0.4.

ii) (E)-2-{3-[4-({6-[(5R)-5-(2,2-Dimethyl-4H-1,3-benzodioxin-6-yl)-2-oxo-1,3-oxazolidin-3-yl]hexyl}oxy)butyl]phenyl}ethenesulfonamide Was prepared using methods similar to those described in Example 36 v. LCMS RT=3.6 min iii) (E)-2-(3-{4-[(6-{[(2R)-2-(2,2-Dimethyl-4H-1,3-benzodioxin-6-yl)-2-hydroxyethyl]amino}hexyl)oxy]butyl}phenyl)ethenesulfonamide Was prepared using methods similar to those described in Example 1 ix.
LCMS RT=2.87 min iv) (E)-2-[3-(4-{[6-({(2R)-2-Hydroxy-2-[4-hydroxy-3-(hydroxymethyl)phenyl]ethyl}amino)hexyl]oxy}butyl)phenyl]ethenesulfonamide Was prepared using methods similar to those described in Example 1 x.
LCMS RT=2.55 min v) 2-[3-(4-{[6-({(2R)-2-Hydroxy-2-[4-hydroxy-3-(hydroxymethyl)phenyl]ethyl}amino)hexyl]oxy}butyl)phenyl]ethanesulfonamide Was prepared using methods similar to those described in Example 1 viii.
LCMS RT=2.73 min, ES+ve 523 (MH)$^+$ Example 38

5-(4-{[6-({(2R)-2-Hydroxy-2-[4-hydroxy-3-(hydroxymethyl)phenyl]ethyl}amino)hexyl]oxy}butyl)[1,1'-biphenyl]-3-sulfonamide acetate i) tert-Butyl (3,5-diiodophenyl)sulfonylcarbamate Di tert-butyl dicarbonate (1.11 g) was added to a stirred solution of 3,5 di-iodo-benzenesulfonamide (Tsatsas, *Chem. Chron.* 1974, 3, 143) (1.6 g), 4-(dimethylamino)pyridine (50 mg) and triethylamine (0.8 ml) in dichloromethane (30 ml) at 5°. The solution was stirred at ambient temperature for 1 h, washed with 1M hydrochloric acid (30 ml), water (50 ml) and dried (Na$_2$SO$_4$). The solvent was evaporated to give the title compound (1.6 g). LCMS RT=4.24 min.

ii) tert-Butyl (3,5-diiodophenyl)sulfonyl{[2-(trimethylsilyl)ethoxy]methyl}carbamate Sodium hydride (60% dispersion in oil, 157 mg) was added to a stirred solution of tert-butyl (3,5-diiodophenyl)sulfonylcarbamate (1.6 g) in DMF (10 ml) at 5° under nitrogen. After 10 min 2-(trimethylsilyl)ethoxymethyl chloride (0.61 ml) was added. The mixture was stirred for 30 min. The reaction mixture was poured into aq. ammonium chloride (100 ml) and extracted into diethyl ether (3×40 ml). The organic extracts were washed with water (30 ml), dried (Na$_2$SO$_4$) and evaporated to give the title compound (1.95 g). LCMS RT=4.47 min.

iii) tert-Butyl {3-[4-({6-[(5R)-5-(2,2-dimethyl-4H-1,3-benzodioxin-6-yl)-2-oxo-1,3-oxazolidin-3-yl]hexyl}oxy)but-1-ynyl]-5-iodophenyl}sulfonyl{[2-(trimethylsilyl)ethoxy]methyl}carbamate A solution of (5R) 3-[6-(but-3-ynyloxy)hexyl]-5-(2,2-dimethyl-4H-1,3-benzodioxin-6-yl)-1,3-oxazolidin-2-one (233 mg) and tert-butyl (3,5-diiodophenyl)sulfonyl{[2-(trimethylsilyl)ethoxy]methyl}carbamate (410 mg) in dry acetonitrile (3 ml) and triethylamine (3 ml) was purged with nitrogen for 30 min. Cuprous iodide (50 mg) and dichlorobis(triphenylphosphine)palladium (50 mg) were then added. The mixture was stirred for 18 h at ambient temperature and then evaporated to dryness. The residual oil was purified by chromatography on Biotage (8 g) eluting with diethyl ether-petroleum ether (bp 40-60°). The appropriate fractions were evaporated to give the title compound (190 mg). LCMS RT=4.54 min.

iv) 3-[((tert-Butoxycarbonyl){[2-(trimethylsilyl)ethoxy]methyl}amino)sulfonyl]-5-[4-({6-[(5R)-5-(2,2-dimethyl-4H-1,3-benzodioxin-6-yl)-2-oxo-1,3-oxazolidin-3-yl]hexyl}oxy)but-1-ynyl]-1,1'-biphenyl A stirred mixture of tert-butyl {3-[4-({6-[(5R)-5-(2,2-dimethyl-4H-1,3-benzodioxin-6-yl)-2-oxo-1,3-oxazolidin-3-yl]hexyl}oxy)but-1-ynyl]-5-iodophenyl}sulfonyl {[2-(trimethylsilyl)ethoxy]methyl}carbamate (190 mg), benzeneboronic acid (62 mg) in dimethoxyethane (4 ml) and 1M sodium carbonate (2 ml) with tetrakis(triphenylphosphine)palladium (0) (25 mg) was heated at 80° for 1 h. The mixture was poured into water (20 ml) and extracted into ethyl acetate (3×30 ml). The organic extracts were dried (Na$_2$SO$_4$) and evaporated. The residual oil was purified by chromatography on Biotage (8 g) eluting with cyclohexane-diethyl ether (4:1) to give the title compound (140 mg). LCMS RT=4.54 min.

v) 3-[((tert-Butoxycarbonyl){[2-(trimethylsilyl)ethoxy]methyl}amino)sulfonyl]-5-[4-({6-[(5R)-5-(2,2-dimethyl-4H-1,3-benzodioxin-6-yl)-2-oxo-1,3-oxazolidin-3-yl]hexyl}oxy)butyl]-1,1'-biphenyl was prepared using methods similar to those described in Example 1 viii.
LCMS RT=4.55 min.

vi) 5-{4-[(6-{[(2R)-2-(2,2-Dimethyl-4H-1,3-benzodioxin-6-yl)-2-hydroxyethyl]amino}hexyl)oxy}butyl)[1,1'-biphenyl]-3-sulfonamide Was prepared using methods similar to those described in Example 1 ix. LCMS RT=2.86 min.

vii) 5-(4-{[6-({(2R)-2-Hydroxy-2-[4-hydroxy-3-(hydroxymethyl)phenyl]ethyl}amino)hexyl]oxy}butyl)[1,1'-biphenyl]-3-sulfonamide acetate Was prepared using methods similar to those described in Example 1 x. LCMS RT=2.76 min, ES+ve 571(MH)$^+$.

Example 39

3-(4-{[6-({(2R)-2-Hydroxy-2-[4-hydroxy-3-(hydroxymethyl)phenyl]ethyl}-amino)hexyl]oxy}butyl)-5-pentylbenzenesulfonamide acetate i) tert-Butyl {3-[4-({6-[(5R)-5-(2,2-dimethyl-4H-1,3-benzodioxin-6-yl)-2-oxo-1,3-oxazolidin-3-yl]hexyl}oxy)but-1-ynyl]-5-pent-1-ynylphenyl}sulfonyl{[2-(trimethylsilyl)ethoxy]methyl}carbamate Was prepared using methods similar to those described in Example 1 vii. LCMS RT=4.77 min.

ii) tert-Butyl {3-[4-({6-[(5R)-5-(2,2-dimethyl-4H-1,3-benzodioxin-6-yl)-2-oxo-1,3-oxazolidin-3-yl]hexyl}oxy)butyl]-5-pentylphenyl}sulfonyl{[2-(trimethylsilyl)ethoxy]methyl}carbamate Was prepared using methods similar to those described in Example 1 viii. LCMS RT=4.7 min.

iii) 3-{4-[(6-{[(2R)-2-(2,2-Dimethyl-4H-1,3-benzodioxin-6-yl)-2-hydroxyethyl]amino}hexyl)oxy]butyl}-5-pentylbenzenesulfonamide Was prepared using methods similar to those described in Example 1 ix. LCMS RT=3.21 min.

iv) 3-(4-{[6-({(2R)-2-Hydroxy-2-[4-hydroxy-3-(hydroxymethyl)phenyl]ethyl}-amino)hexyl]oxy}butyl)-5-pentylbenzenesulfonamide acetate Was prepared using methods similar to those described in Example 1 x
LCMS RT=2.93 min, ES+ve 565 (MH)+

Example 40

3-(4-{[6-({(2R)-2Hydroxy-2-[4-hydroxy-3-(hydroxymethyl)phenyl]ethyl}aminohexyl]oxy}butyl)benzenesulfonamide (i) 6-(But-3-ynyloxy)hexanal 6-Bromohexylbut-3-ynyl ether (DE3513885A1) (525 mg) in DMSO (2 ml) was added to a mixture of sodium bicarbonate (1 g) in DMSO (8 ml) at 150° C. with vigorous stirring and nitrogen bubbling through the solution. The mixture was stirred for 20 min at 150° C. and then allowed to cool to room temperature, diluted with diethyl ether and washed with water. The aqueous layer was extracted with diethyl ether and the combined ether layers were washed with dilute hydrochloric acid, brine, dried (MgSO$_4$) and evaporated to dryness to give the title compound (325 mg): IR 1726 cm$^{-1}$ MS(TSP+ve) m/z 186 (M+MH$_4$)$^+$.

(ii) (1R)-2-{[6-(But-3-ynyloxy)hexyl][(1S)-2-hydroxy-1-phenylethyl]amino}-1-(2,2-dimethyl-4H-1,3-benzodioxin-6-yl)ethanol A mixture of 6-(but-3-ynyloxy)hexanal (434 mg) and (1R)-1-(2,2-dimethyl-4H-1,3-benzodioxin-6-yl)-2-{[(1S)-2-hydroxy-1-phenylethyl]amino}ethanol (710 mg) (WO/0196278) in chloroform (10 ml) was treated at 20° C. with sodium triacetoxyborohydride (866 mg) and stirred under nitrogen for 2 days. The mixture was diluted with ethyl acetate and aqueous sodium bicarbonate solution. The organic phase was separated and washed with sodium bicarbonate solution, brine, dried and purified on a silica Bond Elut cartridge (10 g) eluting with dichloromethane, diethyl ether and finally ethyl acetate to give the title compound (810 mg): LCMS RT=2.69 min, ES+ve m/z 496 (M+H)+.

(iii) 3-{4-[(6-{[(2R)-2-(2,2-Dimethyl-4H-1,3-benzodioxin-6-yl)-2-hydroxyethyl][(1S)-2-hydroxy-1-phenylethyl]amino}hexyl)oxy]but-1-ynyl}benzenesulfonamide was prepared using methods similar to those described in Example 1 vii.
LCMS RT=2.85 min (iv) 3-(4-{[6-({(2R)-2Hydroxy-2-[4-hydroxy-3-(hydroxymethyl)phenyl]ethyl}aminohexyl]oxy}butyl)benzenesulfonamide 3-{4-[(6-{[(2R)-2-(2,2-Dimethyl-4H-1,3-benzodioxin-6-yl)-2-hydroxyethyl][(1S)-2-hydroxy-1-phenylethyl]amino}hexyl)oxy]but-1-ynyl}benzenesulfonamide (104 mg) was hydrogenated in ethanol (50 ml) over Pearlman's catalyst (60 mg) over 4 h and then over 10% Pd/C (100 mg) over 4 days. The catalyst was removed by filtration and washed with ethanol. The filtrate was concentrated and then applied to an SCX-2 cartridge eluting with methanol, followed by 0.67M ammonia in methanol. The ammonia fractions were concentrated and purified by chromatography on Biotage (4 g cartridge) eluting with dichloromethane-methanol-2M ammonia in methanol (50:8: 1) to give the title compound (11 mg) LCMS RT=2.34 min ES+ve 495 (M+H)+.

Example 41

3-Fluoro-5-(4-{[6-({(2R)-2-hydroxy-2-[4-hydroxy-3-(hydroxymethyl)phenyl]ethyl}amino)hexyl]oxy}butyl)benzenesulfonamide i) 3-Fluoro-5-iodobenzenesulfonamide 3-Fluoro-5-iodoaniline (3.06 g) (WO 9623783) was added to a stirred mixture of concentrated hydrochloric acid (4 ml) and water (4 ml). Glacial acetic acid (8 ml) was added and the reaction mixture cooled to −5° C. A solution of sodium nitrite (0.99 g) in water (8 ml) was added dropwise maintaining the temperature between −5° C. and −2° C. After the addition was complete the reaction was stirred for 10 min. In the meantime glacial acetic acid (20 ml) was saturated with sulfur dioxide gas for 0.25 h, then copper(I) chloride (0.353 g) was added. Additional sulfur dioxide was bubbled through the solution until a fine suspension was obtained. The mixture was cooled to 5° C. and then treated portionwise with the diazonium salt prepared above. After stirring at room temperature for 1 h ice (50 g) was added. The mixture was extracted with ether (100 ml) and the organic phases washed with NaHCO$_3$ solution (2×100 ml) then water (100 ml), dried (MgSO$_4$) and concentrated. The residue was dissolved in THF (30 ml) at 0° C. and aqueous ammonia (0.880; 5 ml) was added. After stirring at room temperature the mixture was partitioned between EtOAc (100 ml) and water (100 ml). The organic phase was washed with brine (50 ml), dried (MgSO$_4$) and concentrated. The residue was purified by chromatography using cyclohexane-EtOAc (5:1 then 3:1). Evaporation of the fractions and trituration of the residue with cyclohexane afforded the title compound (0.886 g). ES−ve 299 (M−H)− ii) 3-[4-({6-[(5R)-5-(2,2-Dimethyl-4H-1,3-benzodioxin-6-yl)-2-oxo-1,3-oxazolidin-3-yl]hexyl}oxy)but-1-ynyl]-5-fluorobenzenesulfonamide was prepared using methods similar to those described in Example 1 vii. ES+ve 575 (MH)+ iii) 3-[4-({6-[(5R)-5-(2,2-Dimethyl-4H-1,3-benzodioxin-6-yl)-2-oxo-1,3-oxazolidin-3-yl]hexyl}oxy)butyl]-5-fluorobenzenesulfonamide was prepared using methods similar to those described in Example 1 viii. ES+ve 579 (MH)+ iv) 3-{4-[(6-{[(2R)-2-(2,2-Dimethyl-4H-1,3-benzodioxin-6-yl)-2-hydroxyethyl]amino}hexyl)oxy]butyl}-5-fluorobenzenesulfonamide was prepared using methods similar to those described in Example 1 ix. ES+ve 553 (MH)+ v) 3-Fluoro-5-(4-{[6-({(2R)-2-Hydroxy-2-[4-hydroxy-3-(hydroxymethyl)phenyl]ethyl}amino)hexyl]oxy}butyl)benzenesulfonamide was prepared using methods similar to those described in Example 36 vii. LCMS RT=2.50 min, ES+ve 513 (MH)+

Example 42

5-(4-{[6-({(2R)-2-Hydroxy-2-[4-hydroxy-3-(hydroxymethyl)phenyl]ethyl}amino)hexyl]oxy}butyl)-3-trifluoromethylbenzenesulfonamide i) 3-Bromo-5-trifluoromethylbenzenesulfonamide was prepared using methods similar to those described in Example i. ES−ve 302,304 (M−H)⁻ ii) 3-[4-({6-[(5R)-5-(2,2-Dimethyl-4H-1,3-benzodioxin-6-yl)-2-oxo-1,3-oxazolidin-3-yl]hexyl}oxy)but-1-ynyl]-5-(trifluoromethyl)benzenesulfonamide was prepared using methods similar to those described in Example 6 i. ES+ve 625 (MH)⁺ iii) 3-[4-({6-[(5R)-5-(2,2-Dimethyl-4H-1,3-benzodioxin-6-yl)-2-oxo-1,3-oxazolidin-3-yl]hexyl}oxy)butyl]-5-trifluoromethylbenzenesulfonamide was prepared using methods similar to those described in Example 1 viii. ES+ve 629 (MH)⁺ iv) 3-{4-[(6-{[(2R)-2-(2,2-Dimethyl-4H-1,3-benzodioxin-6-yl)-2-hydroxyethyl]amino}hexyl)oxy]butyl}-5-(trifluoromethyl)benzenesulfonamide was prepared using methods similar to those described in Example 1 ix. ES+ve 603 (MH)⁺ v) 3-(4-{[6-({(2R)-2-Hydroxy-2-[4-hydroxy-3-(hydroxymethyl)phenyl]ethyl}amino)hexyl]oxy}butyl)-5-(trifluoromethyl)benzenesulfonamide was prepared using methods similar to those described in Example 36 vii. LCMS RT=2.57 min, ES+ve 563 (MH)⁺

Example 43

3-(4-{[6-({(2R)-2-Hydroxy-2-[4-hydroxy-3-(hydroxymethyl)phenyl]ethyl}amino)hexyl]oxy}butyl)-5-methylbenzenesulfonamide acetate i) 3-Bromo-5-methylbenzenesulfonamide was prepared from 3-bromo-5-methylaniline (EP303387A1) using methods similar to those described in Example 41(i). LCMS RT=2.80 min ii) 3-[4-({6-[(5R)-5-(2,2-Dimethyl-4H-1,3-benzodioxin-6-yl)-2-oxo-1,3-oxazolidin-3-yl]hexyl}oxy)but-1-ynyl]-5-methylbenzenesulfonamide was prepared using methods similar to those described in Example 1 vii. LCMS RT=3.54 min iii) 3-[4-({6-[(5R)-5-(2,2-Dimethyl-4H-1,3-benzodioxin-6-yl)-2-oxo-1,3-oxazolidin-3-yl]hexyl}oxy)butyl]-5-methylbenzenesulfonamide was prepared using methods similar to those described in Example 1 viii. LCMS RT=3.60 min iv) 3-{4-[(6-{[(2R)-2-(2,2-Dimethyl-4H-1,3-benzodioxin-6-yl)-2-hydroxyethyl]amino}hexyl)oxy]butyl}-5-methylbenzenesulfonamide was prepared using methods similar to those described in Example 1 ix. LCMS RT=2.73 min v) 3-(4-{[6-({(2R)-2-Hydroxy-2-[4-hydroxy-3-(hydroxymethyl)phenyl]ethyl}amino)hexyl]oxy}butyl)-5-methylbenzenesulfonamide was prepared using methods similar to those described in Example 1 x. LCMS RT=2.43 min, ES+ve 509 (MH⁺)

Example 44

N-{[3-(4-{[6-({(2R)-2-Hydroxy-2-[4-hydroxy-3-(hydroxymethyl)phenyl]ethyl}amino)hexyl]oxy}butyl)phenyl]sulfonyl}glycine acetate N²-[(3-Iodophenyl)sulfonyl]glycinamide (3-Iodophenyl)sulphonyl chloride (0.303 g) was stirred with glycinamide hydrochloride (0.122 g) and diisopropylethylamine (0.3 ml) in DMF (4 ml) at 21° for 24 h. The mixture was evaporated to dryness and applied to a silica Bond Elut Cartridge (10 g). The cartridge was eluted with $CH_2Cl_2$, $Et_2O$ and EtOAc. This gave the title compound (0.146 g), LCMS RT=2.36 min, ES+ve 341 (MH)⁺ ii) N²-({3-[4-({6-[(5R)-5-(2,2-Dimethyl-4H-1,3-benzodioxin-6-yl)-2-oxo-1,3-oxazolidin-3-yl]hexyl}oxy)but-1-ynyl]phenyl}sulfonyl)glycinamide was prepared using methods similar to those in Example 1 vii LCMS RT=3.26 min, ES+ve 614 (MH)⁺ iii) N²-({3-[4-({6-[(5R)-5-(2,2-Dimethyl-4H-1,3-benzodioxin-6-yl)-2-oxo-1,3-oxazolidin-3-yl]hexyl}oxy)butyl]phenyl}sulfonyl)glycinamide was prepared using methods similar to those in Example 1 viii LCMS RT=3.23 min, ES+ve 618 (MH)⁺ iv) N-[(3-{-4-[(6-{[(2R)-2-(2,2-Dimethyl-4H-1,3-benzodioxin-6-yl)-2-hydroxyethyl]amino}hexyl)oxy]butyl}phenyl)sulfonyl]glycine was prepared using methods similar to those in Example 1 ix LCMS RT=2.70 min, ES+ve 593 (MH)⁺ v) N—F [3-(4-{[6-({(2R)-2-Hydroxy-2-[4-hydroxy-3-(hydroxymethyl)phenyl]ethyl}amino)hexyl]oxy}butyl)phenyl]sulfonyl]glycine acetate was prepared using methods similar to those in Example 1 x LCMS RT=2.38 min, ES+ve 553 (MH)⁺

Example 45

3-(4-{[6-({(2R)-2-Hydroxy-2-[4-hydroxy-3-(hydroxymethyl)phenyl]ethyl}amino)hexyl]oxy}butyl)benzenesulfonamide

(i) 6-Bromohexyl but-3-ynyl ether

A mixture of 50% w/v aqueous sodium hydroxide (2500 ml), 1,6-dibromohexane (2610 g) and tetra-butylammonium bromide (25 g) was warmed to 50° C., with stirring. But-3-yn-1-ol (500 g) was then added to the reaction mixture at such a rate as to ensure the content's temperature did not exceed 65° C. The reaction was left at 50° C. overnight before being cooled to room temperature. Tert-butyl methyl ether (2500 ml) and brine (2000 ml) was added to the cooled mixture and the layers allowed to separate. The ethereal layer was washed with water (2×2000 ml), brine (1×2000 ml), and then dried over anhydrous $MgSO_4$. The solution was filtered and concentrated under reduced pressure to give crude product as a liquid. This was further purified by fractional distillation using a 60 cm vacuum jacketed Vigreux column at ca. 0.5 mbar. The product was obtained in the fraction which boiled at 92-98° C., to give the title compound (518 g), LC RT=6.16, δ ($CDCl_3$) 3.55 (2H, t, J 6.9 Hz), 3.46 (2H, t, J 6.9 Hz), 3.41 (2H, t, J 6.9 Hz), 2.46 (2H, dt, J 2.5, 6.9 Hz), 1.98 (1H, t, J 2.5 Hz), 1.86 (2H, m), 1.59 (2H, m), 1.46 (2H, m), 1.38 (2H, m).

(ii) 3-{-4-[(6-Bromohexyl)oxy]but-1-ynyl}benzenesulfonamide

A mixture of 3-bromo-benzenesulfonamide (625 g), 6-bromohexyl but-3-ynyl ether (850.1 g), bis(triphenylphosphine)palladium (II) chloride (62.5 g), triphenylphosphine (18.1 g) and triethylamine (536.3 g) in tetrahydrofuran (6250 ml) was stirred under an atmosphere of nitrogen for 20 mins. Copper (I) iodide (12.5 g) was then added to give a dark red/brown mixture that was heated to 50° C. for 23 h. The reaction mixture was then cooled to room temperature and filtered through a short silica pad (100 g). The pad was washed with additional tetrahydrofuran (15.6 L) and the resulting solution then concentrated under reduced pressure to give crude product (1382 g) as a viscous oil. This was purified by chromatography (7 kg silica) eluting with 5:1 petroleum ether:ethyl acetate followed by 2:1 petroleum ether:ethyl acetate to give the title compound (932.9 g) as an oil, LC RT=5.69 min, δ ($DMSO-d_6$) 7.79 (1H, s), 7.76 (1H, d, J 7.6 Hz), 7.56 (2H, m), 7.42 (2H, m), 3.55 (2H, t, J 6.6 Hz), 3.49 (2H, t, J 6.6 Hz), 3.42 (2H, t, J 6.6 Hz), 2.68 (2H, t, J 6.6 Hz), 1.76 (2H, m), 1.50 (2H, m), 1.35 (4H, m).

(iii) 3-{4-[(6-Bromohexyl)oxy]butyl}benzenesulfonamide

3-{4-[(6-Bromohexyl)oxy]but-1-ynyl}benzenesulfonamide (627 g) in IMS (1900 ml) was stirred with activated charcoal (314 g) at room temperature for 2 h and then filtered through a short pad of Celite. The filter pad was washed with IMS (4300 ml) and the filtrate transferred to a hydrogenation vessel. 5% Platinum on Charcoal (520.1 g, ~50% water) was added and the reaction mixture was then stirred under an atmosphere of hydrogen (0.2 bar) at 20° C. for 6 h. The mixture was then filtered through a short pad of Celite and concentrated under reduced pressure to give the title compound (499 g) as a solid, LC RT=5.66, δ ($DMSO-d_6$) 7.65 (1H, s), 7.64 (1H, d, J 9.2 Hz), 7.47 (1H, m), 7.42 (1H, m), 7.31 (2H, s), 3.50 (2H, t, J 6.9 Hz), 3.34 (4H, m), 2.66 (2H, t, J 7.5 Hz), 1.78 (2H, m), 1.62 (2H, m), 1.49 (4H, m), 1.37 (2H, m), 1.30 (2H, m).

(iv) (1R) 2-Bromo-1-(2,2-dimethyl-4H-1,3-benzodioxin-6-yl)ethanol

A solution R-diphenylprolinol (75 mg) in THF (2 ml) was treated with borane-THF (1M, 20.5 ml) over 20 min at 20° C. under nitrogen. After the addition was complete the solution was kept between 30 and 35° C. for 1 h and then cooled in ice and 2-bromo-1-(2,2-dimethyl-4H-1,3-benzodioxin-6-yl) ethanone (DE3513885) (3.9 g) in THF (10 ml) was added over 1.5 h keeping the temperature below 5° C. The mixture was stirred under nitrogen for a further 0.5 h and then methanol (4 ml) was added at 0° C. The solvent was removed under reduced pressure and the residue was purified by chromatography on flash silica gel eluting with ethyl acetate-cyclohexane (1:4) to give the title compound (3.31 g) δ ($CDCl_3$) 7.15 (1H, dd, J 8, 2 Hz), 7.03 (1H, br s), 6.82 (1H, d, J 8 Hz), 4.85 (3H, s and m), 3.61 (1H, dd, J 10,4 Hz), 3.50 (1H, dd, J 10, 9 Hz), 1.54 (6H, s).

(v) {[(1R)-2-Bromo-1-(2,2-dimethyl-4H-1,3-benzodioxin-6-yl)ethyl]oxy}(triethyl)silane Triethylsilyl chloride (205 g) was added dropwise to a stirred mixture of (1R)-2-Bromo-1-(2,2-dimethyl-4H-1,3-benzodioxin-6-yl)ethanol (350 g) and imidazole (108.5 g) in DMF (875 ml) at 5° C. Upon complete addition the mixture was warmed to 15° C. and stirred, at this temperature for 1 h. N-hexane (3500 ml) was then added to the mixture which was washed with water (3×750 ml). The organic layer was dried over anhydrous $MgSO_4$ before being filtered and concentrated under reduced pressure to give the title compound (488.6 g) as an oil, LC RT=7.97 min, δ ($DMSO-d_6$) 7.18 (1H, d, J 8.2 Hz), 7.10 (1H, s), 6.75 (1H, d, J 8.2 Hz), 4.83 (1H, m), 4.78 (2H, d, J 6.9 Hz), 3.55 (2H, m), 1.45 (6H, s), 0.84 (9H, t, J 8.1 Hz), 0.51 (6H, m).

(vi) N-benzyl-N-{(2R)-2-(2,2-dimethyl-4H-1,3-benzodioxin-6-yl)-2-[(triethylsilyl)oxy]ethyl}amine A mixture of {[(1R)-2-Bromo-1-(2,2-dimethyl-4H-1,3-benzodioxin-6-yl)ethyl]oxy}(triethyl)silane (130 g) and benzylamine (177 ml) in 1,4-dioxane (650 ml) was heated at 105° C. with stirring overnight. The mixture was then cooled to room temperature and water (150 ml) and diethyl ether (1200 ml) added. The layers were separated and the ethereal layer was washed with saturated ammonium chloride solution (3×600 ml), saturated sodium bicarbonate solution (200 ml) and then brine (200 ml). The solution was dried over anhydrous $Na_2SO_4$ before being filtered and concentrated under reduced pressure to give the title compound (129.9 g) as an oil, LC RT=5.20 min, δ ($CDCl_3$) 7.22 (5H, m), 7.02 (1H, d, J 8.7 Hz), 6.86 (1H, s), 6.68 (1H, d, J 8.3 Hz), 4.75 (2H, s), 4.69 (1H, m), 3.73 (2H, s), 2.70 (2H, m), 1.46 (6H, s), 0.79 (9H, m), 0.44 (6H, m).

(vii) (1R)-2-(Benzylamino)-1-(2,2-dimethyl-4H-1,3-benzodioxin-6-yl)ethanol

Tetrabutylammonium fluoride (395 ml, 1M in THF) was added dropwise to a stirred solution of N-benzyl-N-{(2R)-2-(2,2-dimethyl-4H-1,3-benzodioxin-6-yl)-2-[(triethylsilyl)oxy]ethyl}amine (129.9 g) in THF (900 ml) at 5° C. Upon complete addition the reaction mixture was maintained at this temperature for 15 min before water (600 ml) was added. The resulting slurry was diluted with diethyl ether (500 ml) and filtered. The filtrate was washed with water (2×500 ml) and brine (500 ml) before being dried over anhydrous $Na_2SO_4$. The resulting mixture was filtered and concentrated under reduced pressure to give a solid which was triturated with diisopropyl ether to give the title compound (70 g) as a solid, LC RT=3.34 min, δ ($CDCl_3$) 7.31 (5H, m), 7.09 (1H, d, J 8 Hz), 6.98 (1H, s), 6.77 (1H, d J 8 Hz), 4.82 (2H, s), 4.63 (1H, m), 3.83 (2H, d, J 4 Hz), 2.80 (2H, m), 1.52 (6H, s).

(viii) 3-{4-[(6-{Benzyl[(2R)-2-(2,2-dimethyl-4H-1, 3-benzodioxin-6-yl)-2-hydroxyethyl]amino}hexyl) oxy]butyl}benzenesulfonamide A stirred mixture of 3-{4-[(6-bromohexyl)oxy] butyl}benzenesulfonamide (11.1 g), (1R)-2-(benzylamino)-1-(2,2-dimethyl-4H-1,3-benzodioxin-6-yl)ethanol (9 g) and diisopropyl ethylamine (8.9 ml) in acetonitrile (28 ml) was heated at reflux for 18 h. The resulting mixture was cooled to room temperature, diluted with diethyl ether (250 ml) and washed with water (2×100 ml) and brine (100 ml) before being dried over anhydrous $Na_2SO_4$. The suspension was filtered and concentrated under reduced pressure to give the title compound (20 g) as an oil. LC RT=4.68 min, δ ($CDCl_3$) 7.70 (2H, m), 7.38 (2H, m), 7.29 (5H, m), 7.02 (1H, d, J 8.3 Hz), 6.91 (1H, s), 6.73 (1H, d, J 8.3 Hz), 4.79 (2H, s), 4.53 (1H, m), 3.87 (1H, m), 3.40 (5H, m), 2.69 (2H, t, J 7.2 Hz), 2.54 (2H, m), 2.43 (2H, m), 1.70 (2H, m), 1.60 (2H, m), 1.51 (10H, m), 1.25 (4H, m)

(ix) 3-(4-{[6-(Benzyl{(2R)-2-hydroxy-2-[4-hydroxy-3-(hydroxymethyl)phenyl]ethyl}amino)hexyl] oxy}butyl)benzenesulfonamide Hydrochloric acid (80 ml, 1M) was added dropwise to a stirred solution of 3-{4-[(6-{benzyl[(2R)-2-(2,2-dimethyl-4H-1,3-benzodioxin-6-yl)-2-hydroxyethyl]amino}hexyl) oxy]butyl}benzenesulfonamide (20 g) in ethanol (100 ml) at 0° C. Upon complete addition the mixture was stirred at 5° C. for 1 h before being allowed to warm to room temperature. A portion (50 ml) of the ethanol was removed under reduced pressure and the remaining mixture was diluted with ethyl acetate (250 ml). The mixture was then washed with water (100 ml), saturated sodium bicarbonate solution (100 ml) and brine (100 ml) before being dried over anhydrous $Na_2SO_4$. The suspension was filtered and concentrated under reduced pressure to give the title compound (16 g) as an oil. LC R=4.02 min, δ (DMSO-$d_6$) 9.15 (1H, s), 7.65 (1H, s), 7.64 (1H, d, J 8.8 Hz), 7.45 (2H, m), 7.27 (8H, m), 6.94 (1H, dd, J 8.2 Hz), 6.67 (1H, d, J 8.2 Hz), 4.92 (1H, t, J 5.7 Hz), 4.67 (1H, s), 4.56 (1H, m), 4.45 (2H, d, J 5.7 Hz), 3.61 (2H, m), 3.34 (2H, t, J 6.3 Hz), 3.28 (2H, t, J 6.2 Hz), 2.66 (2H, m), 2.50 (2H, m), 2.39 (2H, m), 1.61 (2H, m), 1.50 (2H, m), 1.39 (4H, m), 1.16 (4H, m).

(x) 3-(4-{[6-({(2R)-2-Hydroxy-2-[4-hydroxy-3-(hydroxymethyl)phenyl]ethyl}amino)hexyl]oxy}butyl) benzenesulfonamide 5% Pd/C (8 g, 50% wet) was added to a solution of 3-(4-{[6-(Benzyl{(2R)-2-hydroxy-2-[4-hydroxy-3-(hydroxymethyl)phenyl]ethyl}amino)hexyl]oxy}butyl)benzenesulfonamide (16 g) in IMS and the mixture was stirred under hydrogen for 6 h. The resulting suspension was filtered through a plug of Celite which was then washed with IMS (160 ml). The combined washings were concentrated under reduced pressure to give the title compound (12.8 g) as an oil, LC RT=3.51 min, δ ($CD_3OD$) 7.64 (1H, s), 7.61 (1H, m), 7.33 (2H, m), 7.20 (1H, s), 7.01 (1H, dd, J 2.2, 8.2 Hz), 6.65 (1H, d, J 8.2 Hz), 4.61 (1H, m), 4.54 (2H, s), 3.33 (4H, m), 2.72 (2H, m) 2.63 (2H, m), 2.57 (2H, m) 1.62 (2H, m), 1.46 (6H, m), 1.27 (4H, m).

Example 46

The following salts of the compound of Example 45 were prepared as described below.

(i) Cinnamate Salt

Cinnamic acid (0.3 g) was added to a solution of 3-(4-{[6-({(2R)-2-Hydroxy-2-[4-hydroxy-3-(hydroxymethyl)phenyl] ethyl}amino)hexyl]oxy}butyl)benzenesulfonamide (1.0 g) in methanol (5 ml) at room temperature. The solution was stirred for 5 minutes before being concentrated under reduced pressure to give a pale yellow gum. Water (10 ml) was added to the gum and the reulting suspension stirred at room temperature for 24 h. The suspension was then filtered to give the title compound as a white solid (0.72 g), which was then recrystallised from ethanol (SmI) to give a white solid (0.54 g) mp 127-128° C., δ ($CD_3OD$) 7.73 (1H, s), 7.71 (1H, d, J 7.5 Hz), 7.50 (2H, d, J 7 Hz), 7.41 (3H, m), 7.32 (4H, m), 7.16 (1H, dd, J 2.2, 8.2 Hz), 6.78 (1H, d, J 8.2 Hz), 6.49 (1H, d, J 16.4 Hz), 4.88 (1H, dd, J 3.8, 9.5 Hz), 4.65 (2H, s), 3.40 (4H, m), 3.10 (2H, m) 2.99 (2H, m), 2.69 (2H, t, J 7.5 Hz) 1.68 (4H, m), 1.55 (4H, m), 1.39 (4H, m).

(ii) 1-Hydoxynaphthoate Salt

Was prepared using methods similar to those quoted above, isolation from methanol/water gave the title compound as a white solid mp 60-69° C., δ ($CD_3OD$) 8.28 (1H, d, J 8.2 Hz), 7.85 (1H, d, J 8.8 Hz), 7.72 (3H, m), 7.48 (1H, m), 7.39 (4H, m), 7.19 (1H, d, J 8.8 Hz), 7.16 (1H, d, J 8.2 Hz), 6.78 (1H, d, J 8.2 Hz), 4.88 (1H, m), 4.65 (2H, s), 3.35 (4H, m), 3.10 (2H, m) 2.99 (2H, m), 2.66 (2H, t, J 7.5 Hz) 1.65 (4H, m), 1.51 (4H, m), 1.34 (4H, m).

(iii) 4-Phenylbenzoate Salt

Was prepared using methods similar to those quoted above, isolation from methanol/water gave the title compound as a white solid mp 134-136° C., δ ($CD_3OD$) 8.01 (2H, d, J 8.1 Hz), 7.73 (1H, s), 7.70 (1H, d, J 6.9 Hz), 7.62 (4H, m), 7.43 (4H, m), 7.34 (2H, m), 7.16 (1H, dd, J 2.6, 8.1 Hz), 6.78 (1H, d, J 8.1 Hz), 4.86 (1H, m), 4.64 (2H, s), 3.42 (4H, m), 3.08 (2H, m) 2.98 (2H, t, J 7.5 Hz), 2.71 (2H, t, J 7.5 Hz) 1.70 (4H, m), 1.57 (4H, m), 1.40 (4H, m).

(iv) Triphenylacetate Salt

Was prepared using methods similar to those quoted above, isolation from methanol/water gave the title compound as a white solid mp 99-102° C., δ ($CD_3OD$) 7.74 (1H, s), 7.70 (1H, d, J 6.2 Hz), 7.42 (2H, m), 7.32 (1H, s), 7.27 (6H, m), 7.19 (6H, m), 7.13 (4H, m), 6.77 (1H, d, J 8.2 Hz), 4.85 (1H, dd, J 4.4, 9.4 Hz), 4.65 (2H, s), 3.42 (4H, m), 3.04 (2H, m) 2.94 (2H, t, J 7.5 Hz), 2.72 (2H, t, J 7.5 Hz) 1.70 (4H, m), 1.57 (4H, m), 1.40 (4H, m).

(v) 4-Methyl Cinnamate Salt

Was prepared using methods similar to those quoted above, isolation from methanol/water gave the title compound as a white solid mp 110-113° C., δ (CD₃OD) 7.73 (1H, s), 7.71 (1H, d, J 7.5 Hz), 7.39 (6H, m), 7.16 (3H, m), 6.78 (1H, d, J 8.2 Hz), 6.45 (1H, d, J 15.7 Hz), 4.88 (1H, dd, J 3.8, 10.0 Hz), 4.65 (2H, s), 3.40 (4H, m), 3.10 (2H, m) 2.99 (2H, m), 2.68 (2H, t, J 7.5 Hz) 2.31 (3H, s), 1.68 (4H, m), 1.55 (4H, m), 1.39 (4H, m).

(vi) 4-Methoxy Cinnamate salt

Was prepared using methods similar to those quoted above, isolation from methanol/water gave the title compound as a white solid mp 115-118° C., δ (CD₃OD) 7.73 (1H, s), 7.71 (1H, d, J 6.9 Hz), 7.40 (5H, m), 7.35 (1H, s), 7.16 (1H, d, J 8.2 Hz), 6.89 (2H, d, J 8.8 Hz) 6.78 (1H, d, J 8.8 Hz), 6.37 (1H, d, J 16.4 Hz), 4.88 (1H, dd, J 3.2, 10.0 Hz), 4.65 (2H, s), 3.78 (3H, s), 3.40 (4H, m), 3.10 (2H, m) 2.99 (2H, m), 2.68 (2H, t, J 7.5 Hz) 1.68 (4H, m), 1.55 (4H, m), 1.39 (4H, m).

(vii) 3-(2-Naphthalenyl)-2-propanoate Salt

Was prepared using methods similar to those quoted above, isolation from methanol/water gave the title compound as a white solid mp 139-144° C., δ (CD₃OD) 7.91 (1H, s), 7.83 (3H, m), 7.72 (3H, m), 7.59 (1H, d, J 15.7 Hz), 7.47 (2H, m), 7.41 (2H, m), 7.34 (1H, s), 7.16 (1H, dd, J 2.5, 8.1 Hz), 6.78 (1H, d, J 8.1 Hz), 6.62 (1H, d, J 16.4 Hz), 4.85 (1H, m), 4.65 (2H, s), 3.40 (4H, m), 3.08 (2H, m) 2.98 (2H, m), 2.70 (2H, t, J 7.5 Hz) 1.69 (4H, m), 1.56 (4H, m), 1.39 (4H, m).

Example 47

3-(3-{[7-({(2R)-2-Hydroxy-2-[4-hydroxy-3-(hydroxymethyl)phenyl]ethyl}amino)heptyl]oxy}propyl)benzenesulfonamide (i) 7-Bromoheptyl prop-2-ynyl ether 25% (w/w) aq. NaOH (700 ml) was added to a stirred mixture of propargyl alcohol (70 g), tetra-butyl ammonium bromide (3.5 g) and 1,7-dibromoheptane (322 g) maintaining the temperature below 30° C. The reaction mixture was heated at 60° C. for 5 hrs then allowed to cool to room temperature and stirred overnight. Diethyl ether (350 ml) and water (280 ml) were added, the mixture stirred and allowed to settle. The aqueous layer was extracted with diethyl ether (210 ml), the organic layers combined, dried (MgSO₄). The solution was concentrated to give 280 g of crude material. 140 g Of the crude was purified by chromatography on Biotage (800 g) eluting with petroleum ether then petroleum ether:ethyl acetate (100:1 followed by 100:1.5) to give the title compound (49.6 g).
NMR-300 MHz-δ (CDCl₃)-4.05 (2H, d, J 2 Hz), 3.45 (2H, t, J 6.5 Hz), 3.35 (2H, t, J 7 Hz), 2.35 (1H, s), 1.8 (2H, m), 1.5 (2H, m), 1.3 (4H, m).

(ii) 3-{3-[(7-Bromoheptyl)oxy]prop-1-ynyl}benzenesulfonamide

7-Bromoheptyl prop-2-ynyl ether (55.1 g) in THF (250 ml) was added dropwise over ca 8 h to a stirred mixture of 3-bromobenzenesulfonamide (43.5 g), PdCl₂(PPh₃)₂ (6.48 g), PPh₃ (1.45 g), CuI (1.4 g) and Et₃N (52 ml) in THF (250 ml) at 55±5° C. under nitrogen then the mixture heated for a further ca 15 hrs. The reaction was cooled, filtered through Celite and the solids washed with THF. The solution was concentrated and the product purified by chromatography on flash silica gel (600 g) eluting with petroleum ether:ethyl acetate (ratios ranging successively from 19:1 to 7:3) to give the title compound (33 g)-LC RT=5.85 min.
NMR-300 MHz-δ (CDCl₃)-7.95 (1H, t, J 1.5 Hz), 7.78 (1H, dt, J 8, 2 Hz), 7.55 (1H, dt, J 7.75, 2 Hz), 7.40 (1H, t, J 8 Hz), 5.0 (2H, br s), 4.3 (2H, s), 3.4 (2H, t, J 6.5 Hz), 3.35 (2H, t, J 7.25 Hz), 1.75 (2H, m), 1.55 (2H, m), 1.3 (4H, m).

(iii) 3-{3-[(7-Bromoheptyl)oxy]propyl}benzenesulfonamide

3-{3-[(7-Bromoheptyl)oxy]prop-1-ynyl}benzenesulfonamide (29.4 g) was dissolved in Industrial Methylated Spirits (IMS) (300 ml). Nuchar charcoal (15 g, 50% w/w) was added and the suspension stirred at room temperature for ca 1.5 h. After filtering off the charcoal and washing the filtrate with IMS (60 ml) the solution was then treated in two separate lots: 5% Pd/C catalyst (11.25 g, 50% wet) was added to each, the mixtures hydrogenated at atmospheric pressure and temperature for ca 1-2 h, the catalyst filtered off, rinsed with IMS (ca 10 ml) and the filtrate concentrated to give the crude product as a solid which was recrystallised from diisopropyl ether (100 ml) to give the title compound as a solid (15.1 g)-LC RT=5.91 min.
NMR-300 MHz-δ (CDCl₃)-7.75 (2H, m), 7.45 (2H, m), 4.9 (2H, br s), 3.42 (6H, m), 2.8 (2H, t, J 7.5 Hz), 1.9 (4H, m), 1.65-1.55 (4H, m), 1.5-1.3 (4H, m).

(iv) 3-{3-[(7-{Benzyl [(2R)-2-(2,2-dimethyl-4H-1,3-benzodioxin-6-yl)-2-hydroxyethyl]amino}heptyl)oxy]propyl}benzenesulfonamide A mixture of (1R)-2-(benzylamino)-1-(2,2-dimethyl-4H-1,3-benzodioxin-6-yl)ethanol (55.8 g), 3-{3-[(7-bromoheptyl)oxy]propyl}benzenesulfonamide (63.65 g), N,N-diisopropylethylamine (55 ml) and acetonitrile (200 ml) was stirred and heated under N₂ at reflux for ca 21 h. The mixture was cooled to room temperature then diethyl ether (1000 ml) and water (500 ml) were added and the mixture stirred. The organic phase was washed with water (500 ml), then saturated brine (500 ml) and dried (Na₂SO₄). The solution was concentrated and the product purified by chromatography on flash silica gel (1000 g), eluting with petroleum ether:ethyl acetate (ratios ranging successively from 4:1 to 1:1) to give the title compound (97.7 g)-LC RT=1.54 min.
δ (DMSO-d₆)-7.75 (2H, m), 7.45 (1H, t, J 8 Hz), 7.4 (1H, m), 7.35 (2H, s), 7.25 (5H, m), 7.05 (1H, d, J 8.5 Hz), 7.0 (1H, s), 6.7 (1H, d, J 8.5 Hz), 4.9 (1H, br s), 4.78 (2H, s), 4.6 (1H, m), 3.65 (1H, d, J 13.8 Hz), 3.55 (1H, d, J 13.8 Hz), 3.4 (1H, br s), 3.3 (4H, m), 2.7 (2H, m), 2.55 (2H, m), 2.4 (2H, m), 1.85 (2H, m), 1.45 (8H, m), 1.35 (2H, m), 1.25 (2H, m), 1.15 (4H, m).

(v) 3-(3-{[7-(Benzyl{(2R)-2-hydroxy-2-[4-hydroxy-3-(hydroxymethyl)phenyl]ethyl}amino)heptyl]oxy}propyl)benzenesulfonamide To a stirred, ice-cooled solution of 3-{3-[(7-{Benzyl[(2R)-2-(2,2-dimethyl-4H-1,3-benzodioxin-6-yl)-2-hydroxyethyl]amino}heptyl)oxy]propyl}benzenesulfonamide (97.2 g) in IMS (417 ml) was gradually added aqueous 1M hydrochloric acid (417 ml) keeping the temperature below 15° C. The mixture was then stirred at room temperature for ca 5 h. Saturated sodium bicarbonate (417 ml) and ethyl acetate (1000 ml) were then added to the mixture. The organic layer was separated off, washed with water (400 ml), brine (400 ml) and finally dried (Na₂SO₄). Concentration in vacuo gave the title compound (87.9 g)-LC RT=4.01 min.

δ (CDCl₃)-7.75 (1H, br s), 7.70 (1H, m), 7.4-7.25 (8H, m), 7.0 (1H, d, J 8 Hz), 6.95 (1H, s), 6.75 (1H, d, J 8 Hz), 4.7 (2H, s), 4.55 (1H, m), 3.9 (1H, d, J 13 Hz), 3.55 (1H, d, J 13 Hz), 3.4 (4H, m), 2.75 (2H, t, J 7.5 Hz), 2.65 (1H, m), 2.55 (2H, d, J 7 Hz), 2.45 (1H, m), 1.87 (2H, m), 1.55 (4H, m), 1.3 (6H, m).

(vi) 3-(3-{[7-({(2R)-2-Hydroxy-2-[4-hydroxy-3-(hydroxymethyl)phenyl]ethyl}amino)heptyl]oxy}propyl)benzenesulfonamide 3-(3-{[7-(Benzyl{(2R)-2-hydroxy-2-[4-hydroxy-3-(hydroxymethyl)phenyl]ethyl}amino)heptyl]oxy}propyl)benzenesulfonamide (87.2 g) in methanol (800 ml) was hydrogenated over 5% Pd/C catalyst (28 g, 50% wet) at atmospheric pressure and ambient temperature. The catalyst was removed by filtration through a Hyflo pad and the filtrate concentrated in vacuo to give the title compound (64.4 g)-LC RT=3.46 min.

δ (DMSO-d₆)-7.65 (2H, m), 7.45 (2H, m), 7.25 (1H, s), 6.95 (1H, dd, J 8, 2 Hz), 6.67 (1H, d, J 8 Hz), 5.0 (2H, br m,), 4.45 (3H, m), 3.35 (4H, m), 3.15 (2H, m), 2.7 (2H, m), 2.55-2.45 (4H, m), 1.8 (2H, m), 1.5 (2H, m), 1.35 (2H, m), 1.25 (6H, m).

Example 48

(i) 3-(3-{[7-({(2R)-2-Hydroxy-2-[4-hydroxy-3-(hydroxymethyl)phenyl]ethyl}amino)heptyl]oxy}propyl)benzenesulfonamide(E)-3-(napthalen-2-yl)-2-propenoate 3-(3-{[7-({(2R)-2-Hydroxy-2-[4-hydroxy-3-(hydroxymethyl)phenyl]ethyl}amino)heptyl]oxy}propyl)benzenesulfonamide (1 g) was taken up in ethanol (6 ml) at room temperature with stirring and (E)-3-(napthalen-2-yl)-2-propenoic acid (0.39 g) added. The mixture was heated to ca 60° C. until a solution formed. The solution was cooled to room temperature and seed crystals of the title compound added. The mixture was aged for 65 h, the product filtered, washed with ethanol (1 ml) and dried to give the title compound (1.05 g) M Pt.=135° C.-146° C.

δ (MeOH-d₄) 7.95 (1H, s), 7.87 (3H, m), 7.75 (3H, m), 7.60 (1H, d, J 16 Hz), 7.45 (5H, m), 7.40 (1H, m), 6.8 (1H, d, J 8 Hz), 6.65 (1H, d, J 16 Hz), 4.9 (1H, m), 4.65 (2H, s), 3.4 (4H, m), 3.12 (2H, m), 3.05 (2H, br t, J 8 Hz), 2.75 (2H, t, J 8 Hz), 1.87 (2H, m), 1.72 (2H, m), 1.56 (2H, m), 1.40 (6H, m).

Alternatively:
3-(3-{[7-({(2R)-2-Hydroxy-2-[4-hydroxy-3-(hydroxymethyl)phenyl]ethyl}amino)heptyl]oxy}propyl)benzenesulfonamide (0.5 g), dissolved in methanol (10 ml) was treated with (E)-3-(napthalen-2-yl)-2-propenoic acid (0.194 g). The clear solution was evaporated to dryness and redissolved in ethanol (3 ml) and heated to reflux. The solution was allowed to cool to room temperature and after 48 h the product filtered, washed with ethanol (2 ml) and dried to give the title compound (0.58 g), M Pt 135-146° C.

(ii) 4-Phenylbenzoate Salt

In a similar fashion to the previous example, the title salt was prepared (0.5 g). The XRPD pattern of this product is shown in FIG. 1. δ (MeOH-d₄) 8.05 (2H, d, J 8 Hz), 7.75 (2H, m), 7.65 (4H, m), 7.45 (4H, m), 7.35 (2H, m), 7.17 (1H, d, J 8 Hz), 6.8 (1H, d, J 8 Hz), 4.9 (s), 4.65 (2H, s), 3.42 (4H, m), 3.12 (2H, m), 3.02 (2H, m), 2.80 (2H, t, J 8 Hz), 1.90 (2H, m), 1.72 (2H, m), 1.55 (2H, m), 1.40 (2H, br s).

(iii) Triphenylacetate Salt

Figure 2:
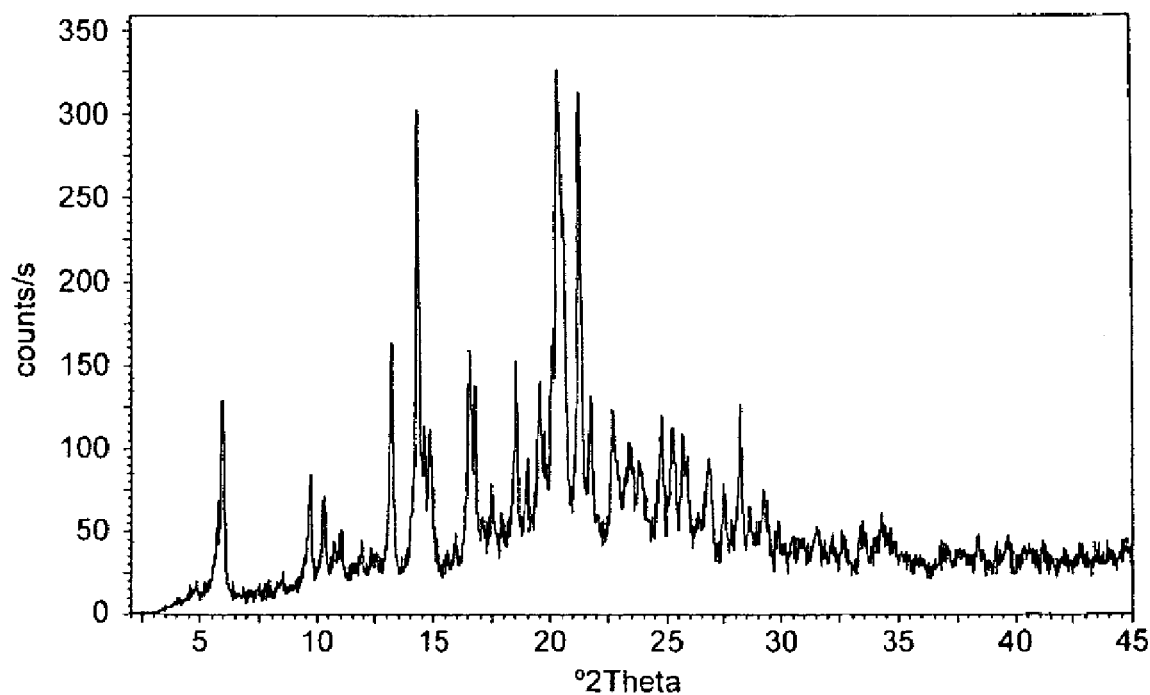
FIG. 2 illustrates the X-Ray Powder Diffraction (XRPD) pattern of the product referred to in Example 48(iii).

In a similar fashion, the title salt was prepared (0.485 g). The XRPD pattern of this product is shown in FIG. 2.

δ (MeOH-d₄) 7.86 (2H, m), 7.58 (2H, m), 7.48 (1H, m), 7.42 (6H, m), 7.35 (6H, m), 7.27 (4H, m), 6.92 (1H, d, J 8 Hz), 5.00 (m), 4.78 (2H, s), 3.55 (4H, m), 3.50 (1H, s), 3.20 (2H, m), 3.10 (2H, m), 2.92 (2H, m), 2.05 (2H, m), 1.80 (2H, m), 1.72 (2H, m), 1.5 (6H, m).

(iv) 4-Phenylcinnamate Salt

Figure 3:
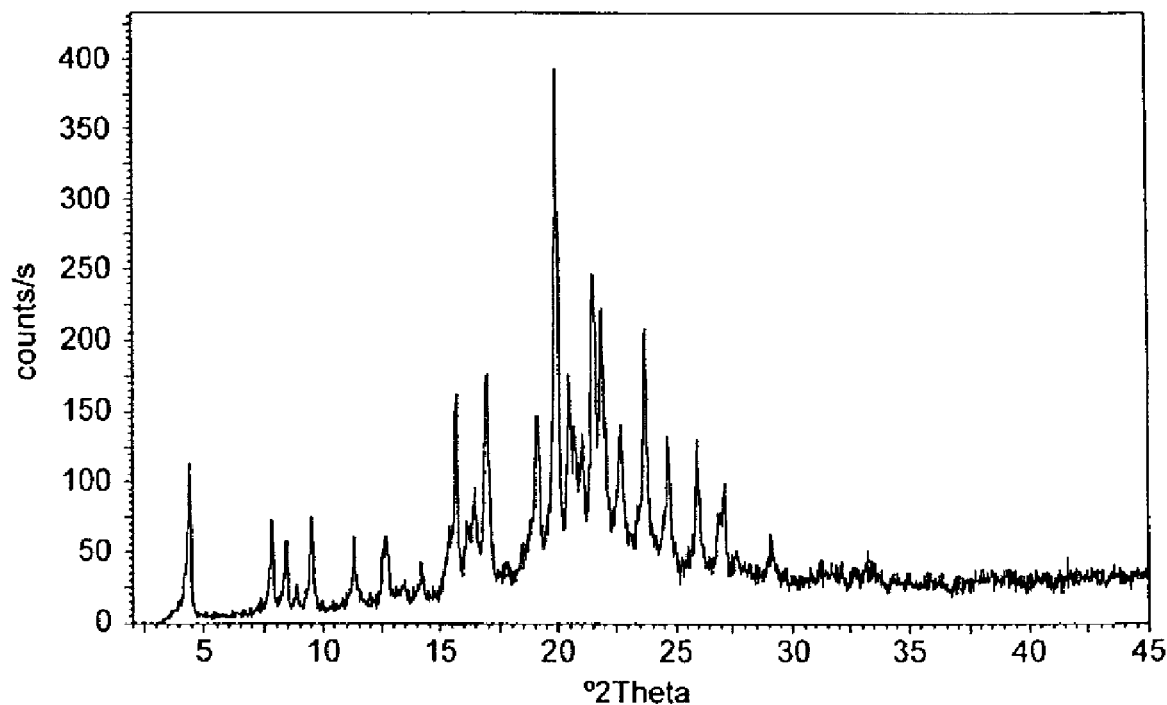
FIG. 3 illustrates the X-Ray Powder Diffraction (XRPD) pattern of the product referred to in Example 48(iv).

In a similar fashion the title salt was prepared (0.243 g). The XRPD pattern of this product is shown in FIG. 3. δ (MeOH-d₄) 7.7 (2H, m), 7.55 (6H, m), 7.35 (5H, m), 7.29 (2H, m), 7.1 (1H, d, J 8 Hz), 6.75 (1H, d, J 8 Hz), 6.56 (1H, d, J 15.5 Hz), 4.85 (m), 4.60 (2H, s), 3.35 (4H, m), 3.05 (2H, m), 2.95 (2H, m), 2.7 (2H, t, J 8 Hz), 1.8 (2H, m), 1.65 (2H, m), 1.5 (2H, m), 1.3 (6H, br s).

(v) Sulphamate Salt

Figure 4:
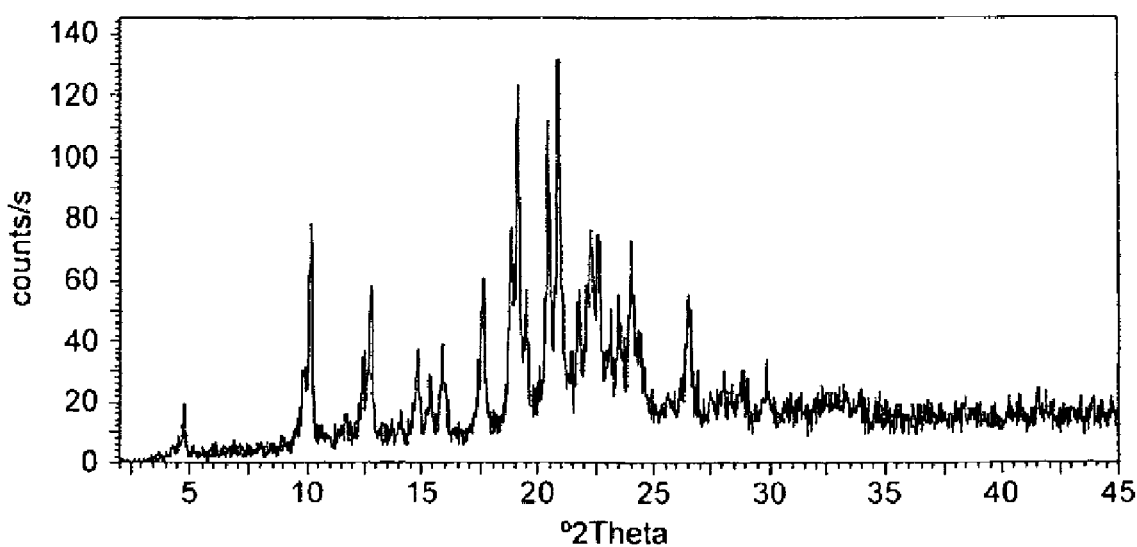
FIG. 4 illustrates the X-Ray Powder Diffraction (XRPD) pattern of the product referred to in Example 48(v).

In a similar fashion the title salt was prepared (0.56 g). The XRPD pattern of this product is shown in FIG. 4.

(vi) Sulphanilate Salt

Figure 5:
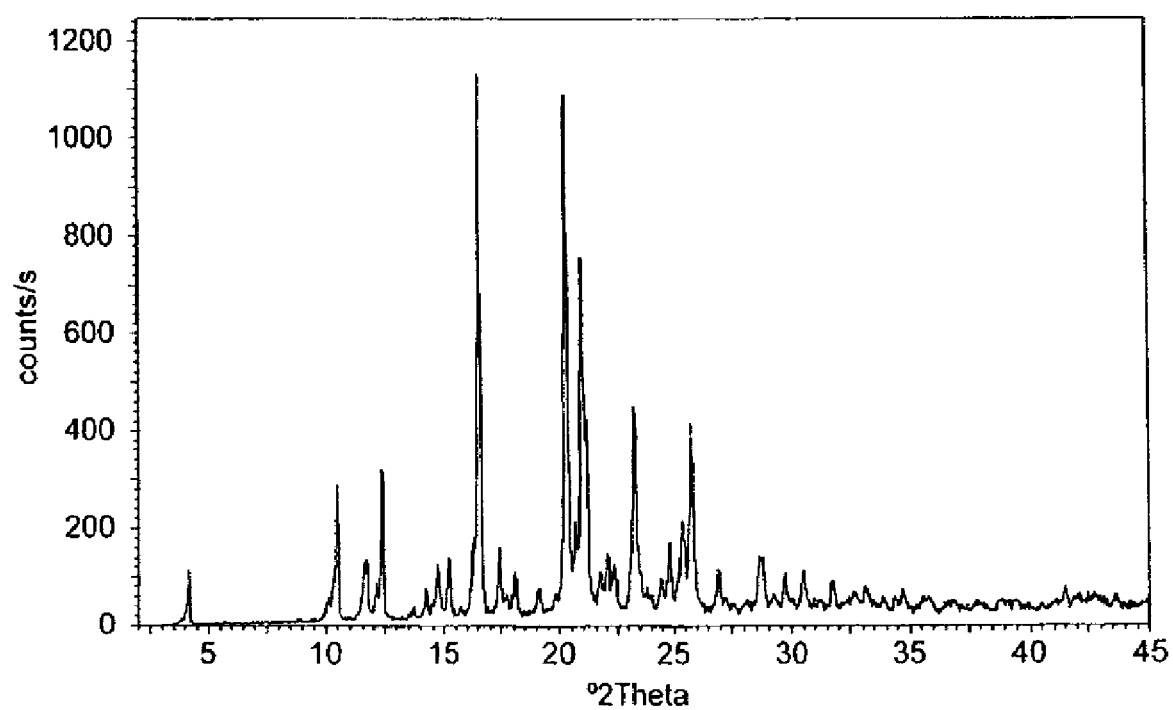
FIG. 5 illustrates the X-Ray Powder Diffraction (XRPD) pattern of the product referred to in Example 48(vi).

In a similar fashion, the title salt was prepared (0.52 g). The XRPD pattern of this product is shown in FIG. 5. M Pt 117° C.-123° C.

δ (MeOH-d₄) 7.65 (1H, s), 7.62 (1H, d, J 7 Hz), 7.45 (2H, m), 7.35 (2H, m), 7.25 (1H, s), 7.05 (1H, d, J 7 Hz), 6.7 (1H, d, J 8 Hz), 6.55 (2H, d, J 8 Hz), 4.9 (m), 4.55 (2H, s), 3.33 (4H, m), 3.05 (2H, m), 2.95 (2H, t, J 8 Hz), 2.65 (2H, t, J 8 Hz), 1.8 (2H, m), 1.6 (2H, m), 1.48 (2H, m), 1.3 (6H, br s)

Example 49

N²-{[3-(4-{[6-({(2R)-2-Hydroxy-2-[4-hydroxy-3-(hydroxymethyl)phenyl]ethyl}amino)hexyl]oxy}butyl)phenyl]sulfonyl}glycinamide acetate i) N²-[(3-Iodophenyl)sulfonyl]-N²-{[2-(trimethylsilyl)ethoxy]methyl}glycinamide N²-[(3-Iodophenyl)sulfonyl]glycinamide (0.14 g) was stirred with sodium hydride (60% oil dispersion, 0.02 g) in DMF (2 ml) at 21° under nitrogen for 15 min. 2-Trimethylsilylethoxymethyl chloride (0.08 ml) was added and stirring was continued for 1.5 h. The mixture was poured into pH 6.4 phosphate buffer and the product was extracted three times with ethyl acetate. The combined organic layers were washed with brine, dried (MgSO₄), concentrated and applied to a silica Bond Elut Cartridge (5 g) in dichloromethane containing methanol. The cartridge was eluted with dichloromethane, diethyl ether and ethyl acetate to give the title compound (0.16 g), LCMS RT=3.49 min.

ii) N²-[(3-{4-[(6-Iodohexyl)oxy]but-1-ynyl}phenyl) sulfonyl]-N²-{[2-(trimethylsilyl)ethoxy] methyl}glycinamide compound with N²-[(3-{4-[(6-bromohexyl)oxy]but-1-ynyl}phenyl)sulfonyl]-N-2-{[2-(trimethylsilyl)methyl]methyl}glycinamide (55: 45)

N²-[(3-Iodophenyl)sulfonyl]-N²-{[2-(trimethylsilyl) ethoxy]methyl}glycinamide (0.16 g) was stirred with 6-bromohexyl but-3-ynyl ether (0.086 g) in acetonitrile (2 ml) and diisopropylethylamine (2 ml) under nitrogen for 10 min. Cuprous iodide (0.01 g) and dichlorobis(triphenylphosphine) palladium (0.02 g) were added and the stirring continued for 2 h.

The solution was evaporated to dryness and applied to a Bond Elut cartridge (5 g) in dichloromethane. The cartridge was eluted with dichloromethane and diethyl ether to give the title compounds (0.165 g), LCMS RT 3.93 min (bromide) and 4.02 min (iodide).

ii) 2-Azido-1-(2,2-dimethyl-4H-1,3-benzodioxin-6-yl)ethanone

2-Bromo-1-(2,2-dimethyl-4H-1,3-benzodioxin-6-yl)ethanone (Glaxo DE 3513885, 1985) (52 g) in DMF (300 ml) was treated with sodium azide (12.24 g) and the mixture was stirred for 2 h at 20° C. The reaction mixture was diluted with ethyl acetate and washed with water and dried (MgSO$_4$). The solvent was removed under reduced pressure to give the title compound (39.11 g). TSP+ve 248(MH)$^+$.

iii) (1R)-2-Azido-1-(2,2-dimethyl-4H-1,3-benzodioxin-6-yl)ethanol

R-(+)-2-Methyl-CBS-oxazaborolidine solution in toluene (1M, 7.5 ml) was added to THF (75 ml) and the solution was diluted to 0° C. Borane-THF complex (1M solution in THF, 125 ml) was added and the mixture was stirred under nitrogen for 15 min. A solution of 2-azido-1-(2,2-dimethyl-4H-1,3-benzodioxin-6-yl)ethanone (24.7 g) in THF (250 ml) was added dropwise over 1.5 h at 5° C. The mixture was stirred for a further 1 h and then cautiously treated with 2M HCl (100 ml). The reaction mixture was extracted with ether and the organic layer was washed with 2M HCl, NaHCO$_3$, brine, dried (MgSO$_4$). The solvent was removed by evaporation and the residue was chromatographed on a Biotage column eluting with diethyl ether-petrol (40-60° C.) (1:9; 1:1) to give the title compound (16.99 g). ES+ve 250 (MH)$^+$.

iv) (1R)-2-Amino-1-(2,2-dimethyl-4H-1,3-benzodioxin-6-yl)ethanol (1R)-2-Azido-1-(2,2-dimethyl-4H-1,3-benzodioxin-6-yl) ethanol (16.99 g) was hydrogenated over 10% Pd—C (1 g) in ethanol (300 ml). The catalyst was collected by filtration, and washed with ethanol. The combined washings were evaporated under reduced pressure and the residue was triturated in diethyl ether to give the title compound (5.86 g). The mother liquors were chromatographed on a Biotage column eluting with toluene:ethanol:aqueous ammonia (85:14:1) to give a further batch of the title compound (5.99 g). LCMS RT=1.68 min, ES+ve 206 (MH-H$_2$O)$^+$.

vi) N²-[(3-{4-[(6-{[(2R)-2-(2,2-Dimethyl-4H-1,3-benzodioxin-6-yl)-2-hydroxyethyl]amino}hexyl) oxy]but-1-ynyl}phenyl)sulfonyl]-N²-{[2-(trimethylsilyl)ethoxy]methyl}glycinamide (1R)-2-Amino-1-(2,2-dimethyl-4H-1,3-benzodioxin-6-yl)ethanol (0.134 g) was stirred with N²-[(3-{4-[(6-iodohexyl)oxy]but-1-ynyl}phenyl)sulfonyl]-N²-{[2-(trimethylsilyl)ethoxy]methyl}glycinamide compound with N²-[(3-{4-[(6-bromohexyl)oxy]but-1-ynyl}phenyl)sulfonyl]-N²-{[2-(trimethylsilyl)ethoxy]methyl}glycinamide (55:45) (0.165 g) in DMF (3 ml) for 4 days at 21°. The mixture was evaporated to dryness and applied to a silica Bond Elut Cartridge (5 g) in ethyl acetate. This was eluted with ethyl acetate and then 10% methanol in ethyl acetate to give the title compound (0.081 g) LCMS RT=3.04 min.

vii) N²-[(3-{4-[(6-{[(2R)-2-(2,2-Dimethyl-4H-1,3-benzodioxin-6-yl)-2-hydroxyethyl]amino}hexyl) oxy]butyl}phenyl)sulfonyl]-N²-{[2-(trimethylsilyl) ethoxy]methyl}glycinamide N²-[(3-{4-[(6-{[(2R)-2-(2,2-Dimethyl-4H-1,3-benzodioxin-6-yl)-2-hydroxyethyl]amino}hexyl)oxy]but-1-ynyl}phenyl)sulfonyl]-N²-{[2-(trimethylsilyl)ethoxy]methyl}glycinamide (0.09 g) was stirred with platinum oxide (0.023 g) in ethanol (20 ml) under hydrogen for 3.5 h. The catalyst was filtered off with the aid of celite and the filter cake was leached with ethanol. The combined filtrates were evaporated to give the title compound (0.091 g) LCMS RT=3.10 min.

viii) N²-{[3-(4-{[6-({(2R)-2-Hydroxy-2-[4-hydroxy-3-(hydroxnmethyl)phenyl]ethyl}amino)hexyl] oxy}butyl)phenyl]sulfonyl}glycinamide acetate N²-[(3-{4-[(6-{[(2R)-2-(2,2-dimethyl-4H-1,3-benzodioxin-6-yl)-2-hydroxyethyl]amino}hexyl)oxy] butyl}phenyl)sulfonyl]-N²-{[2-(trimethylsilyl)ethoxy] methyl}glycinamide (0.091 g) was stirred under a reflux condenser at 80° in acetic acid (2 ml) and water (1 ml) for 3.5 h. The solution was evaporated to dryness and re-evaporated twice with methanol to give a gum. The residue was dissolved in methanol and loaded onto two 20×20 cm preparative silica gel coated plates (1 mm layer). The plates were run in dichloromethane:ethanol:0.880 ammonia solution, 25:8:1 and elution of the main band and evaporation gave a gum. This was dissolved in acetic acid (2 ml) and evaporated to dryness and re-evaporated with methanol to give the title compound (0.019 g) LCMS RT=2.31 min, ES+ve 552 (MH)$^+$.

Example 50

6α,9α-Difluoro-17α-[(2-furanylcarbonyl)oxy]-11β-hydroxy-16α-methyl-3-oxo-androsta-1,4-diene-17β-carbothioic acid S-fluoromethyl ester Unsolvated Form 1 (a) 6α,9α-Difluoro-17α-[(2-furanylcarbonyl) oxy]-11β-hydroxy-16α-methyl-3-oxo-androsta-1,4-diene-17β-carbothioic acid A solution of 6α,9α-difluoro-11β, 17α-dihydroxy-16α-methyl-3-oxo-androsta-1,4-diene-17β-carbothioic acid (prepared in accordance with the procedure described in GB 2088877B) (18 g, 43.64 mmol) in anhydrous dichloromethane (200 ml) and triethylamine (15.94 ml, 114 mmol) was treated at <5° C. with a solution of 2-furoyl chloride (11.24 ml, 114 mmol) in anhydrous dichloromethane (100 ml) over approximately 40 min. The solution was stirred at <5° C. for 30 min. The resulting solid was collected by filtration, washed successively with 3.5% aqueous sodium hydrogen carbonate solution, water, 1M hydrochloric acid, and water and dried in vacuo at 60° C. to give a cream coloured solid. The dichloromethane filtrate was washed successively with 3.5% sodium hydrogen carbonate solution, water, 1M hydrochloric acid, water, dried ($Na_2SO_4$) and evaporated to give a cream coloured solid which was combined with that isolated above. The combined solids (26.9 g) were suspended in acetone (450 ml) and stirred. Diethylamine (16.8 ml, 162 mmol) was added and the mixture stirred at room temperature for 4.5 h. The mixture was concentrated and the precipitate collected by filtration and washed with a little acetone. The washings and filtrate were combined, concentrated and loaded onto a silica gel Biotage column which was eluted with 24:1 chloroform:methanol. Fractions which contained the more polar component were combined and evaporated to give a cream coloured solid. This was combined with the solid isolated above and dried in vacuo to give a pale beige coloured solid (19.7 g). This was dissolved in warm water, the pH adjusted to 2 with concentrated hydrochloric acid and the mixture extracted with ethyl acetate. The organic extract was dried ($Na_2SO_4$) and evaporated to give, after drying at 50° C., the title compound as a cream coloured solid (18.081 g, 82%): LCMS retention time 3.88 min, m/z 507 MH$^+$, NMR δ ($CDCl_3$) includes 7.61 (1H, m), 7.18-7.12 (2H, m), 6.52 (1H, dd, J 4, 2 Hz), 6.46 (1H, s), 6.41 (1H, dd, J 10, 2 Hz), 5.47 and 5.35 (1H, 2 m), 4.47 (1H, bd, J 9 Hz), 3.37 (1H, m), 1.55 (3H, s), 1.21 (3H, s), 1.06 (3H, d, J 7 Hz).

A suspension of the product of part (a) (2.5 g, 4.94 mmol) was dissolved in anhydrous N,N-dimethylformamide (25 ml) and sodium hydrogen carbonate (465 mg, 5.53 mmol) was added. The mixture was stirred at −20° C. and bromofluoromethane (0.77 ml, 6.37 mmol) was added and the mixture was stirred at −20° C. for 2 h. Diethylamine (2.57 ml, 24.7 mmole) was added and the mixture stirred at −20° C. for 30 min. The mixture was added to 2M hydrochloric acid (93 ml) and stirred for 30 min. Water (300 ml) was added and the precipitate was collected by filtration, washed with water and dried in vacuo at 50° C. to give a white solid which was recrystallised from acetone/water (to yield the acetone solvate of 6α,9α-difluoro-17α-[(2-furanylcarbonyl)oxy]-11β-hydroxy-16α-methyl-3-oxo-androsta-1,4-diene-17β-carbothioic acid S-fluoromethyl ester) and dried in vacuo at 50° C. to give the title compound (2.351 g, 88%): LCMS retention time 3.66 min, m/z 539 MH$^+$, NMR δ ($CDCl_3$) includes 7.60 (1H, m), 7.18-7.11 (2H, m), 6.52 (1H, dd, J 4.2 Hz), 6.46 (1H, s), 6.41 (1H, dd, J 10, 2 Hz), 5.95 and 5.82 (2H dd, J 51, 9 Hz), 5.48 and 5.35 (1H, 2 m), 4.48 (1H, m), 3.48 (1H, m), 1.55 (3H, s), 1.16 (3H, s), 1.06 (3H, d, J7 Hz).

Example 51

6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester Example 51 was prepared using a method analogous to that described for Example 50: LCMS retention time 3.51 min, m/z 570 MH$^+$

BIOLOGICAL ACTIVITY

The potencies of the aforementioned compounds were determined using frog melanophores transfected with the human beta 2 adrenoreceptor. The cells were incubated with melatonin to induce pigment aggregation. Pigment dispersal was induced by compounds acting on the human beta 2 adrenoreceptor. The beta 2 agonist activity of test compounds was assessed by their ability to induce a change in light transmittance across a melanophore monolayer (a consequence of pigment dispersal). At the human beta 2 adrenoreceptor, compounds of examples 1-49 had $IC_{50}$ values below 1 μM.

Potency at other beta adrenoreceptor subtypes was determined using chinese hamster ovary cells transfected with either the human beta I adrenoreceptor or the human beta 3 adrenoreceptor. Agonist activity was assessed by measuring changes in intracellular cyclic AMP.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. 3-(3-{[7-({(2R)-2-hydroxy-2-[4-hydroxy-3-(hydroxymethyl)phenyl]ethyl}-amino)heptyl]oxy}propyl)benzenesulfonamide, or a salt or solvate thereof.

2. A compound according to claim 1, wherein the salt or solvate is pharmaceutically acceptable.

3. A compound according to claim 1, wherein the compound is in the form of a salt formed with a pharmaceutically acceptable acid selected from the group consisting of cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

4. A compound according to claim 1 which is 3-(3-{[7-({(2R)-2-hydroxy-2-[4-hydroxy-3-(hydroxymethyl)phenyl]ethyl}-amino)heptyl]oxy}propyl)benzenesulfonamide 4-phenylbenzoate.

5. A compound according to claim 1 which is 3-(3-{[7-({(2R)-2-hydroxy-2-[4-hydroxy-3-(hydroxymethyl)phenyl]ethyl}-amino)heptyl]oxy}propyl)benzenesulfonamide triphenylacetate.

6. A compound according to claim 1 which is 3-(3-{[7-({(2R)-2-hydroxy-2-[4-hydroxy-3-(hydroxymethyl)phenyl]ethyl}-amino)heptyl]oxy}propyl)benzenesulfonamide 4-phenylcinnamate.

7. A compound according to claim 1 which is 3-(3-{[7-({(2R)-2-hydroxy-2-[4-hydroxy-3-(hydroxymethyl)phenyl]ethyl}-amino)heptyl]oxy}propyl)benzenesulfonamide sulphamate.

8. A compound according to claim 1 which is 3-(3-{[7-({(2R)-2-hydroxy-2-[4-hydroxy-3-(hydroxymethyl)phenyl]ethyl}-amino)heptyl]oxy}propyl)benzenesulfonamide sulphanilate.

9. A pharmaceutical formulation comprising a compound according to claim 1 or a pharmaceutically acceptable salt or solvate thereof, and a pharmaceutically acceptable carrier or excipient, and optionally one or more other therapeutic ingredients selected from the group consisting of anti-inflammatory agents, anticholinergic agents, anti-infective agents, antihistamines, other β-adrenoreceptor agonists, PDE4 inhibitors, and combinations thereof.

10. A combination comprising a compound according to claim 1 or a pharmaceutically acceptable salt or solvate thereof, and one or more other therapeutic ingredients selected from the group consisting of anti-inflammatory agents, anticholinergic agents, anti-infective agents, antihistamines, other β-adrenoreceptor agonists, PDE4 inhibitors, and combinations thereof.

11. A combination comprising 3-(3-{[7-({(2R)-2-hydroxy-2-[4-hydroxy-3-(hydroxymethyl)phenyl]ethyl}-amino)heptyl]oxy}propyl)benzenessulfonamide, or a salt or solvate thereof, and 6α, 9α-difluoro-17α-[(2-furanylcarbonyl)oxy]-11β-hydroxy-16α-methyl-3-oxo-androsta-1,4-diene-17β-carbonthioic acid S-fluoromethyl ester.

12. 3-(3-{[7-({(2R)-2-hydroxy-2-[4-hydroxy-3-(hydroxymethyl)phenyl]ethyl}-amino)heptyl]oxy}propyl)benzenesulfonamide (E)-3-(napthalen-2-yl)-2-propenoate.

13. A pharmaceutical formulation comprising a compound according to claim 12 or a pharmaceutically acceptable salt or solvate thereof, and a pharmaceutically acceptable carrier or excipient, and optionally one or more other therapeutic ingredients selected from the group consisting of anti-inflammatory agents, anticholinergic agents, anti-infective agents, antihistamines, other β-adrenoreceptor agonists, PDE4 inhibitors, and combinations thereof.

14. A combination comprising a compound according to claim 12 or a pharmaceutically acceptable salt or solvate thereof, and one or more other therapeutic ingredients selected from the group consisting of anti-inflammatory agents, anticholinergic agents, anti-infective agents, antihistamines, other β-adrenoreceptor agonists, PDE4 inhibitors, and combinations thereof.

15. A combination comprising 3-(3-{[7-({(2R)-2-hydroxy-2-[4-hydroxy-3-(hydroxymethyl)phenyl]ethyl}-amino)heptyl]oxy}propyl)benzenesulfonamide (E)-3-(napthalen-2-yl)-2-propenoate and 6α, 9α-difluoro-17α-[(2-furanylcarbonyl)oxy]-11β-hydroxy-16α-methyl-3-oxo-androsta-1,4-diene-17β-carbonthioic acid S-fluoromethyl ester.

* * * * *

UNITED STATES PATENT AND TRADEMARK OFFICE
CERTIFICATE OF CORRECTION

PATENT NO. : 7,442,836 B2
APPLICATION NO. : 11/426657
DATED : October 28, 2008
INVENTOR(S) : Keith Biggadike et al.

It is certified that error appears in the above-identified patent and that said Letters Patent is hereby corrected as shown below:

In Column 75, line 9, "carbonthioic" should read -- carbothioic --
In Column 76, line 15, "carbonthioic" should read -- carbothioic --

Signed and Sealed this

Third Day of February, 2009

JOHN DOLL
*Acting Director of the United States Patent and Trademark Office*